United States Patent
Francis et al.

(10) Patent No.: US 9,834,597 B2
(45) Date of Patent: Dec. 5, 2017

(54) MODIFIED FC POLYPEPTIDES, FC CONJUGATES, AND METHODS OF USE THEREOF

(71) Applicant: The Regents of the University of California, Oakland, CA (US)

(72) Inventors: Matthew B. Francis, Berkeley, CA (US); Chawita Netirojjanakul, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 234 days.

(21) Appl. No.: 14/426,048

(22) PCT Filed: Sep. 19, 2013

(86) PCT No.: PCT/US2013/060724
§ 371 (c)(1),
(2) Date: Jul. 20, 2015

(87) PCT Pub. No.: WO2014/047357
PCT Pub. Date: Mar. 27, 2014

(65) Prior Publication Data
US 2015/0218258 A1    Aug. 6, 2015

Related U.S. Application Data

(60) Provisional application No. 61/711,589, filed on Oct. 9, 2012, provisional application No. 61/704,166, filed on Sep. 21, 2012.

(51) Int. Cl.
C07K 16/00   (2006.01)
C07K 16/18   (2006.01)
C07K 16/28   (2006.01)
A61K 47/68   (2017.01)

(52) U.S. Cl.
CPC .............. *C07K 16/18* (2013.01); *A61K 47/68* (2017.08); *C07K 16/2863* (2013.01); *C07K 2317/40* (2013.01); *C07K 2317/52* (2013.01); *C07K 2317/732* (2013.01)

(58) Field of Classification Search
None
See application file for complete search history.

(56) References Cited

U.S. PATENT DOCUMENTS 8,053,560 B2    11/2011   Sheffer et al.
2009/0286964 A1   11/2009  Gegg et al.
2011/0263832 A1   10/2011  Krantz et al.

FOREIGN PATENT DOCUMENTS

WO    WO 2006-107124 A1    10/2006
WO    WO 2012-059882 A2     5/2012

OTHER PUBLICATIONS

Scheck, J Am Chem Soc, 130:11762-11770, 2008.*
Behrens et al , J Am Chem Soc, 133:16398-16401, e published Sep. 28, 2011.*
Netirojjanakul, et al.; "Synthetically modified Fc domains as building blocks for immunotherapy applications"; Chemical Science; vol. 4, No. 1, pp. 266-272 (Nov. 1, 2012).
Shinoda, et al.; "Complete amino acid sequence of the Fc region of a human delta chain"; Proc Natl Acad Sci USA; vol. 78, No. 2; pp. 785-789 (Feb. 1981).

* cited by examiner

*Primary Examiner* — Mark Halvorson
(74) *Attorney, Agent, or Firm* — Bozicevic Field & Francis, LLP; Paula A. Borden; Glenn J. Foulds

(57) ABSTRACT

The present disclosure provides modified Fc domains having one or more attachment moieties for attaching a heterologous functional moiety; and methods of generating the modified Fc domains. The present disclosure provides Fc conjugates; and methods of making the conjugates. The Fc conjugates are useful in various methods, which are also provided.

17 Claims, 18 Drawing Sheets

```
ATGTACAGGATGCAACTTCCTGTCTTGCATTGCACTAAGTCTTTGCACTTGTTCACGAATTCGATATCGGCCATGGTTAG
 M  Y  R  M  Q  L  L  S  C  I  A  L  S  L  A  L  V  T  N  S  I  S  A  M  V  R
ATCTGACAAACTCACACATGCCACGTGCCCAGgtaagcagcccaggcctgccctccagctcagtcaaggcgggacaggtgcctag
 S  D  K  T  H  T  C  P  P  C  P  A
agtagcctgcatccaggggacaggcccagccccagcgggtgctgacacgtccacctcatcttcctcagCACCTGAACTCCTGGGGGGACCGTC
                                                     P  E  L  L  G  G  P  S
AGTCTTCCTCTTCCCCCCAAAACCCAAGGACACCCTCATGATCTCCCGGACCCCTGAGGTCACATGCGTGGTGGTG
 V  F  L  F  P  P  K  P  K  D  T  L  M  I  S  R  T  P  E  V  T  C  V  V  V
GACGTGAGCCACGAAGACCCTGAGGTCAAGTTCAACTGGTACGTGGACGGCGTGGAGGTGCATAATGCCAAGAC
 D  V  S  H  E  D  P  E  V  K  F  N  W  Y  V  D  G  V  E  V  H  N  A  K  T
AAAGCCGCGGGAGGAGCAGTACAACAGCACGTACCGTGTGGTCAGCGTCCTCACCGTCCTGCACCAGGACTGGCT
 K  P  R  E  E  Q  Y  N  S  T  Y  R  V  V  S  V  L  T  V  L  H  Q  D  W  L
GAATGGCAAGGAGTACAAGTGCAAGGTCTCCAACAAAGCCCTCCCAGCCCCCATCGAGAAAACCATCTCCAAAGC
 N  G  K  E  Y  K  C  K  V  S  N  K  A  L  P  A  P  I  E  K  T  I  S  K  A
CAAAGgtgggaccgtggggtgcgagggtgcacatggaggaggccggctccggcccaccctctgccctgagagtgactgctgtaccaacctctgtcc
 K
ctacagGGCAGCCCCGAGAACCACAGGTGTACACCCTGCCCCCATCCCGGATGAGCTGACCAAGAACCAGGTCAG
       Q  P  R  E  P  Q  V  Y  T  L  P  P  S  R  D  E  L  T  K  N  Q  V  S
CCTGACCTGCCTGGTCAAAGGCTTCTATCCCAGCGACATCGCCGTGGAGTGGGAGAGCAATGGGCAGCCGGAGA
 L  T  C  L  V  K  G  F  Y  P  S  D  I  A  V  E  W  E  S  N  G  Q  P  E  N
ACAACTACAAGACCACGCCTCCCGTGCTGGACTCCGACGGCTCCTTCTTCCTCTACAGCAAGCTCACCGTGGACAA
 N  Y  K  T  T  P  P  V  L  D  S  D  G  S  F  F  L  Y  S  K  L  T  V  D  K
GAGCAGGTGGCAGCAGGGGAACGTCTTCTCATGCTCCGTGATGCATGAGGCTCTGCACAACCACTACACGCAGAA
 S  R  W  Q  Q  G  N  V  F  S  C  S  V  M  H  E  A  L  H  N  H  Y  T  Q  K
GAGCCTCTCCCTGTCTCCGGGTAAATGA...
 S  L  S  L  S  P  G  K
```

FIG. 1C

GenBank 3S7G_A
*Homo sapiens* IgG1 Fc
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325)
227 aa

```
  1 stkgpsvfpl apcsrstses taalgclvkd yfpepvtvsw nsgaltsgvh tfpavlqssg
 61 lyslssvvtv psSnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 10A

GenBank AAA52770
*Homo sapiens* IgD Fc (amino acids 162-383)
222 aa

```
  1 ptkapdvfpi isgcrhpkdn spvvlaclit gyhptsvtvt wymgtqsqpg rtfpeiqrrd
 61 syymtssqls tplqqwrqge ykcvvqhtas kskkeifrwp espkaqassv ptaqpqaegs
121 lakattapat trntgrggee kkkekekeeq eeretktpec psht qplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtlnasrs  levsyvtdhg pmk
```

GenBank O308221A
*Homo sapiens* IgM Fc
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 10B

GenBank P01876
*Homo sapiens* IgA Fc (amino acids 120-353)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk cksnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 10C

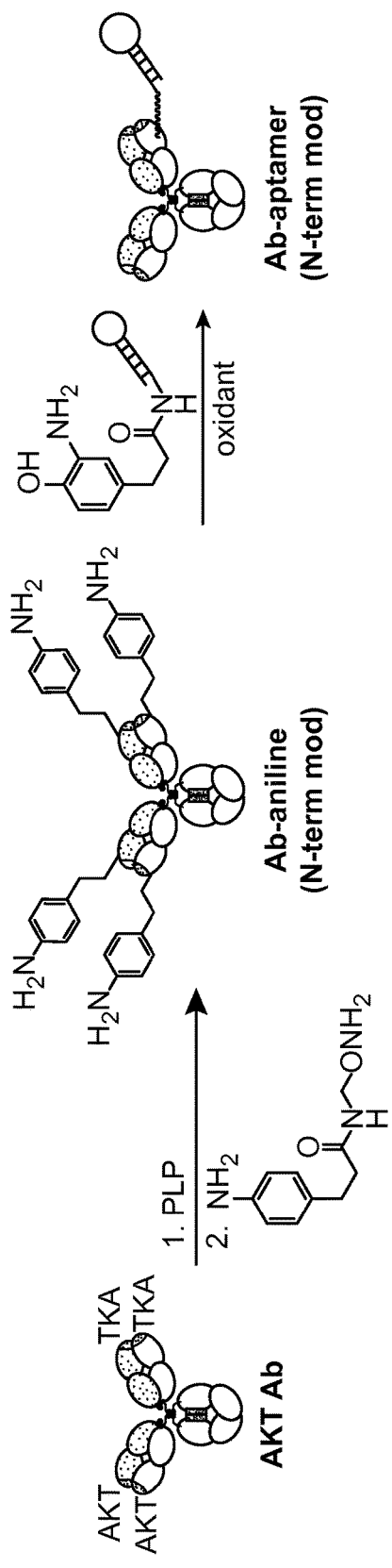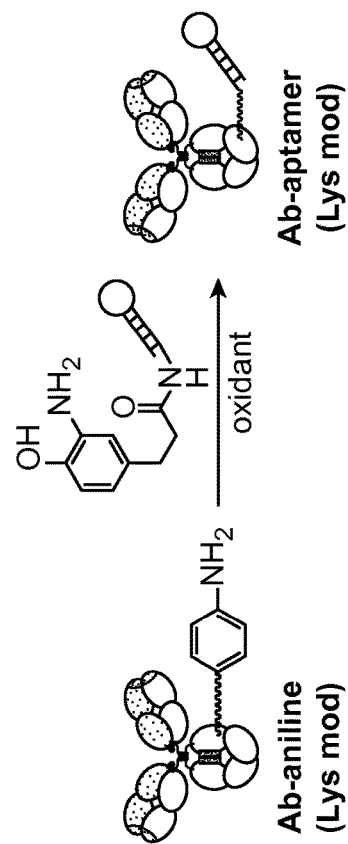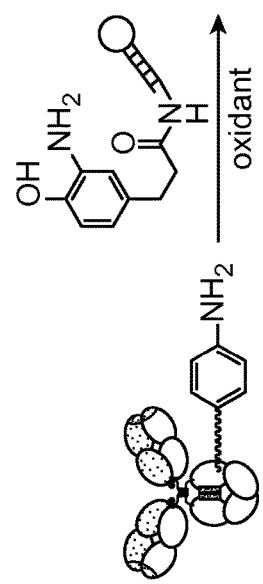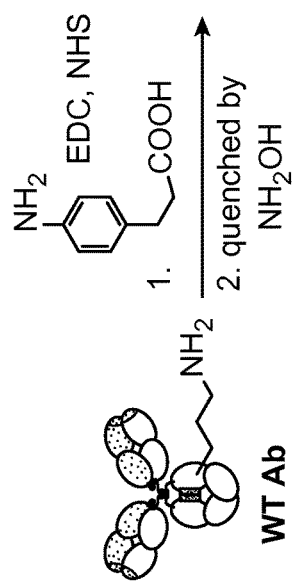
FIG. 11A
FIG. 11B

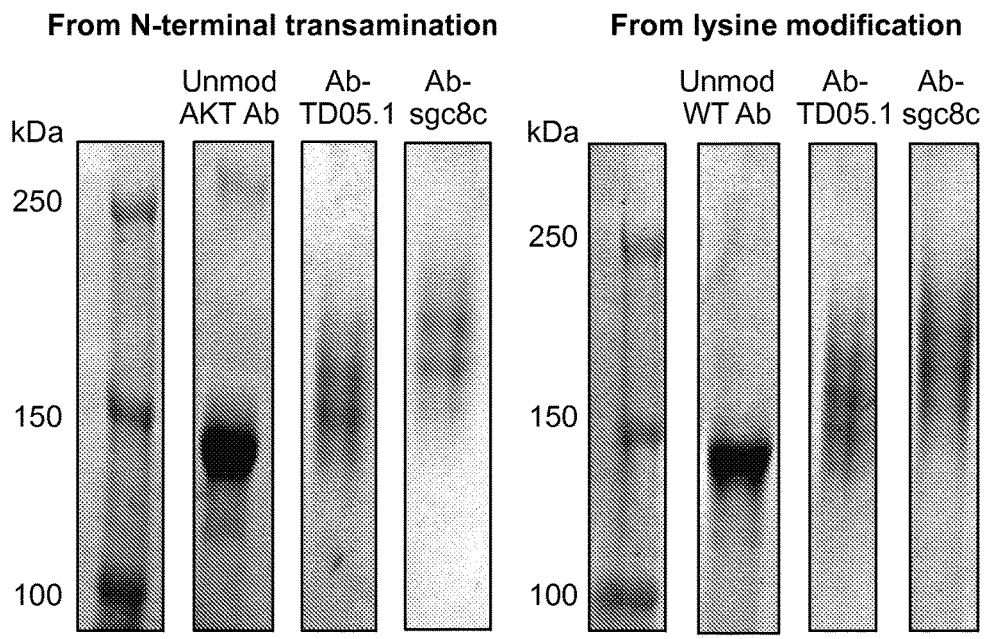
FIG. 12A
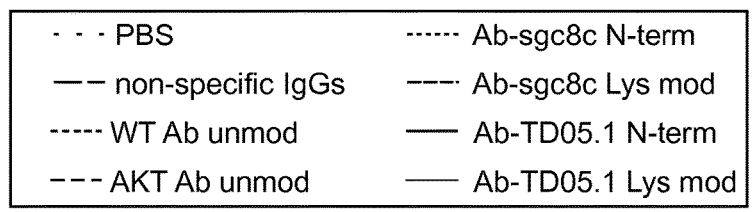
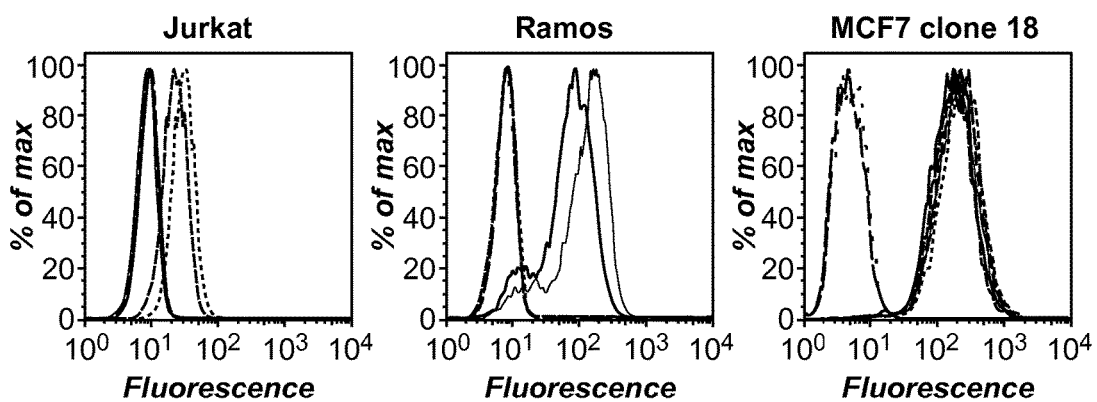
FIG. 12B

AKT-anti-HER2 heavy chain (human IgG1 isotype)

ATGTACAGGATGCAACTCCTGTCTTGCATTGCACTAAGTCTTGCACTTGTCACGAATT
CGGCCAAAACAGAAGTCCAACTCGTGCTGTGCCTCCGGATTTAATATCAAAGATACTTATATA
GGAAGCCTGCGCTTGAGCTGTGCTGCCCAGGCTCCTGGAAAGGGTCTGGAGTGGGTGGCGAGAATCTACCC
CACTGGGTTCGCCAGGCTCCTGGAAAGGGTCTGGAGTGGGTGGCGAGAATCTACCC
AACCAATGGTTATACCCGCTATGCAGACAGCGTGAAAGGGCGGTTTACAATTAGTG
CCGACACATCTAAAAATACCGCTTACCTCCAGATGAACTCTCTGAGGGCCGAGGAC
ACGGCTGTGTATTATTGCAGCCGGTGGGGTGGAGACGGATTCTATGCTATGGACTAT
TGGGGTCAGGGCACTCTCGTCACTGTAAGCAGTGCCAGCAGTACCAAAGGGCCTAGTGT
CTTTCCCCTTGCTCTCATCTAGCAAATCTACCAGCGGGGCACCGCCGCCCTGGGATG
CCTGGTCAAGGACTATTTCCTGAGCCAGTCACCGTCCTGGAATAGTGGCGCCTT
GACTTCTGTGTTTCACACATTCCCGCCGTCCTTCAATCTAGTGGCTGTACTCTCTC
TCCAGTGTGTGACGGTACCCAGTTCAAGTCTTGGGCACACAGACCTATATCTGCAAT
GTGAACCACAAGCCCAGCAATACACACACGCCCACCGTGCCCAGtaagccagccaggcctccagtcca
GCTGTGACAAACTCACACACGCCCACCGTGCCCAGgtaagccagcccaggcctccaagcctcagctca
aggcgggacaggtgccctagagtagccctgatcaggacagtctctctgcaggggtgctgacagtccacctccatctcctcagCA
CCTGAACTCCTGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCA
AGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAA
CAAAGCCCTCCCAGCCCCCATCGAGAAAACCATCTCCAAAGCCAAAGgtgggacccgtggg
gtgcgagggccacagtgacagaggccgctcggccaccctgccctgagtgactgctgtaccaactctgtcctacagGGCA
GCCCCGAGAACCACAGGTGTACACCCTGCCCCCATCCCGGGATGAGCTGACCAAGA
ACCAGGTCAGCCTGACCTGCCTGGTCAAAGGCTTCTATCCCAGCGACATCGCCGTGG
AGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTAC
ACGCAGAAGAGCCTCTCCCTGTCTCCGGGTAAATGA (SEQ ID NO:106)

FIG. 13A

AKT-anti-HER2 light chain

ATGTACAGGATGCAACTCCTGTCTTGCATTGCACTAAGTCTTGCACTTGTCACGAATTCGGCT
AAAACTGACATCCAAATGACTCAAAGCCCCAGTTCCCTGAGCGCTTCCGTAGGGACAGGG
TGACAATAACATGTCGGGCTAGCCAGGATGTCAATACAGCTGTCGCTTGGTACCAGCAAAA
GCCCGGAAAGGGCCCAAAGCTTCTTATATACAGGCCCAGTTTCCTCTATTCTGGCGTGCCGA
GCAGGTTCTCTGGATCTCGGTCCGGGACCGATTTCACACTGACCATTAGTTCTCTGCAGCCA
GAGGACTTTGCAACATACTACTGCCAGCAGCGTACACACCCCAACCTTTGGTCAGGG
CACGAAGGTGGAAATCAAGCGTAGAACTGGAAACTGCCTCTGTTGTGCCTGCTGAATAACTTCTATCCCAAA
GAGGCCAAAGTACAGTGGAAGGTGGATAACGCCCTCCAATCGGGTAACTCCCAGGAGAGTG
TCACAGAGCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCTGAGCTCG
CCCGTCACAAAGAGCTTCAACAGGGGAGAGTGT (SEQ ID NO:107)

FIG. 13B

AKT-anti-HER2 heavy chain (human IgG1 isotype)

AKTEVQLVESGGGLVQPGGSLRLSCAASGFNIKDTYIHWVRQAPGKGLEWVARIYPTN
GYTRYADSVKGRFTISADTSKNTAYLQMNSLRAEDTAVYYCSRWGGDGFYAMDYWG
QGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPPKSCDKTHTC
PPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK (SEQ ID NO:108)

AKT-anti-HER2 light chain

AKTDIQMTQSPSSLSASVGDRVTITCRASQDVNTAVAWYQQKPGKAPKLLIYSASFLYS
GVPSRFSGSRSGTDFTLTISSLQPEDFATYYCQQHYTTPPTFGQGTKVEIKRTVAAPSVFIF
PPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:109)

FIG. 13C

SEQUENCE LISTING

```
<160> NUMBER OF SEQ ID NOS: 105

<210> SEQ ID NO 1
<211> LENGTH: 980
<212> TYPE: DNA
<213> ORGANISM: Artificial Sequence
<220> FEATURE:
<223> OTHER INFORMATION: Synthetic nucleic acid sequence

<400> SEQUENCE: 1
atgtacagga tgcaactcct gtcttgcatt gcactaagtc ttgcacttgt cacgaattcg      60
atatcggcca tggttagatc tgacaaaact cacacatgcc caccgtgccc aggtaagcca     120
gcccaggcct cgccctccag ctcaaggcgg gacaggtgcc ctagagtagc ctgcatccag     180
ggacaggccc cagccgggtg ctgacacgtc cacctccatc tcttcctcag cacctgaact     240
cctgggggga ccgtcagtct tcctcttccc cccaaaaccc aaggacaccc tcatgatctc     300 ccggaccect gaggtcacat gcgtggtggt ggacgtgagc cacgaagacc ctgaggtcaa     360
gttcaactgg tacgtggacg gcgtggaggt gcataatgcc aagacaaagc cgcgggagga     420
gcagtacaac agcacgtacc gtgtggtcag cgtcctcacc gtcctgcacc aggactggct     480
```

```
gaatggcaag gagtacaagt gcaaggtctc caacaaagcc ctcccagccc ccatcgagaa      540
aaccatctcc aaagccaaag gtgggacccg tggggtgcga gggccacatg acagaggcc      600 ggctcggccc accctctgcc ctgagagtga ctgctgtacc aacctctgtc cctacagggc      660
agccccgaga accacaggtg tacaccctgc cccatcccg ggatgagctg accaagaacc      720
aggtcagcct gacctgcctg gtcaaaggct ctatcccag cgacatcgcc gtggagtggg      780
agagcaatgg gcagccggag aacaactaca agaccacgcc tcccgtgctg gactccgacg      840
gctccttctt cctctacagc aagctcaccg tggacaagag caggtggcag caggggaacg      900
tcttctcatg ctccgtgatg catgaggctc tgcacaacca ctacacgcag aagagcctct      960
ccctgtctcc gggtaaatga                                                 980
```

<210> SEQ ID NO 2
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 2

```
Met Tyr Arg Met Gln Leu Leu Ser Cys Ile Ala Leu Ser Leu Ala Leu
1               5                   10                  15

Val Thr Asn Ser Ile Ser Ala Met Val Arg Ser Asp Lys Thr His Thr
            20                  25                  30

Cys Pro Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
    50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250
```

<210> SEQ ID NO 3

```
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 325
<212> TYPE: PRT
<213> ORGANISM: Homo sapiens

<400> SEQUENCE: 4

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110
```

Val Ala Gly Pro Ser Val Phe Leu Phe Pro Pro Lys Pro Lys Asp Thr
            115                 120                 125

Leu Met Ile Ser Arg Thr Pro Glu Val Thr Cys Val Val Val Asp Val
        130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 5
<211> LENGTH: 246
<212> TYPE: PRT
<213> ORGANISM: Homo sapiens

<400> SEQUENCE: 5

His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn

```
                145                 150                 155                 160
        Gln Val Ser Leu Thr Cys Leu Val Lys Gly Phe Tyr Pro Ser Asp Ile
                        165                 170                 175

Ala Val Glu Trp Glu Ser Asn Gly Gln Pro Glu Asn Asn Tyr Lys Thr
                        180                 185                 190

Thr Pro Pro Val Leu Asp Ser Asp Gly Ser Phe Phe Leu Tyr Ser Lys
                        195                 200                 205

Leu Thr Val Asp Lys Ser Arg Trp Gln Gln Gly Asn Val Phe Ser Cys
        210                 215                 220

Ser Val Met His Glu Ala Leu His Asn His Tyr Thr Gln Lys Ser Leu
        225                 230                 235                 240

Ser Leu Ser Pro Gly Lys
                        245

<210> SEQ ID NO 6
<211> LENGTH: 383
<212> TYPE: PRT
<213> ORGANISM: Homo sapiens

<400> SEQUENCE: 6

Pro Thr Lys Ala Pro Asp Val Phe Pro Ile Ile Ser Gly Cys Arg His
        1               5                   10                  15

Pro Lys Asp Asn Ser Pro Val Val Leu Ala Cys Leu Ile Thr Gly Tyr
                        20                  25                  30

His Pro Thr Ser Val Thr Val Thr Trp Tyr Met Gly Thr Gln Ser Gln
                        35                  40                  45

Pro Gln Arg Thr Phe Pro Glu Ile Gln Arg Arg Asp Ser Tyr Tyr Met
            50                  55                  60

Thr Ser Ser Gln Leu Ser Thr Pro Leu Gln Gln Trp Arg Gln Gly Glu
        65                  70                  75                  80

Tyr Lys Cys Val Val Gln His Thr Ala Ser Lys Ser Lys Lys Glu Ile
                        85                  90                  95

Phe Arg Trp Pro Glu Ser Pro Lys Ala Gln Ala Ser Ser Val Pro Thr
                        100                 105                 110

Ala Gln Pro Gln Ala Glu Gly Ser Leu Ala Lys Ala Thr Thr Ala Pro
                        115                 120                 125

Ala Thr Thr Arg Asn Thr Gly Arg Gly Gly Glu Glu Lys Lys Lys Glu
                        130                 135                 140

Lys Glu Lys Glu Glu Gln Glu Glu Arg Glu Thr Lys Thr Pro Glu Cys
        145                 150                 155                 160

Pro Ser His Thr Gln Pro Leu Gly Val Tyr Leu Leu Thr Pro Ala Val
                        165                 170                 175

Gln Asp Leu Trp Leu Arg Asp Lys Ala Thr Phe Thr Cys Phe Val Val
                        180                 185                 190

Gly Ser Asp Leu Lys Asp Ala His Leu Thr Trp Glu Val Ala Gly Lys
                        195                 200                 205

Val Pro Thr Gly Gly Val Glu Glu Gly Leu Leu Glu Arg His Ser Asn
        210                 215                 220

Gly Ser Gln Ser Gln His Ser Arg Leu Thr Leu Pro Arg Ser Leu Trp
        225                 230                 235                 240

Asn Ala Gly Thr Ser Val Thr Cys Thr Leu Asn His Pro Ser Leu Pro
                        245                 250                 255

Pro Gln Arg Leu Met Ala Leu Arg Glu Pro Ala Ala Gln Ala Pro Val
                        260                 265                 270
```

```
Lys Leu Ser Leu Asn Leu Leu Ala Ser Ser Asp Pro Glu Ala Ala
            275                 280                 285

Ser Trp Leu Leu Cys Glu Val Ser Gly Phe Ser Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Gln Pro Arg Ser Thr Thr Phe Trp Ala Trp
                325                 330                 335

Ser Val Leu Arg Val Pro Ala Pro Ser Pro Gln Pro Ala Thr Tyr
                340                 345                 350

Thr Cys Val Val Ser His Glu Asp Ser Arg Thr Leu Leu Asn Ala Ser
            355                 360                 365

Arg Ser Leu Glu Val Ser Tyr Val Thr Asp His Gly Pro Met Lys
        370                 375                 380

<210> SEQ ID NO 7
<211> LENGTH: 276
<212> TYPE: PRT
<213> ORGANISM: Homo sapiens

<400> SEQUENCE: 7

Val Thr Ser Thr Leu Thr Ile Lys Glx Ser Asp Trp Leu Gly Glu Ser
1               5                   10                  15

Met Phe Thr Cys Arg Val Asp His Arg Gly Leu Thr Phe Gln Gln Asn
                20                  25                  30

Ala Ser Ser Met Cys Val Pro Asp Gln Asp Thr Ala Ile Arg Val Phe
            35                  40                  45

Ala Ile Pro Pro Ser Phe Ala Ser Ile Phe Leu Thr Lys Ser Thr Lys
50                  55                  60

Leu Thr Cys Leu Val Thr Asp Leu Thr Thr Tyr Asx Ser Val Thr Ile
65                  70                  75                  80

Ser Trp Thr Arg Glu Glu Asn Gly Ala Val Lys Thr His Thr Asn Ile
                85                  90                  95

Ser Glu Ser His Pro Asn Ala Thr Phe Ser Ala Val Gly Glu Ala Ser
            100                 105                 110

Ile Cys Glu Asp Asx Asp Trp Ser Gly Glu Arg Phe Thr Cys Thr Val
        115                 120                 125

Thr His Thr Asp Leu Pro Ser Pro Leu Lys Gln Thr Ile Ser Arg Pro
    130                 135                 140

Lys Gly Val Ala Leu His Arg Pro Asx Val Tyr Leu Leu Pro Pro Ala
145                 150                 155                 160

Arg Glx Glx Leu Asn Leu Arg Glu Ser Ala Thr Ile Thr Cys Leu Val
                165                 170                 175

Thr Gly Phe Ser Pro Ala Asp Val Phe Val Glu Trp Met Gln Arg Gly
            180                 185                 190

Glu Pro Leu Ser Pro Gln Lys Tyr Val Thr Ser Ala Pro Met Pro Glu
        195                 200                 205

Pro Gln Ala Pro Gly Arg Tyr Phe Ala His Ser Ile Leu Thr Val Ser
    210                 215                 220

Glu Glu Glu Trp Asn Thr Gly Gly Thr Tyr Thr Cys Val Val Ala His
225                 230                 235                 240

Glu Ala Leu Pro Asn Arg Val Thr Glu Arg Thr Val Asp Lys Ser Thr
                245                 250                 255

Gly Lys Pro Thr Leu Tyr Asn Val Ser Leu Val Met Ser Asp Thr Ala
            260                 265                 270
```

Gly Thr Cys Tyr
       275

<210> SEQ ID NO 8
<211> LENGTH: 353
<212> TYPE: PRT
<213> ORGANISM: Homo sapiens

<400> SEQUENCE: 8

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 9
<211> LENGTH: 222
<212> TYPE: PRT
<213> ORGANISM: Homo sapiens

<400> SEQUENCE: 9

```
Ala Asp Pro Cys Asp Ser Asn Pro Arg Gly Val Ser Ala Tyr Leu Ser
1               5                   10                  15

Arg Pro Ser Pro Phe Asp Leu Phe Ile Arg Lys Ser Pro Thr Ile Thr
            20                  25                  30

Cys Leu Val Val Asp Leu Ala Pro Ser Lys Gly Thr Val Asn Leu Thr
        35                  40                  45

Trp Ser Arg Ala Ser Gly Lys Pro Val Asn His Ser Thr Arg Lys Glu
    50                  55                  60

Glu Lys Gln Arg Asn Gly Thr Leu Thr Val Thr Ser Thr Leu Pro Val
65                  70                  75                  80

Gly Thr Arg Asp Trp Ile Glu Gly Glu Thr Tyr Gln Cys Arg Val Thr
                85                  90                  95

His Pro His Leu Pro Arg Ala Leu Met Arg Ser Thr Thr Lys Thr Ser
            100                 105                 110

Gly Pro Arg Ala Ala Pro Glu Val Tyr Ala Phe Ala Thr Pro Glu Trp
        115                 120                 125

Pro Gly Ser Arg Asp Lys Arg Thr Leu Ala Cys Leu Ile Gln Asn Phe
    130                 135                 140

Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
                165                 170                 175

Gly Phe Phe Val Phe Ser Arg Leu Glu Val Thr Arg Ala Glu Trp Glu
            180                 185                 190

Gln Lys Asp Glu Phe Ile Cys Arg Ala Val His Glu Ala Ala Ser Pro
        195                 200                 205

Ser Gln Thr Val Gln Arg Ala Val Ser Val Asn Pro Gly Lys
    210                 215                 220
```

<210> SEQ ID NO 10
<211> LENGTH: 327
<212> TYPE: PRT
<213> ORGANISM: Homo sapiens

<400> SEQUENCE: 10

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 11
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 11

Cys Pro Glu Pro Lys Ser Cys Asp Thr Pro Pro Cys Pro Arg
1               5                   10                  15

<210> SEQ ID NO 12
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 12

Glu Leu Lys Thr Pro Leu Gly Asp Thr Thr His Thr
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 13
```

```
Lys Ser Cys Asp Lys Thr His Thr Cys Pro
1               5                   10

<210> SEQ ID NO 14
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 14

Lys Cys Cys Val Asp Cys Pro
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 15

Lys Tyr Gly Pro Pro Cys Pro
1               5

<210> SEQ ID NO 16
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 16

Met Tyr Arg Met Gln Leu Leu Ser Cys Ile Ala Leu Ser Leu Ala Leu
1               5                   10                  15

Val Thr Asn Ser
            20

<210> SEQ ID NO 17
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 17

Met Gly Val Lys Val Leu Phe Ala Leu Ile Cys Ile Ala Val Ala Glu
1               5                   10                  15

Ala

<210> SEQ ID NO 18
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 18

Met Lys Trp Val Thr Phe Ile Ser Leu Leu Phe Leu Phe Ser Ser Ala
1               5                   10                  15

Tyr Ser

<210> SEQ ID NO 19
<211> LENGTH: 18
<212> TYPE: PRT
```

```
<213> ORGANISM: Artificial sequence
<220> FEATURE:
<223> OTHER INFORMATION: Synthetic amino acid sequence

<400> SEQUENCE: 19

Met Ala Phe Leu Trp Leu Leu Ser Cys Trp Ala Leu Leu Gly Thr Thr
1               5                   10                  15

Phe Gly

<210> SEQ ID NO 20
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 20

Met Asn Leu Leu Leu Ile Leu Thr Phe Val Ala Ala Ala Val Ala
1               5                   10                  15

<210> SEQ ID NO 21
<211> LENGTH: 60
<212> TYPE: DNA
<213> ORGANISM: Artificial sequence
<220> FEATURE:
<223> OTHER INFORMATION: Synthetic nucleic acid sequence

<400> SEQUENCE: 21
gcactaagtc ttgcacttgt cacgaattcg gcaaagacca tggttagatc tgacaaaact     60

<210> SEQ ID NO 22
<211> LENGTH: 60
<212> TYPE: DNA
<213> ORGANISM: Artificial sequence
<220> FEATURE:
<223> OTHER INFORMATION: Synthetic nucleic acid sequence

<400> SEQUENCE: 22
atgtgtgagt tttgtcagat ctaaccatgg tctttgccga attcgtgaca agtgcaagac     60

<210> SEQ ID NO 23
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 23
tgtcacgaat tcggcaaaga ccacggttag atctga                               36

<210> SEQ ID NO 24
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 24
agttttgtca gatctaaccg tggtctttgc cgaattc                              37

<210> SEQ ID NO 25
<211> LENGTH: 20
<212> TYPE: DNA
<213> ORGANISM: Artificial sequence
<220> FEATURE:
<223> OTHER INFORMATION: Synthetic nucleic acid sequence
```

<400> SEQUENCE: 25
tgcttgctca actctacgtc                                                  20

<210> SEQ ID NO 26
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 26
ttgcagctta taatggttac aaa                                              23

<210> SEQ ID NO 27
<211> LENGTH: 41
<212> TYPE: DNA
<213> ORGANISM: Artificial sequence
<220> FEATURE:
<223> OTHER INFORMATION: Synthetic nucleic acid sequence

<400> SEQUENCE: 27
atctaactgc tgcgccgccg ggaaaatact gtacggttag a                          41

<210> SEQ ID NO 28
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 28
aggaggatag ttcggtggct gttcagggtc tcctcct                               37

<210> SEQ ID NO 29
<211> LENGTH: 41
<212> TYPE: DNA
<213> ORGANISM: Artificial sequence
<220> FEATURE:
<223> OTHER INFORMATION: Synthetic nucleic acid sequence

<400> SEQUENCE: 29
ccctagagtg agtcgtatga ccctagagtg agtcgtatga a                          41

<210> SEQ ID NO 30
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 30 acctttttttt acattgaagt gcag                                            24

<210> SEQ ID NO 31
<211> LENGTH: 42
<212> TYPE: DNA
<213> ORGANISM: Artificial sequence
<220> FEATURE:
<223> OTHER INFORMATION: Synthetic nucleic acid sequence

<400> SEQUENCE: 31
ctgcacttca atgtaaaaaa aggtcaccat gtacaggatg ca                         42

<210> SEQ ID NO 32

<210> SEQ ID NO 32
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 32
gcaatgcaag acaggagttg catcctgtac atggtg                                36

<210> SEQ ID NO 33
<211> LENGTH: 38
<212> TYPE: DNA
<213> ORGANISM: Artificial sequence
<220> FEATURE:
<223> OTHER INFORMATION: Synthetic nucleic acid sequence

<400> SEQUENCE: 33
actcctgtct tgcattgcac taagtcttgc acttgtca                              38

<210> SEQ ID NO 34
<211> LENGTH: 39
<212> TYPE: DNA
<213> ORGANISM: Artificial sequence
<220> FEATURE:
<223> OTHER INFORMATION: Synthetic nucleic acid sequence

<400> SEQUENCE: 34
tcagtcttag ccgaattcgt gacaagtgca agacttagt                             39

<210> SEQ ID NO 35
<211> LENGTH: 39
<212> TYPE: DNA
<213> ORGANISM: Artificial sequence
<220> FEATURE:
<223> OTHER INFORMATION: Synthetic nucleic acid sequence

<400> SEQUENCE: 35
cgaattcggc taagactgac atccaaatga ctcagagcc                             39

<210> SEQ ID NO 36
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 36
gcgctcaggg aactggggct ctgagtcatt tggatg                                36

<210> SEQ ID NO 37
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 37
ccagttccct gagcgcttcc gtaggggaca gg                                    32

<210> SEQ ID NO 38
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 38
gcccgacatg ttattgtcac cctgtcccct acggaa                                36

<210> SEQ ID NO 39
<211> LENGTH: 40
<212> TYPE: DNA
<213> ORGANISM: Artificial sequence
<220> FEATURE:
<223> OTHER INFORMATION: Synthetic nucleic acid sequence

<400> SEQUENCE: 39
gtgacaataa catgtcgggc tagccaggat gtcaatacag                            40

<210> SEQ ID NO 40
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 40
ctggtaccaa gcgacagctg tattgacatc ctggcta                               37

<210> SEQ ID NO 41
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 41
ctgtcgcttg gtaccagcaa aagcccggaa aggc                                  34

<210> SEQ ID NO 42
<211> LENGTH: 39
<212> TYPE: DNA
<213> ORGANISM: Artificial sequence
<220> FEATURE:
<223> OTHER INFORMATION: Synthetic nucleic acid sequence

<400> SEQUENCE: 42
gctgtatata agaagctttg gcgcctttcc gggcttttg                             39

<210> SEQ ID NO 43
<211> LENGTH: 42
<212> TYPE: DNA
<213> ORGANISM: Artificial sequence
<220> FEATURE:
<223> OTHER INFORMATION: Synthetic nucleic acid sequence

<400> SEQUENCE: 43
gccaaagctt cttatataca gcgccagttt cctctattct gg                         42

<210> SEQ ID NO 44
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 44
gaacctgctc ggcacgccag aatagaggaa actggc                                36

<210> SEQ ID NO 45
<211> LENGTH: 32
<212> TYPE: DNA

<213> ORGANISM: Artificial sequence
<220> FEATURE:
<223> OTHER INFORMATION: Synthetic nucleic acid sequence

<400> SEQUENCE: 45
cgtgccgagc aggttctctg gatctcggtc cg                               32

<210> SEQ ID NO 46
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 46
tcagtgtgaa atcggtcccg gaccgagatc caga                             34

<210> SEQ ID NO 47
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 47
ggaccgattt cacactgacc attagttctc tgcagcc                          37

<210> SEQ ID NO 48
<211> LENGTH: 40
<212> TYPE: DNA
<213> ORGANISM: Artificial sequence
<220> FEATURE:
<223> OTHER INFORMATION: Synthetic nucleic acid sequence

<400> SEQUENCE: 48
tagtatgttg caaagtcctc tggctgcaga gaactaatgg                       40

<210> SEQ ID NO 49
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 49
agaggacttt gcaacatact actgccagca gcactat                          37

<210> SEQ ID NO 50
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 50
aggttggggg tgtggtatag tgctgctggc ag                               32

<210> SEQ ID NO 51
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 51
accacacccc caacctttgg tcagggcacg aa                               32

<210> SEQ ID NO 52
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 52
cgtacgcttg atttccacct tcgtgccctg accaa                          35

<210> SEQ ID NO 53
<211> LENGTH: 39
<212> TYPE: DNA
<213> ORGANISM: Artificial sequence
<220> FEATURE:
<223> OTHER INFORMATION: Synthetic nucleic acid sequence

<400> SEQUENCE: 53
ggtggaaatc aagcgtacga aaaaacccc caactttgt                       39

<210> SEQ ID NO 54
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 54
acaaagttgg gggttttttt                                           20

<210> SEQ ID NO 55
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 55
tttttttctt agctgctttg a                                         21

<210> SEQ ID NO 56
<211> LENGTH: 38
<212> TYPE: DNA
<213> ORGANISM: Artificial sequence
<220> FEATURE:
<223> OTHER INFORMATION: Synthetic nucleic acid sequence

<400> SEQUENCE: 56
tcaaagcagc taagaaaaaa agaattcgct ccaaacag                       38

<210> SEQ ID NO 57
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 57
cgacgagttg gacttctgtt tggagcgaat tc                             32

<210> SEQ ID NO 58
<211> LENGTH: 29
<212> TYPE: DNA
<213> ORGANISM: Artificial sequence
<220> FEATURE:

<223> OTHER INFORMATION: Synthetic nucleic acid sequence

<400> SEQUENCE: 58
aagtccaact cgtcgaaagc ggaggtggc                                    29

<210> SEQ ID NO 59
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 59
ccaggctgaa ccaggccacc tccgcttt                                     28

<210> SEQ ID NO 60
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 60
ctggttcagc ctggcggaag cctgcgc                                      27

<210> SEQ ID NO 61
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 61
gcagcacagc tcaagcgcag gcttccg                                      27

<210> SEQ ID NO 62
<211> LENGTH: 35
<212> TYPE: DNA
<213> ORGANISM: Artificial sequence
<220> FEATURE:
<223> OTHER INFORMATION: Synthetic nucleic acid sequence

<400> SEQUENCE: 62
ttgagctgtg ctgcctccgg atttaatatc aaaga                             35

<210> SEQ ID NO 63
<211> LENGTH: 42
<212> TYPE: DNA
<213> ORGANISM: Artificial sequence
<220> FEATURE:
<223> OTHER INFORMATION: Synthetic nucleic acid sequence

<400> SEQUENCE: 63
cgaacccagt gtatataagt atctttgata ttaaatccgg ag                     42

<210> SEQ ID NO 64
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 64
tacttatata cactgggttc gccaggctcc tgga                              34

```
<210> SEQ ID NO 65
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 65
ccactccaga ccctttccag gagcctgg                                              28

<210> SEQ ID NO 66
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 66
aagggtctgg agtgggtggc gagaatctac c                                          31

<210> SEQ ID NO 67
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 67
gggtataacc attggttggg tagattctcg ccac                                       34

<210> SEQ ID NO 68
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 68
caaccaatgg ttatacccgc tatgcagaca gcg                                        33

<210> SEQ ID NO 69
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 69
gtaaaccgcc ctttcacgct gtctgcatag c                                          31

<210> SEQ ID NO 70
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 70
tgaaagggcg gtttacaatt agtgccgaca ca                                         32

<210> SEQ ID NO 71
<211> LENGTH: 35
<212> TYPE: DNA
<213> ORGANISM: Artificial sequence
<220> FEATURE:
<223> OTHER INFORMATION: Synthetic nucleic acid sequence
```

```
<400> SEQUENCE: 71
ggtaagcggt atttttagat gtgtcggcac taatt                              35

<210> SEQ ID NO 72
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 72
tctaaaaata ccgcttacct ccagatgaac tctctg                             36

<210> SEQ ID NO 73
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 73
tgtcctcggc cctcagagag ttcatctgga                                    30

<210> SEQ ID NO 74
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 74
agggccgagg acacggctgt gtattattgc                                    30

<210> SEQ ID NO 75
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 75
caccccaccg gctgcaataa tacacagccg                                    30

<210> SEQ ID NO 76
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 76
agccggtggg gtggagacgg attctatgct                                    30

<210> SEQ ID NO 77
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 77
tgaccccaat agtccatagc atagaatccg tctc                               34

<210> SEQ ID NO 78
<211> LENGTH: 31
```

<212> TYPE: DNA
<213> ORGANISM: Artificial sequence
<220> FEATURE:
<223> OTHER INFORMATION: Synthetic nucleic acid sequence

<400> SEQUENCE: 78
atggactatt ggggtcaggg cactctcgtc a                                    31

<210> SEQ ID NO 79
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 79
tggcactgct tacagtgacg agagtgccc                                       29

<210> SEQ ID NO 80
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 80
ctgtaagcag tgccagcaca aaggggcc                                        28

<210> SEQ ID NO 81
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 81 caagggaaa gacactaggc ccctttgtgc                                       30

<210> SEQ ID NO 82
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 82
tagtgtcttt ccccttgctc catctagcaa atctac                               36

<210> SEQ ID NO 83
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 83
ggtgcccccg ctggtagatt tgctagatgg ag                                   32

<210> SEQ ID NO 84
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 84
cagcgggggc accgccgccc tgggat 26

<210> SEQ ID NO 85
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 85
gtccttgacc aggcatccca gggcggc 27

<210> SEQ ID NO 86
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 86
gcctggtcaa ggactatttt cctgagccag t 31

<210> SEQ ID NO 87
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 87
tccaggacac ggtgactggc tcaggaaaat a 31

<210> SEQ ID NO 88
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 88
caccgtgtcc tggaatagtg gcgccttga 29

<210> SEQ ID NO 89
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 89
tgtgtgaaca ccagaagtca aggcgccact at 32

<210> SEQ ID NO 90
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 90
cttctggtgt tcacacattt cccgccgtcc 30

<210> SEQ ID NO 91
<211> LENGTH: 30
<212> TYPE: DNA
<213> ORGANISM: Artificial sequence

```
<220> FEATURE:
<223> OTHER INFORMATION: Synthetic nucleic acid sequence

<400> SEQUENCE: 91
cagcccacta gattgaagga cggcgggaaa                                        30

<210> SEQ ID NO 92
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 92
ttcaatctag tgggctgtac tctctctcca gtgt                                   34

<210> SEQ ID NO 93
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 93
tgggtaccgt caccacactg gagagagagt a                                      31

<210> SEQ ID NO 94
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 94
ggtgacggta cccagttcaa gcttgggca                                         29

<210> SEQ ID NO 95
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 95
tgcagatata ggtctgtgtg cccaagcttg aac                                    33

<210> SEQ ID NO 96
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 96
cacagaccta tatctgcaat gtgaaccaca agcc                                   34

<210> SEQ ID NO 97
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 97
ccacctttgt attgctgggc ttgtggttca cat                                    33
```

<210> SEQ ID NO 98
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 98
cagcaataca aaggtggaca aaaaagtcga gcct                          34

<210> SEQ ID NO 99
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 99
tgtcacagct ctttggaggc tcgactttt tgt                            33

<210> SEQ ID NO 100
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 100
ccaaagagct gtgacaaaac tcacacatgc cc                            32

<210> SEQ ID NO 101
<211> LENGTH: 30
<212> TYPE: DNA
<213> ORGANISM: Artificial sequence
<220> FEATURE:
<223> OTHER INFORMATION: Synthetic nucleic acid sequence

<400> SEQUENCE: 101
tacctgggca cggtgggcat gtgtgagttt                               30

<210> SEQ ID NO 102
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 102
accgtgccca ggtaagccag cccaggc                                  27

<210> SEQ ID NO 103
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 103
ccccattgac ttttttttag gcctgggctg gct                           33

<210> SEQ ID NO 104
<211> LENGTH: 20
<212> TYPE: DNA
<213> ORGANISM: Artificial sequence
<220> FEATURE:
<223> OTHER INFORMATION: Synthetic nucleic acid sequence

```
<400> SEQUENCE: 104
ctaaaaaaaa gtcaatgggg                                                20

<210> SEQ ID NO 105
<211> LENGTH: 36
<212> TYPE: DNA
<213> ORGANISM: Artificial sequence
<220> FEATURE:
<223> OTHER INFORMATION: Synthetic nucleic acid sequence

<400> SEQUENCE: 105
tttttttaga tctctttgga ggctcgactt ttttgt                              36
```

MODIFIED FC POLYPEPTIDES, FC CONJUGATES, AND METHODS OF USE THEREOF

CROSS-REFERENCE

This application claims the benefit of U.S. Provisional Patent Application No. 61/704,166, filed Sep. 21, 2012, and U.S. Provisional Patent Application No. 61/711,589, filed Oct. 9, 2012, which applications are incorporated herein by reference in their entirety.

BACKGROUND

Generation of fusion proteins comprising segments derived from two or more different precursor proteins has represented an important advance in the field of protein engineering. Fusion proteins allow multiple biological functions, such as binding and therapeutic activity, to be combined in a single entity.

The crystallizable fragment (Fc) of an immunoglobulin molecule binds to Fc receptors and/or complement proteins. The Fc domain mediates various physiological effects including lysis of target cells.

There is a need in the field for methods of a conjugating functional group to the Fc domain of an immunoglobulin.

LITERATURE

Gilmore et al. (2006) *Angew. Chem. Int. Ed.* 45:5307; Scheck et al. (2007) *ACS Chem. Biol.* 2:247; Scheck et al. (2008) *J. Am. Chem. Soc.* 130:11762; Witus et al. (2010) *J. Am. Chem. Soc.* 132:16812.

SUMMARY

The present disclosure provides modified Fc domains having one or more attachment moieties for attaching a heterologous functional moiety; and methods of generating the modified Fc domains. The present disclosure provides Fc conjugates; and methods of making the conjugates. The Fc conjugates are useful in various methods, which are also provided.

BRIEF DESCRIPTION OF THE DRAWINGS

FIGS. 1A-C depict the structure and an expression vector for Fc of human IgG1. FIG. 1C depicts the nucleotide (SEQ ID NO:1) and amino acid (SEQ ID NO:2) sequences of an exemplary Fc.

FIGS. 10A-C provide amino acid sequences of immunoglobulin Fc domains.

FIGS. 11A and 11B depict functionalization of anti-HER2 human IgG1 antibodies with DNA aptamers both through N-terminal modification and through lysine modification.

FIGS. 12A and 12B depict the binding specificity of antibody-DNA aptamer conjugates.

FIGS. 13A-C provide amino acid sequences (FIG. 13C) of anti-HER2 heavy and light chains and nucleotide sequences (FIGS. 13A and 13B) encoding same.

DEFINITIONS

Figure 1A:
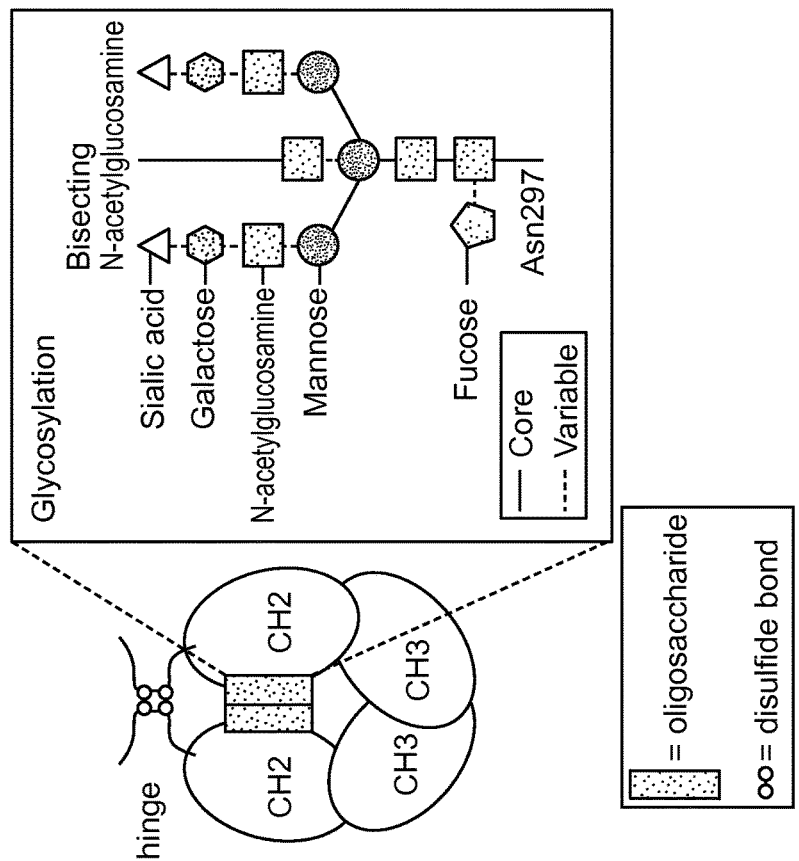

"ADCC" or "antibody dependent cell-mediated cytotoxicity," as used herein, refers to a cell-mediated reaction in which nonspecific cytotoxic cells that express Fcγ receptors (FcγRs) recognize bound antibody on a target cell and subsequently cause lysis of the target cell.

"ADCP" or "antibody dependent cell-mediated phagocytosis," as used herein, refers to a cell-mediated reaction in which nonspecific cytotoxic cells that express FcγRs recognize bound antibody on a target cell and subsequently cause phagocytosis of the target cell.

"CDC" or "complement-dependent cytotoxicity," as used herein, refers to a reaction initiated by multiple Fc-domains interacting with C1q, which can ultimately result in one or more of lysis of a target cell through the formation of the membrane attack complex (MAC), phagocyte recruitment, and opsonization of a target.

A modified Fc polypeptide of the present disclosure, or an Fc conjugate of the present disclosure, can specifically bind to an Fc receptor. By "specifically bind" is meant that the modified Fc polypeptide or the Fc conjugate binds an Fc receptor with an affinity in the range of from about $10^{-6}$ M to about $10^{-7}$M, from about $10^{-7}$ M to about $10^{-8}$ M, or from about $10^{-8}$ M to about $10^{-9}$ M, or greater than $10^{-9}$ M. In some cases, a modified Fc polypeptide, or an Fc conjugate, binds an Fc receptor with an affinity of less than $10^{-6}$M.

Fc receptors are known in the art, and are classified based on the isotype of the Fc that they bind. Fc receptors include neonatal Fc receptor (FcRn), Fcγ receptors (FcγR), an Fcα receptor (FcαR), Fcε receptors (FcεR), and Fcα/µ receptor (Fcα/µR). FcγRs bind IgG isotype Fc domains and include FcγRI (CD64), FcγRIIA (CD32), FcγRIIB (CD32), FcγRIIIA (CD16a), and FcγRIIIB (CD16b). Binding of an IgG isotype Fc domain (Fcγ) to an FcγR can result in phagocytosis, ADCC, and the like. The Fcα receptor (FcαRI) binds IgA Fc domains, and is found on the surface of neutrophils, eosinophils, monocytes, some macrophages (including Kupffer cells), and some dendritic cells. Binding of an IgA Fc domain (Fcα) to an FcαR can result in phagocytosis or induction of microbe killing FceRs bind IgE Fc domains, and include the high-affinity FcεRI, found on epidermal Langerhans cells, eosinophils, mast cells and basophils; and the low-affinity FcεRII (CD23). Binding of an IgE isotype Fc domain (Fcε) to an FcεR (e.g., FcεRI) can result in degranulation. Fcα/µR binds IgA Fc domains and IgM Fc domains, and is found on B cells, mesangial cells, and macrophages.

By "effector function" as used herein is meant a biochemical event that results from the interaction of an antibody Fc region ("an Fc domain") with an Fc receptor or ligand. Effector functions include but are not limited to ADCC, ADCP, and complement-dependent cytotoxicity (CDC). By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans cells, natural killer (NK) cells, and cytotoxic T cells.

By "Fc", "Fc region," Fc polypeptide," "Fc domain," etc. as used herein is meant a polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, the Fc domain comprises immunoglobulin domains Cγ2 and Cγ3 (CH2 and CH3) and the hinge between Cγ1 (CH1) and Cγ2 (CH2). Although the boundaries of the Fc region may vary, the human IgG heavy chain Fc region is usually defined to comprise residues C226 or P230 to its carboxyl-terminus, wherein the numbering is according to the EU index as in Kabat. "Fc" can refer to the Fc domain in isolation, or the Fc region in the context of an antibody, antibody fragment, or Fc fusion. An Fc may be an antibody, Fc fusion, or an protein or protein domain that comprises Fc.

By "Fc ligand" as used herein is meant a factor (e.g., a polypeptide) that binds to the Fc region to form an Fc-ligand complex. Fc ligands include but are not limited to Fc receptors, C1q, C3, mannan binding lectin, mannose receptor, staphylococcal protein A, streptococcal protein G, and viral FcγR.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an Fc polypeptide" includes a plurality of such polypeptide and reference to "the attachment moiety" includes reference to one or more attachment moieties and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides modified Fc domains having one or more attachment moieties for attaching a heterologous functional moiety; and methods of generating the modified Fc domains. The present disclosure provides Fc conjugates; and methods of making the conjugates. The Fc conjugates are useful in various methods, which are also provided.

Modified Fc Polypeptides

The present disclosure provides a modified Fc polypeptide comprising one or more attachment moieties for attaching a heterologous functional moiety.

In some cases, a modified Fc polypeptide comprises a single (no more than one) attachment moiety for attaching a heterologous functional moiety. In other cases, a modified Fc polypeptide comprises 2, 3, 4, or 5 attachment moieties.

As used herein, the term "attachment moiety" refers to a moiety that is capable of reacting directly either spontaneously or after activation, with an accessible functional group of a heterologous functional moiety under aqueous conditions to produce a covalent linkage to the modified Fc polypeptide. The attachment moiety is capable of reacting under aqueous conditions at which Fc polypeptides of interest are able to be maintained in a folded state (e.g., physiological conditions).

The attachment moiety may include a first functional group that is reactive with a second functional group of the heterologous functional moiety and conjugates the attachment moiety and the heterologous functional moiety. Any suitable first and second functional groups and conjugation chemistries may find use in the subject modified Fc polypeptides and Fc conjugates, and methods for making the same. In some cases the first functional group includes an aldehyde or a ketone group. In other cases, the first functional group includes an aryl amino group (e.g., an aniline group or a aminophenol group). Further first and second functional groups of interest and methods of conjugating the same include but are not limited to those groups and methods described in Hermanson, "Bioconjugate Techniques" 2nd Edition, Academic Press, 2008.

As used herein, the terms "to crosslink" or "conjugate" are used interchangeably and refer to the process of linking two moieties or atoms to each other via a covalent bond. An exemplary cross-linking process is the reaction of a ketone group with a hydroxylamino group to produce a stable oxime covalent linkage.

In some instances, the modified Fc polypeptide is described by the structure of formula (I):

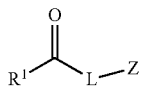

(I)

where $R^1$ is an amino acid sidechain, hydrogen, an alkyl or an aryl group, L is an optional linker and Z is an Fc polypeptide. In some embodiments, in formula (I), $R^1$ is methyl, L is a carbonyl group (—C(=O)—), and Z is an Fc polypeptide. In certain embodiments, $R^1$ is the amino acid sidechain of alanine or glutamic acid.

In some embodiments, the modified Fc polypeptide is described by the structure of formula (II):

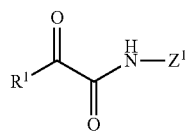

(II)

where $R^1$ is as described for formula (I), and $Z^1$ is an Fc polypeptide. In some embodiments, $Z^1$ includes N-terminal lysine-threonine residues, and $R^1$ is the amino acid side chain of alanine or glutamic acid.

In other instances, the modified Fc polypeptide is described by the structure of formula (III):

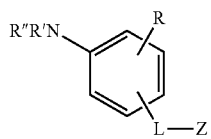

(III)

where R is one or more optional aryl substituents, R' and R" are each independently H, an alkyl or an aryl, L is a linker and Z is a Fc polypeptide. In some cases, each R substituent is independently selected from hydroxyl, alkyl, and aryl. In certain embodiments, R' and R" are each H. In some cases, the modified Fc polypeptide includes an aminophenol group. In certain cases, R is a hydroxyl substituent that is located at a position para to L, and L is located at a position meta to the amino group. In other cases, R is absent, and L is attached at the para position to the amino group.

In some embodiments, the modified Fc polypeptide is described by the structure:

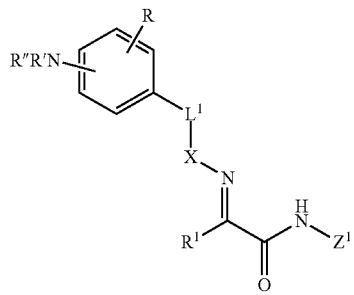

where $L^1$ is a linker, X is O or NH, R' and R" are each independently H, an alkyl or an aryl, R is one or more groups, independently selected from hydrogen, an alkyl, an aryl, a hydroxy, an alkoxy, an aryloxy, a heterocycle, a cyano, a halogen, an amino, an acyl, an acyloxy, an amido and nitro; $R^1$ is the sidechain of an amino acid, H, an alkyl or an aryl; and $Z^1$ is an Fc polypeptide. In certain embodiments, R' and R" are each H. In certain embodiments, $L^1$ is —$(CH_2)_m$—NHCO—$CH_2$— and X is O or NH, where m is 0, 1, 2, 3, 4, 5 or 6. In some embodiments, $L^1$ is —$(CH_2)_m$—NHCO— and X is NH, where m is 0, 1, 2, 3, 4, 5 or 6. In certain embodiments, $L^1$ is —$(CH_2)_m$—CONH—$CH_2$— and X is O or NH, where m is 0, 1, 2, 3, 4, 5 or 6. In certain embodiments, $L^1$ is —$(CH_2)_m$—CONH— and X is O or NH, where m is 0, 1, 2, 3, 4, 5 or 6.

In some embodiments, the modified Fc polypeptide is described by the structure of formula (IV):

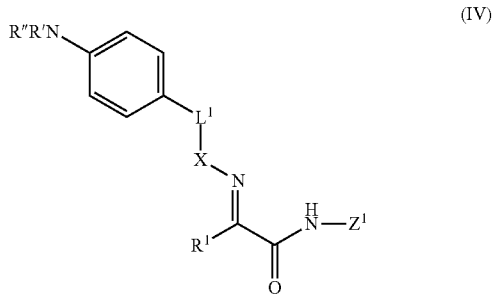

(IV)

where $L^1$ is a linker, X is O or NH, R' and R" are each independently H, an alkyl or an aryl and $R^1$ and $Z^1$ are as defined above in formula (II). In certain embodiments, R' and R" are each H. In certain embodiments, $L^1$ is —$(CH_2)_m$—NHCO—$CH_2$— and X is O, where m is 0, 1, 2, 3, 4, 5 or 6. In some embodiments, $L^1$ is —$(CH_2)_m$—NHCO— and X is NH, where m is 0, 1, 2, 3, 4, 5 or 6. In certain embodiments, m is 1 or 2. In certain embodiments, $L^1$ is —$(CH_2)_m$—CONH—$CH_2$— and X is O or NH, where m is 0, 1, 2, 3, 4, 5 or 6. In certain embodiments, L' is —$(CH_2)_m$—CONH— and X is O or NH, where m is 0, 1, 2, 3, 4, 5 or 6.

In certain embodiments, the modified Fc polypeptide is described by the structure of formula (V):

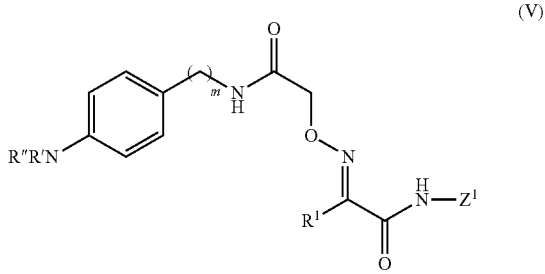

(V)

where m is 1 or 2, R' and R" are each independently H, an alkyl or an aryl, and $R^1$ and $Z^1$ are as described in formula (II). In certain embodiments, R' and R" are each H. In certain embodiments, $R^1$ is a lower alkyl (e.g., methyl). In certain embodiments, $Z^1$ is a Fc polypeptide that includes N-terminal lysine-threonine residues, and $R^1$ is the amino acid side chain of alanine.

As used herein, the term "linker" or "linkage" refers to a linking moiety that connects two groups and has a backbone. In some cases, the backbone of the linker is 100 atoms or less in length, such as 50 atoms or less, or 20 atoms or less in length. In other cases, the backbone of the linker is 100 atoms or greater in length. A linker or linkage may be a covalent bond that connects two groups or a chain of between 1 and 100 atoms in length, such as between 1 and 50 atoms in length or 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be peptidic or non-peptidic. A linker may be cleavable or non-cleavable.

Fc Polypeptides

Fc polypeptides that can be modified to generate a subject modified Fc polypeptide include Fc polypeptides of any of a variety of species, including, e.g., human Fc polypeptide, mouse Fc polypeptides, rat Fc polypeptides, and the like. Fc polypeptides that can be modified to generate a subject modified Fc polypeptide include synthetic (non-naturally occurring) Fc polypeptides, e.g., Fc polypeptides comprising amino acid sequences not found in nature. Fc polypeptides that can be modified to generate a subject modified Fc polypeptide include Fcγ (including Fcγ1, Fcγ2, Fcγ3, Fcγ4), Fcδ, Fcμ, Fcα, and Fcε. In some cases, the Fc polypeptide is part of a longer polypeptide, e.g., in some embodiments, the Fc polypeptide is part of a full-length immunoglobulin polypeptide comprising an antigen-binding domain. Where the Fc polypeptide is part of a longer polypeptide, the attachment site can be the native N-terminal amino acid of the longer polypeptide, or the N-terminal amino acid of the longer polypeptide can be mutated, as described herein.

An Fc polypeptide that is modified to comprise one or more attachment moieties for attaching a heterologous functional moiety may be referred to herein as a "parent" Fc polypeptide.

Generally, an Fc polypeptide that is suitable for modification to generate a subject modified Fc polypeptide is an Fc polypeptide that can bind an Fc receptor.

In some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (e.g., 212 amino acids, 227 amino acids, 234 amino acids, or 238 amino acids; or from about 200 amino acids (aa) to about 210 aa, from about 210 aa to about 220 aa, from about 220 aa to about 225 aa, from about 225 aa to about 230 aa, from about 230 aa to about 240 aa, from about 240 aa to about 250 aa, or from about 250 aa to about 276 aa) of one of the amino acid sequences depicted in FIGS. 10A-C.

For example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, from about 210 aa to about 220 aa, from about 220 aa to about 225 aa, or from about 225 aa to about 227 aa) of the IgG1 Fc amino acid sequence set forth in SEQ ID NO:3 and depicted in FIG. 10A.

As another example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, from about 210 aa to about 220 aa, from about 220 aa to about 225 aa, or from about 225 aa to about 227 aa) of amino acids 99-325 of the IgG2 Fc amino acid sequence set forth in SEQ ID NO:4 and depicted in FIG. 10A.

As another example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, from about 210 aa to about 220 aa, from about 220 aa to about 225 aa, from about 225 aa to about 230 aa, or from about 230 aa to about 238 aa) of amino acids 19-246 of the IgG3 Fc amino acid sequence set forth in SEQ ID NO:5 and depicted in FIG. 10A.

As another example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, from about 210 aa to about 220 aa, from about 220 aa to about 222 aa) of amino acids 162-383 of the IgD Fc amino acid sequence set forth in SEQ ID NO:6 and depicted in FIG. 10B.

As another example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, from about 210 aa to about 220 aa, from about 220 aa to about 225 aa, from about 225 aa to about 230 aa, from about 230 aa to about 240 aa, from about 240 aa to about 250 aa, or from about 250 aa to about 276 aa) of the IgM Fc amino acid sequence set forth in SEQ ID NO:7 and depicted in FIG. 10B.

As another example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, from about 210 aa to about 220 aa, from about 220 aa to about 225 aa, from about 225 aa to about 230 aa, or from about 230 aa to about 234 aa) of amino acids 120-353 of the IgA Fc amino acid sequence set forth in SEQ ID NO:8 and depicted in FIG. 10C.

As another example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, or from about 210 aa to about 212 aa) of amino acids 6-222 of the IgE Fc amino acid sequence set forth in SEQ ID NO:9 and depicted in FIG. 10C.

As another example, in some cases, an Fc polypeptide that is suitable for modification to generate a subject modified Fc polypeptide comprises an amino acid sequence having at least about 80%, at least about 85%, at least about 90%, at least about 95%, at least about 98%, at least about 99%, or 100%, amino acid sequence identity to a contiguous stretch of at least about 200 amino acids (from about 200 aa to about 210 aa, or from about 210 aa to about 228 aa) of amino acids 100-327 of the IgG4 Fc amino acid sequence set forth in SEQ ID NO:10 and depicted in FIG. 10C.

Additional Sequences

In some cases, the parent Fc polypeptide is part of a larger polypeptide, e.g., the parent polypeptide comprising the parent Fc polypeptide, and also comprises additional (non-Fc) amino acid sequences.

In some cases, the parent Fc polypeptide includes one or more of: an antigen-binding region; a secretion signal sequence; a hinge sequence; a non-immunoglobulin sequence; and the like.

Antigen-Binding Region

As noted above, in some cases, the Fc polypeptide part of an immunoglobulin polypeptide comprising an antigen-binding domain and the Fc polypeptide. In these embodiments, the attachment site is at the N-terminus of the immunoglobulin polypeptide. Thus, for example the N-terminal amino acid can be the native N-terminal amino acid, or the native N-terminal amino acid can be mutated, as described herein.

An antigen-binding region can include VH and/or VL regions. VH and VL sequences are known in the art. An antigen-binding region can be an antibody fragment that retain specific binding to antigen, including, but not limited to, Fab, Fab', F(ab')$_2$, Fv, scFv, and Fd fragments. An antigen-binding region can be a single-chain Fv (scFv). An antigen-binding region can be a diabody.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab)$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains, which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); MacCallum et al., J. Mol. Biol. 262:732-745 (1996); and in "Antibody Engineering" (Springer Lab Manuals), Roland Kontermann and Stefan Duebel (2001), Chapter 21: "Protein sequence analysis and structure analysis of antibody variable domains" by Andrew Martin, pages 422-442, where the definitions include overlapping or subsets of amino acid residues when compared against each other. Nevertheless, application of any of these definitions to refer to a CDR of an antibody or grafted antibodies or variants thereof is intended to be within the scope of the term as defined and used herein. The amino acid residues which encompass the CDRs as defined by the above-cited Kabat, Chothia, and MacCallum references are set forth below in Table 1 as a comparison.

TABLE 1

CDR Definitions

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

Hinge Region

In some cases, the parent Fc polypeptide includes a hinge region, e.g., an immunoglobulin heavy chain hinge region, or other suitable spacer (also referred to herein as a "linker") Immunoglobulin hinge region amino acid sequences are known in the art; see, e.g., Tan et al. (1990) Proc. Natl. Acad. Sci. USA 87:162; and Huck et al. (1986) Nucl. Acids Res. 14:1779. As non-limiting examples, an immunoglobulin hinge region can include one of the following amino acid sequences: ISAM (as depicted in FIG. 1C); CPEPKSCDT-PPPCPR (SEQ ID NO:11) (see, e.g., Glaser et al. (2005) J. Biol. Chem. 280:41494); ELKTPLGDTTHT (SEQ ID NO:12); KSCDKTHTCP (SEQ ID NO:13); KCCVDCP (SEQ ID NO:14); KYGPPCP (SEQ ID NO:15); and the like.

A non-immunoglobulin linker peptide can be used. The linker peptide may have any of a variety of amino acid sequences. Proteins can be joined by a spacer peptide, generally of a flexible nature, although other chemical linkages are not excluded. A linker can be a peptide of between about 6 and about 40 amino acids in length, or between about 6 and about 25 amino acids in length. These linkers are generally produced by using synthetic, linker-encoding oligonucleotides to couple the proteins. Peptide linkers with a degree of flexibility will generally be preferred. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Secretion Signal Peptide

In some cases, the parent Fc polypeptide includes a secretion signal peptide, a variety of which are known in the art, which secretion signal peptide provides for secretion from a eukaryotic cell or a prokaryotic cell used to synthesize the parent Fc polypeptide.

Secretion signals that are suitable for use in bacteria include, but are not limited to, the secretion signal of Braun's lipoprotein of E. coli, S. marcescens, E. amylosora, M. morganii, and P. mirabilis, the TraT protein of E. coli and Salmonella; the penicillinase (PenP) protein of B. licheniformis and B. cereus and S. aureus; pullulanase proteins of Klebsiella pneumoniae and Klebsiella aerogenese; E. coli lipoproteins 1pp-28, Pal, Rp1A, Rp1B, OsmB, NIpB, and Orl17; chitobiase protein of V. harseyi; the β-1,4-endoglucanase protein of Pseudomonas solanacearum, the Pal and Pcp proteins of H. influenzae; the OprI protein of P. aeruginosa; the MalX and AmiA proteins of S. pneumoniae; the 34 kda antigen and TpmA protein of Treponema pallidum; the P37 protein of Mycoplasma hyorhinis; the neutral protease of Bacillus amyloliquefaciens; and the 17 kda antigen of Rickettsia rickettsii. Secretion signal sequences suitable for use in yeast are known in the art, and can be used. See, e.g., U.S. Pat. No. 5,712,113.

Secretion signals that are suitable for use in eukaryotic cells, e.g., mammalian cells, are known in the art. See, e.g., Notwehr and Gordon (1990) Bioessays 12:479; Choo et al. (2005) BMC Bioinformatics 6:249; Nielsen et al. (1997) Protein Engineering 10:1. A non-limiting example of a secretion signal sequence suitable for use in a mammalian cell includes, e.g., an IL2 signal sequence (e.g., MYRMQLLSCIALSLALVTNS (SEQ ID NO:16); as depicted in FIG. 1C). Other examples include, e.g., MGVK-VLFALICIAVAEA (SEQ ID NO:17); MKWVTFISLLFLF-SSAYS (SEQ ID NO:18); MAFLWLLSCWALLGTTFG (SEQ ID NO:19); and MNLLLILTFVAAAVA (SEQ ID NO:20).

Attachment Site

As noted above, a subject modified Fc polypeptide comprises one or more attachment moieties for attaching a heterologous functional moiety. In some embodiments, the attachment moiety is attached via the N-terminus of the Fc polypeptide. In other embodiments, the attachment moiety is attached via the side chain of a Lys residue at or near (e.g., within 1-5 amino acids of) the N-terminus of the Fc polypeptide. In other embodiments, the attachment moiety is attached via the side chain of a Lys residue at or near (e.g., within 1-5 amino acids of) the N-terminus of the Fc polypeptide, where the attachment is substantially selective for the Lys residue at or near the N-terminus of the Fc polypeptide (e.g., only one Lys residue, i.e., the Lys residue at or near the N-terminus of the Fc polypeptide, is modified with the attachment moiety). In other embodiments, the attachment moiety is attached via the side chain of a Lys residue at any position within the Fc polypeptide. Where the Fc polypeptide is part of a longer polypeptide, the attachment moiety is attached via the N-terminus of the longer polypeptide. For simplicity, the discussion below refers to the "N-terminal amino acid of the Fc polypeptide"; where the Fc polypeptide is part of a longer polypeptide, the "N-terminal amino acid of the Fc polypeptide" should be understood to refer to the N-terminal amino acid of the longer polypeptide. The N-terminal amino acid of the Fc polypeptide may be modified to install any suitable attachment moiety. In some cases, the amino acid sequence of an Fc polypeptide can be altered to include, at or near the N-terminus of the Fc polypeptide (e.g., at the first, second, or third N-terminal position), a positively charged and/or basic amino acid residue, including but not limited to, arginine or lysine. In other cases, the native N-terminal sequence of the Fc polypeptide is retained and attached to the attachment moiety. In certain cases, the amino acid sequence of an Fc polypeptide can be altered (e.g., by mutation) to include, at or near the N-terminus of the Fc polypeptide (e.g., at either the first or second position) an amino acid sequence that is selected to undergo an N-terminal modification reaction to install an attachment moiety. In some cases, one or more of the three N-terminal amino acid residues of an Fc polypeptide of interest are mutated to include one or more mutated amino acid residues that are desirable for modulating the installation of an attachment moiety. Any suitable mutated residues may be included at or near the N-terminal of an Fc polypeptide of interest. In other cases, the native Fc polypeptide N-terminal sequence includes desirable amino acid residues (e.g., any one of the mutated N-terminal sequences described herein) for installation of an attachment moiety.

In some embodiments, the N-terminus of the Fc polypeptide includes a three-residue sequence: $Xaa^1$-$Xaa^2$-$Xaa^3$, where $Xaa^1$ is alanine, glycine, aspartic acid, glutamic acid, asparagine, cysteine, arginine, threonine, tyrosine, leucine, or serine; wherein $Xaa^2$ and $Xaa^3$ are independently amino acid residues and at least one of $Xaa^2$ and $Xaa^3$ is a basic amino acid residue (e.g., lysine, arginine, or histidine). In certain embodiments, $Xaa^1$ is alanine or glutamic acid. In some cases, each of $Xaa^2$ and $Xaa^3$ is independently a basic amino acid (e.g., Lys, His, or Arg). In some cases, only one of $Xaa^2$ and $Xaa^3$ is a basic amino acid (e.g., Lys, His, or Arg). In some cases, both $Xaa^2$ and $Xaa^3$ are a basic amino acid (e.g., Lys, His, or Arg). In some cases, both of $Xaa^2$ and $Xaa^3$ are independently basic amino acid residues (e.g., Lys-Lys, Arg-Arg, Lys-Arg, Arg-Lys, Arg-His, Lys-His, His-His, His-Lys or His-Arg). Where both of $Xaa^2$ and $Xaa^3$ are independently basic amino acid residues (e.g., Lys-Lys, Arg-Arg, Lys-Arg, Arg-Lys, Arg-His, Lys-His, His-His, His-Lys or His-Arg), $Xaa^1$ is Ala. In some embodiments, one, two, or all three of $Xaa^1$, $Xaa^2$, and $Xaa^3$ is/are an acidic amino acid (e.g., Glu or Asp). For example, in some cases one of $Xaa^1$, $Xaa^2$, and $Xaa^3$ is an acidic amino acid (e.g., Glu or Asp); in other cases, two of $Xaa^1$, $Xaa^2$, and $Xaa^3$ are acidic amino acids (e.g., Glu or Asp); and in other instances, each of $Xaa^1$, $Xaa^2$, and $Xaa^3$ is an acidic amino acid (e.g., Glu or Asp), In some instances, the Fc polypeptide includes an N-terminal sequence selected from $Xaa^1$-Lys-$Xaa^3$, $Xaa^1$-Arg-$Xaa^3$, $Xaa^1$-$Xaa^2$-Lys and $Xaa^1$-$Xaa^2$-Arg, wherein $Xaa^1$ is Ala, and $Xaa^2$ and $Xaa^3$ are independently an amino acid residue. In some embodiments, the N-terminus of the Fc polypeptide includes an alanine-lysine-threonine (AKT) amino acid sequence, where the amino group of the terminus of the AKT sequence can be modified to install the attachment moiety. In some embodiments, the N-terminus of the Fc polypeptide includes an AKT amino acid sequence, where the epsilon amino group of the Lys can be modified to install the attachment moiety. In some embodiments, the N-terminus of the Fc polypeptide is mutated to include at least an alanine-lysine (AK) amino acid sequence. In certain embodiments, the N-terminus of the Fc polypeptide is mutated at least at the first position to include an alanine, glycine, aspartic acid, glutamic acid, asparagine, cysteine, arginine, threonine, tyrosine, leucine, or serine residue. In certain embodiments, the amino group of the N-terminus is modified to include a ketone or an aldehyde group via a transamination reaction.

As noted above, in some cases, one or both of $Xaa^2$ and $Xaa^3$ are independently basic amino acid residues (e.g., Lys-Lys, Arg-Arg, Lys-Arg, Arg-Lys, Arg-His, Lys-His, His-His, His-Lys or His-Arg), $Xaa^1$ is Ala. Where one or both of $Xaa^2$ and $Xaa^3$ are independently basic amino acid residues (e.g., Lys-Lys, Arg-Arg, Lys-Arg, Arg-Lys, Arg-His, Lys-His, His-His, His-Lys or His-Arg), $Xaa^1$ is Ala; and the transamination reaction to convert the N-terminal amino group to a ketone or aldehyde group is carried out with pyridoxal 5′-phosphate (PLP). As noted above, in some cases, one, two, or three of $Xaa^1$, $Xaa^2$, and $Xaa^3$ is an acidic amino acid (e.g., Glu or Asp). Where one, two, or three of $Xaa^1$, $Xaa^2$, and $Xaa^3$ is an acidic amino acid (e.g., Glu or Asp), the transamination reaction to convert the N-terminal amino group to a ketone or aldehyde group is carried out with Rapoport's Salt (e.g., N-methylpyridinium-4-carboxaldehyde or 4-Formyl-1-methylpyridinium salt).

Methods of Generating Modified Fc Polypeptides

Figure 2:
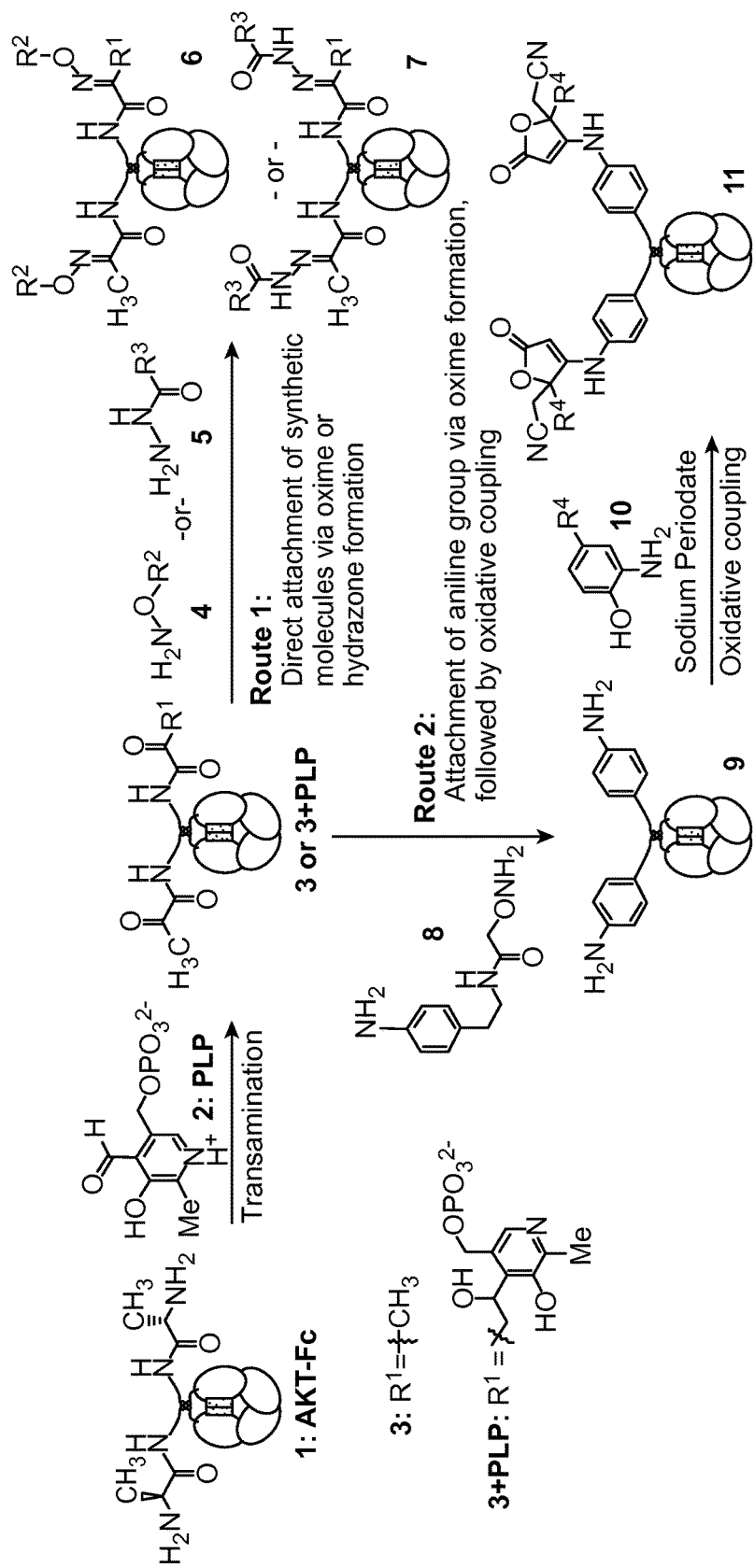
FIG. 2 presents modification schemes for Fc proteins.

The subject modified Fc domains may be prepared by using a variety of methods, the chemistry and steps of which are known to one of ordinary skill in the art. One exemplary method is illustrated in FIG. 2; however there are many other routes that would lead to the same molecule. In general terms, in the first step of the synthesis the N-terminal of a Fc domain of interest is mutated to include a sequence that is highly reactive to transamination reaction with an aldehyde. The N-terminal sequence of the Fc polypeptide may be selected to provide for a desired efficiency of transamination. For example, the N-terminal of the Fc polypeptide may be mutated to include alanine-lysine-threonine (AKT-Fc).

In the second step of the synthesis, the amino terminal of the Fc polypeptide undergoes a transamination reaction with an aldehyde reagent to convert the N-terminal amino group to a ketone or aldehyde group. Any convenient aldehyde reagent may be utilized in the subject methods. Reagents of interest include, but are not limited to, pyridoxal 5′-phosphate (PLP), Rapoport's Salt (e.g., N-methylpyridinium-4-carboxaldehyde or 4-Formyl-1-methylpyridinium salt), and those reagents described by Francis et al., *J. Am. Chem. Soc.* 2010, 132, 16812-16817 and Francis et al. *Angew. Chem. Int. Ed.* 2006, 45, 5307-5311, the disclosures of which are herein incorporated by reference in their entirety.

In an optional third step of the synthesis, the aldehyde or ketone group of the N-terminal residue of the modified Fc polypeptide may be covalently crosslinked with any convenient functional group and utilizing any convenient chemistry to install a further attachment moiety on the modified Fc polypeptide. In some embodiments, the aldehyde or ketone group is further derivatized to install a further attachment moiety, via an aldol reaction with a second aldehyde or ketone group, or via a coupling reaction with a hydroxylamino, a hydrazine or a hydrazido group. In such cases, the further attachment moiety may include an aryl amino group, such as an aniline group or an aminophenol group.

In certain embodiments, the aldehyde or ketone containing modified Fc polypeptide may be contacted with a bifunctional moiety including an aniline group linked to an aldehyde or ketone reactive group. In certain cases, the bifunctional moiety is described by the formula:

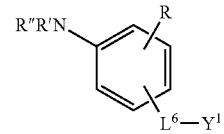

where R is one or more optional aryl substituents, R′ and R″ are each independently H, an alkyl or an aryl, $L^6$ is an optional linker and $Y^1$ is an aldehyde or ketone-reactive functional group. In certain embodiments, R′ and R″ are each H.

In certain embodiments, $Y^1$ is —CONHNH$_2$, —O—NH$_2$ or —NHNH$_2$. In certain embodiments, the bifunctional moiety is described by the formula:

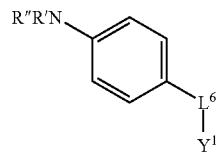

where R' and R" are each independently H, an alkyl or an aryl, $L^6$ is an optional linker and $Y^1$ is —CONHNH$_2$, —O—NH$_2$ or —NHNH$_2$. In certain embodiments, R' and R" are each H.

Fc Conjugates

The present disclosure provides Fc conjugates; compositions comprising the conjugates; and methods of making the conjugates. An Fc conjugate of the present disclosure comprises a subject modified Fc polypeptide and a covalently linked heterologous functional moiety.

A subject Fc conjugate retains the ability to bind one or more Fc ligands. For example, a subject Fc conjugate retains at least about 50%, at least about 60%, at least about 70%, at least about 80%, at least about 85%, at least about 90%, at least about 95%, at least about 98%, about 99%, or 100%, of the ability of the parent Fc polypeptide to bind an Fc ligand. For example, in some embodiments, a subject Fc conjugate retains the ability to bind an Fc receptor. In other embodiments, a subject Fc conjugate retains the ability to bind C1q.

A subject Fc conjugate retains at least one function of a parent Fc polypeptide. For example, a subject Fc conjugate retains at least about 50%, at least about 60%, at least about 70%, at least about 80%, at least about 85%, at least about 90%, at least about 95%, at least about 98%, about 99%, or 100%, of the function of a parent Fc polypeptide. For example, in some cases, a subject Fc conjugate retains activity in mediating or inducing an immune response to a target cell. For example, in some cases, a subject Fc conjugate retains activity in inducing cytolytic activity against a target cell. In other cases, a subject Fc conjugate retains activity in inducing phagocytosis of a target. In other instances, a subject Fc conjugate retains the ability to bind to FcRn.

In some embodiments, a subject Fc conjugate exhibits enhanced pharmacokinetic properties, relative to a parent Fc polypeptide used to generate the Fc conjugate.

In some embodiments, a subject Fc conjugate exhibits an increased serum half-life, compared to the serum half-life of the parent Fc polypeptide used to generate the Fc conjugate. For example, in some embodiments, a subject Fc conjugate has a serum half-life that is at least about 10%, at least about 15%, at least about 20%, at least about 25%, at least about 50%, at least about 75%, at least about 100% (or 2-fold), at least about 2.5-fold, at least about 5-fold, at least about 10-fold, or more than 10-fold, higher than the serum half-life of the parent Fc polypeptide used to generate the Fc conjugate. In some of these embodiments, a subject Fc conjugate exhibits an increased serum half-life by virtue of its ability to bind FcRn.

In some embodiments, a subject Fc conjugate exhibits an increased serum half-life, compared to the serum half-life (also referred to herein as "circulating half-life") of the heterologous functional moiety when not present in the Fc conjugate (e.g., compared to the free heterologous functional moiety not conjugated to an Fc polypeptide). For example, in some embodiments, a subject Fc conjugate has a serum half-life that is at least about 10%, at least about 15%, at least about 20%, at least about 25%, at least about 50%, at least about 75%, at least about 100% (or 2-fold), at least about 2.5-fold, at least about 5-fold, at least about 10-fold, or more than 10-fold, higher than the serum half-life of the unconjugated heterologous functional moiety. In some of these embodiments, a subject Fc conjugate exhibits an increased serum half-life by virtue of its ability to bind FcRn.

The present disclosure provides a method of increasing the serum half-life of a molecule (e.g., a functional moiety, as described herein). The method comprises conjugating the molecule to a modified Fc polypeptide of the present disclosure, thereby generating an Fc conjugate. The serum half-life of the Fc conjugate is greater than the serum half-life of the unconjugated molecule.

In some embodiments, the Fc conjugate is described by the structure of formula (VI):

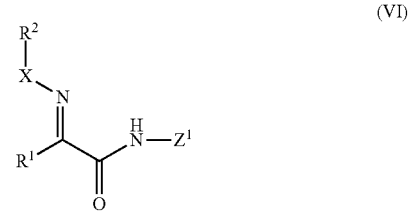

(VI)

where $R^1$ and $Z^1$ are as described above in formula (II), X is O or NH, and $R^2$ is $L^2$-$Z^2$, where $L^2$ is an optional linker and $Z^2$ is a heterologous functional moiety (e.g., as described below).

In some embodiments, in formula (VI), X is O such that the Fc polypeptide is crosslinked to the heterologous functional moiety via an oxime. In some embodiments, in formula (VI), X is NH such that the Fc polypeptide is crosslinked to the heterologous functional moiety via a hydrazone.

In some embodiments, the Fc conjugate is described by the structure of one of formulas (VII) and (VIII):

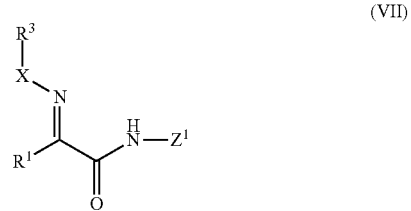

(VII)

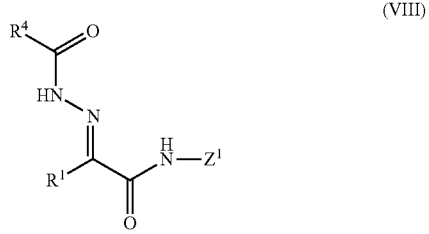

(VIII)

where $R^1$ and $Z^1$ are as described above in formula (II), X is O or NH, $R^3$ is $L^3$-$Z^2$, $R^4$ is $L^4$-$Z^2$, where $L^3$ and $L^4$ are optional linkers and $Z^2$ is a heterologous functional moiety (e.g., as described below).

In some embodiments, the Fc conjugate includes a linker having a structure derived from oxidative coupling of an aniline group and an aminophenol group (or alternative convenient oxidative coupling group). A number of linker structures are envisaged as products of the oxidative coupling of a modified Fc polypeptide (e.g., an aniline-containing modified Fc polypeptide) and a suitable heterologous functional moiety (e.g., aminophenol containing heterologous functional moiety). In some cases, the heterologous functional moiety includes a group suitable for oxidative coupling to the modified Fc polypeptide, including but not limited to, an aminophenol, a 2-methoxyphenol, an aniline, an azidophenol, and a phenylene diamine. Without wishing to be bound by theory, in certain embodiments, in formulas (VI), (VII) or (VIII), linker $L^2$, $L^3$ or $L^4$ includes a group described by one of the following structures:

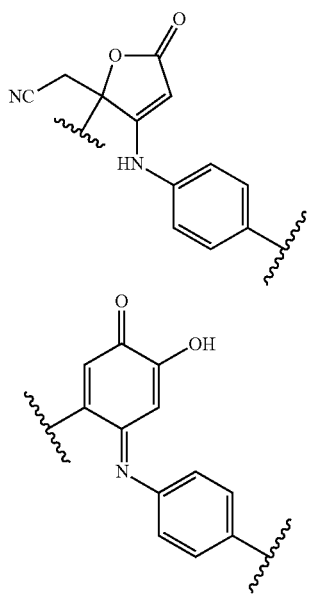

In some embodiments, in formulas (VII) or (VIII), $R^3$ and $R^4$ may include one of the following structures:

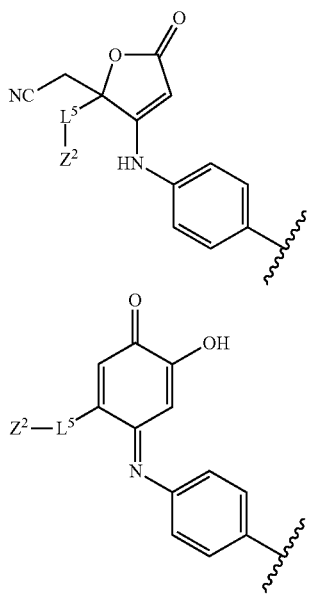

where $L^5$ is an optional linker and $Z^2$ is a heterologous functional moiety (e.g., as described below). $R^3$ and $R^4$ may further include a linker that connects the aniline group to the N-terminal of the Fc polypeptide (e.g., as described herein).

In some embodiments, the Fc conjugate includes one of the following structures:

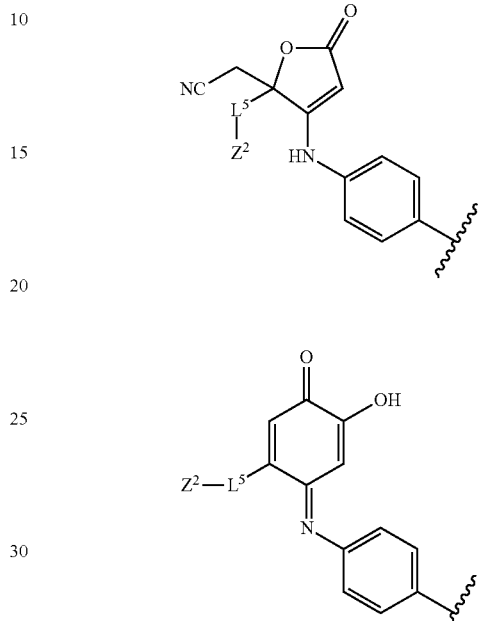

where $L^5$ is an optional linker and $Z^2$ is a heterologous functional moiety (e.g., as described below). The Fc conjugate may further include a linker that connects the aniline group to the N-terminal of the Fc polypeptide. Any convenient linker may be utilized to connect the aniline group and the Fc polypeptide.

In some embodiments, the Fc conjugate is described by one of the following structures:

(IXa)

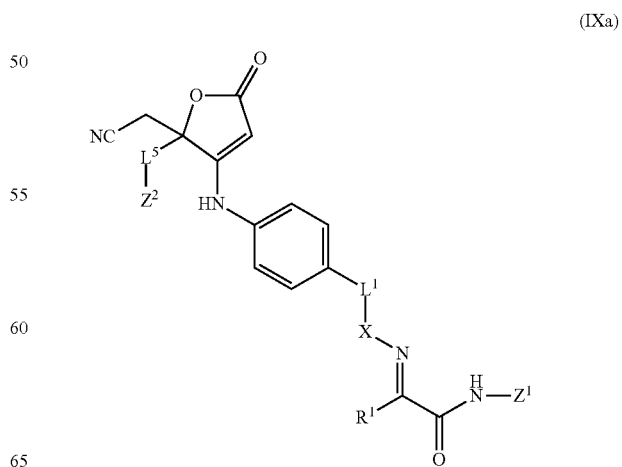

-continued

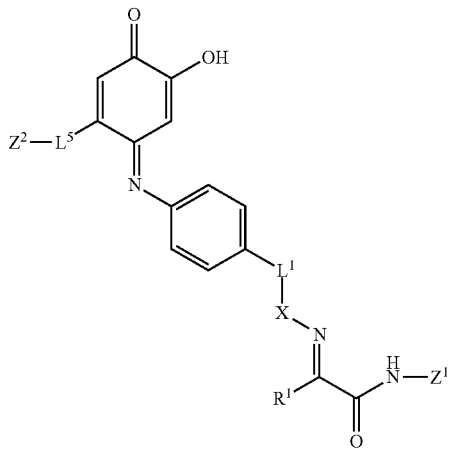

(IXb)

where $L^1$ and $L^5$ are optional linkers, $Z^2$ is a heterologous functional moiety, X is O or NH, $R^1$ is as described above for formula (II), and $Z^1$ is an Fc polypeptide. In certain embodiments, $Z^1$ includes N-terminal lysine-threonine residues, and R' is the amino acid sidechain of alanine.

Methods of Generating Fc Conjugates

The subject Fc conjugates may be prepared by conjugating the subject modified Fc polypeptides with a heterologous functional moiety by using a variety of methods, the chemistry and steps of which are known to one of ordinary skill in the art. Methods and chemistries of interest that may be adapted for use in preparing the subject Fc conjugates include those described in Hermanson, "Bioconjugate Techniques" 2nd Edition, Academic Press, 2008.

In some embodiments, the method includes conjugating a modified Fc polypeptide that includes an aldehyde or a ketone group with a heterologous functional moiety that includes a hydroxylamino group, or a hydrazine or hydrazide group to produce oxime or hydrazone cross-links, respectively. Any convenient methods of conjugating to aldehyde or ketone groups to produce an oxime or hydrazone linkage may be utilized.

In other embodiments, the method includes chemoselectively conjugating a modified Fc polypeptide that includes an aniline group with a heterologous functional moiety that includes an aminophenol group (or alternative convenient oxidative coupling group) to oxidatively couple the aniline and aminophenol groups. Any convenient methods of oxidatively coupling, and coupling reagents or functional groups for achieving the same, may be adapted for use in the subject methods, including but not limited to, those methods and reagents described by Geoghegan et al., *Bioconj. Chem.* 1992, 3, 138-146; and Liu et al., *J. Am. Chem. Soc.* 2006, 128, 15228-15235. In certain embodiments, the conjugation is mediated by sodium periodate or ferricyanide ($K_3Fe(CN)_6$).

Heterologous Functional Moieties

Suitable heterologous functional moieties can be of any of a variety of classes of molecules including, e.g., polypeptides, nucleic acids, DNA aptamers, peptide aptamers, small molecules, nanoparticles, drug delivery vehicles, ligands, polymers, liposomes, and oligosaccharides.

A heterologous functional moiety can provide for a variety of functionalities, including, but not limited to, pro-angiogenic activity; anti-angiogenic activity; cytotoxicity; reduction of IgE production; specific modulation of gene expression; cell binding activity; growth factor activity; and the like.

Polypeptides

In some cases, the heterologous functional moiety is a polypeptide, where suitable polypeptides can have a length of from about 3 amino acids to 1000 amino acids (or longer than 1000 amino acids), e.g., from about 3 amino acids (aa) to about 5 aa, from about 5 aa to about 10 aa, from about 10 aa to about 15 aa, from about 15 aa to about 25 aa, from about 25 aa to about 50 aa, from about 50 aa to about 75 aa, from about 75 aa to about 100 aa, from about 100 aa to about 250 aa, from about 250 aa to about 500 aa, from about 500 aa to about 750 aa, or from about 750 aa to about 1000 aa (or more than 1000 aa).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes polypeptides comprising one or more of a fatty acid moiety, a lipid moiety, a sugar moiety, and a carbohydrate moiety. The term "polypeptides" includes post-translationally modified polypeptides.

Suitable polypeptides include, e.g., an enzyme, a hormone, a cytokine, a binding protein, a toxin, and the like. Exemplary therapeutic peptides include, but are not limited to, hormones, growth factors, cytokines, chemokines, binding peptides, blocking peptides, toxins, angiogenic factors, anti-angiogenic factors, antibiotics, anti-cancer peptides, anti-viral peptides, pharmaceutical peptides, enzymes, agonists, antagonists, hematopoietic agents such as erythropoietin, and the like.

In some cases, the polypeptide heterologous functional moiety comprises one or more naturally occurring non-genetically encoded L-amino acids, synthetic L-amino acids or D-enantiomers of an amino acid. For example, a Peptide can comprise only D-amino acids. For example, a Peptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

In some cases, the heterologous functional moiety is a mimetic. Mimetics are peptide-containing molecules that mimic elements of protein secondary structure. See, for example, Johnson et al., "Peptide Turn Mimetics" in "Biotechnology and Pharmacy", Pezzuto et al., Eds., Chapman and Hall, New York (1993). The rationale behind the use of peptide mimetics is that the peptide backbone of proteins exists chiefly to orient amino acid side chains so as to facilitate molecular interactions, such as those of antibody and antigen. A peptide mimetic is expected to permit molecular interactions similar to the natural molecule. These principles may be used to engineer second generation molecules having many of the natural properties of a naturally-occurring peptide, but with altered or improved characteristics, such as increased absorption across the stomach or intestine and/or improved stability or activity in vivo.

Drugs

Drugs that can be conjugated to a parent Fc to generate a subject drug-Fc conjugate include, but are not limited to, anthracycline, an epipodophyllotoxin, a taxane, an antimetabolite, an alkylating agent, an antibiotic, a COX-2 inhibitor, an antimitotic, an antiangiogenic agent, a proapoptotic agent, doxorubicin, methotrexate, CPT-11, 5-fluorouracil, bleomycin, busulfan, carboplatin, chlorambucil, cisplatin (CDDP), cyclophosphamide, dactinomycin, daunorubicin, an estrogen receptor binding agent, etoposide (VP16), farnesyl-protein transferase inhibitor, gemcitabine, ifosfamide, mechlorethamine, melphalan, mitomycin, navelbine, nitrosourea, plicamycin, procarbazine, raloxifene, tamoxifen, paclitaxel, temazolomide, transplatinum, vinblastine, vincristine, a camptothecan, a nitrogen mustard, an alkyl sulfonate, a triazene, a folic acid analog, a pyrimidine analog, a purine analog, a platinum coordination complex, and a hormone.

Drugs that can be conjugated to a parent Fc to generate a subject drug-Fc conjugate include, but are not limited to, aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin.

Anti-Angiogenic Agents

Exemplary anti-angiogenic agents suitable for conjugation to a parent Fc to generate a subject Fc conjugate include, but are not limited to, angiostatin, baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4, and minocycline.

Nucleic Acids

In some cases, the heterologous functional moiety is a nucleic acid. The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, and the like.

Suitable nucleic acids include a nucleic acid comprising a nucleotide sequence encoding a polypeptide; a nucleic acid comprising a nucleotide sequence encoding an RNA; an antisense RNA; a siRNA; a microRNA; an RNA or a DNA aptamer; a decoy RNA; and the like.

Aptamers

In some cases, the heterologous functional moiety is an aptamer. See, e.g., Keefe et al. (2010) *Nat. Rev. Drug Discov.* 9:537. An aptamer binds to a non-nucleic acid ligand, such as a small organic molecule or protein, e.g., a transcription or translation factor, and subsequently modifies (e.g., inhibits) activity. An aptamer can fold into a specific structure that directs the recognition of the targeted binding site on the non-nucleic acid ligand.

Aptamers may be prepared by any known method, including synthetic, recombinant, and purification methods, and may be used alone or in combination with other ligands specific for the same target. In general, a minimum of approximately 3 nucleotides, e.g., at least 5 nucleotides, are necessary to effect specific binding. Aptamers of sequences shorter than 10 bases may be used; alternatively, aptamers of 10, 20, 30 or 40 nucleotides, or longer than 40 nucleotides may be used. For example, an aptamer can have a length of from about 10 nucleotides (nt) to about 20 nt, from about 20 nt to about 30 nt, from about 30 nt to about 40 nt, to about 50 nt, from about 50 nt to about 60 nt, from about 60 nt to about 70 nt, from about 70 nt to about 80 nt, from about 80 nt to about 90 nt, or from about 90 to about 100 nt.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S, Not all linkages in an oligomer need to be identical.

Methods for preparation and screening of aptamers that bind to particular targets of interest are well known, for example U.S. Pat. No. 5,475,096 and U.S. Pat. No. 5,270,163. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) is retained during separation. Each cycle results in an enrichment of aptamers with high affinity for the target. Repetition for between three to six selection and amplification cycles may be used to generate aptamers that bind with high affinity and specificity to the target.

In some embodiments, the aptamer is an anti-VEGF aptamer. For anti-VEGF aptamers, see, e.g., Ng et al. (2006) *Nature Reviews Drug Discovery* 5:123; and U.S. Pat. Nos. 6,426,335; 6,168,778; 6,147,204; 6,051,698; and 6,011,020. See also, U.S. Patent Publication Nos. 2012/0207671 and 2012/0148584.

Nanoparticles

In some cases, the heterologous functional moiety is a nanoparticle.

Drug Delivery Vehicles

In some cases, the heterologous functional moiety is a drug delivery vehicle, where suitable drug delivery vehicles include, but are not limited to, a viral capsid, a liposome (e.g., a lipid vesicle), a dendrimer, a biodegradable particle, and the like.

Ligands

In some cases, the heterologous functional moiety is a small molecule targeting group, e.g., a ligand for a cell-surface receptor. Suitable ligands include, e.g., neurotransmitters, hormones, ligands that bind cancer biomarkers, kinase inhibitors, integrin-binding ligands, and the like. A ligand can be a naturally-occurring ligand, or a synthetic ligand.

Polymers

In some cases, the heterologous functional moiety is a polymer (e.g., a polymer other than a polypeptide or a nucleic acid). Suitable polymers include natural polymers, semisynthetic polymers, and synthetic polymers. Suitable synthetic polymers include, but are not limited to, polymers or copolymers derived from polydioxane, polyphosphazene, polysulphone resins, poly(acrylic acid), poly(acrylic acid) butyl ester, poly(ethylene glycol), poly(propylene), polyurethane resins, poly(methacrylic acid), poly(methacrylic acid)-methyl ester, poly(methacrylic acid)-n butyl ester, poly (methacrylic acid)-t butyl ester, polytetrafluoroethylene, polyperfluoropropylene, poly N-vinyl carbazole, poly(methyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid) or poly(L-lactide); poly(e-caprolactone); poly(lactide-co-glycolide); poly(hydroxybutyrate); poly(hydroxybutyrate-co-valerate); polydioxanone; polyorthoester; polyanhydride; poly(glycolic acid) (PGA); poly (D,L-lactide) (PDLL); poly(L-Lactide)(PLL); copolymers of PGA, poly(D,L-lactic acid) (PDLA), and/or poly(lactic acid) (PLA); poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g., poly(ethylene oxide) (PEO)/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

Suitable hydrophobic polymers include poly(L-lactide), poly(glycolide), poly(e-caprolactone), copolymers of lactide and/or glycolide or/and poly(e-caprolactone), hydrophobic peptides or a combination of hydrophobic peptides, polyurethanes. Any hydrophobic polymer that can form a micelle in water is suitable for use as a hydrophobic polymer. Suitable hydrophobic polymers include, e.g., poly(glycolide) or poly(glycolic acid); poly(e-caprolactone); poly(D, L-lactide); poly(L-Lactide); copolymers of these and other polyesters; polyamides; polyanhydrides; polyurethanes; poly(ortho esters); poly(iminocarbonates). In some embodiments, the hydrophobic polymer of the nanoparticle (or microparticle) is poly-L-lactide.

Suitable hydrophilic polymers include, but are not limited to, poly(ethylene glycol); poly(vinyl alcohol); polyethers; poly(methacrylic acid); poly(acrylic acid); poly(hydroxyethylmethacrylate) (pHEMA); hyaluronic acid; and hyaluronate.

Compositions

The present disclosure provides compositions, including pharmaceutical compositions, comprising a subject Fc conjugate. Compositions comprising a subject compound can include one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; a membrane penetration facilitator; and the like.

The present disclosure provides pharmaceutical compositions comprising a subject Fc conjugate. A subject compound can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Utility

A modified Fc, or an Fc conjugate, of the present disclosure finds use in a variety of applications. For example, a subject Fc conjugate can be used in various research, diagnostic, and therapeutic applications.

Cytotoxicity

A subject Fc conjugate is in some embodiments useful for mediating cytotoxicity toward a target cell. A subject Fc conjugate binds to an Fc receptor on a cytotoxic immune cell (e.g., a cytotoxic T cell, or an NK cell), thereby mediating killing of a target cell.

Target cells include, but are not limited to, cancer cells. Thus, the present disclosure provides methods of killing, or inhibiting the growth of, a target cancer cell, the method involving contacting a cytotoxic immune effector cell (e.g., a cytotoxic T cell, or an NK cell) with a subject Fc conjugate, such that the Fc conjugate binds to the cytotoxic immune effector cell and, in the presence of a target cancer cell, the cytotoxic immune effector cell mediates killing of the target cell. The heterologous functional moiety on the Fc conjugate can provide additional specificity for a particular target cell and/or can provide for an additional cytotoxic effect.

The present disclosure provides a method of treating cancer in an individual having a cancer, the method involving administering to the individual an effective amount of a subject Fc conjugate. The Fc conjugate can be provided in a pharmaceutical composition, together with one or more pharmaceutically acceptable excipients. The Fc conjugate (or pharmaceutical composition comprising the Fc conjugate) can be administered systemically (e.g., intravenously, etc.) or locally (e.g., at or near the site of a cancer cell or tumor).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithielieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1: Preparation and Characterization of Fc Conjugates

Fc molecules with added functionality were created by installing synthetic molecules at the N-termini of crystallizable fragment domains (Fc's) via a chemical modification approach. First, a pyridoxal 5'-phosphate (PLP) mediated N-terminal transamination reaction provided a compatible method for site-selectively installing ketones as reactive handles on Fc domains. High levels of conversion were achieved. For elaboration of the newly installed chemical handles, two different approaches for the ligation of heterologous groups to the Fc domain were used. In the first approach, alpha-effect amines were used to create oxime or hydrazone linkages. In the second approach, the ketone was used as a site to introduce a second reaction handle: an aniline group that can participate in a recently reported oxidative coupling reaction. The oxidative coupling provides a highly efficient ligation strategy requiring very short reaction times (two min or less) at room temperature.

Fc domains were functionalized with DNA aptamers. The specificity of the aptamers for binding their cellular targets was demonstrated, as was their ability of the modified Fc domains to bind to complement proteins.

Materials and Methods

General Experimental Procedures and Materials

Unless otherwise noted, all chemicals and solvents were of analytical grade and used as received from commercial sources. Water (dd-$H_2O$) used in biological procedures or as the reaction solvent was deionized using a NANOpure purification system (Barnstead, USA). All oligonucleotides were obtained from Integrated DNA Technologies (Coralville, Iowa). All cell culture reagents were obtained from Gibco/Invitrogen Corp. (Carlsbad, Calif.) unless otherwise noted. Cell culture was conducted using standard techniques. Jurkat and Ramos cells were grown in T-25 culture flasks (Corning) in RPMI Medium 1640 supplemented with 10% (v/v) fetal bovine serum (FBS, Omega Scientific) and 1% penicillin/streptomycin (P/S, Sigma). U266 cells were grown in T-25 culture flasks (Corning) in RPMI Medium 1640 supplemented with 15% (v/v) fetal bovine serum (FBS, Omega Scientific) and 1% penicillin/streptomycin (P/S, Sigma).

Instrumentation and Sample Analysis

Liquid Chromatography-Mass Spectrometry (LC-MS).

Fc protein bioconjugates were analyzed using an Agilent 1200 liquid chromatograph (LC; Santa Clara, Calif.) that was connected in-line with an LTQ Orbitrap XL hybrid mass spectrometer equipped with an electrospray ionization source (ESI; Thermo Fisher Scientific, Waltham, Mass.), located in the QB3/Chemistry Mass Spectrometry Facility at UC Berkeley. The LC was equipped with a reversed-phase $C_8$ column (100 mm×1.0 mm, 5 μm particles, Restek, Bellefonte, Pa.). Solvent A was 0.1% formic acid/99.9% water and solvent B was 0.1% formic acid/99.9% acetonitrile (v/v). For each sample, approximately 200 picomoles of protein analyte was injected onto the column. Following sample injection, analyte trapping was performed for 5 min with 99.5% A. The elution program consisted of a linear gradient from 30% to 95% B over 19.5 min, isocratic conditions at 95% B for 5 min, a linear gradient to 0.5% B over 0.5 min, and then isocratic conditions at 0.5% B for 9.5 min. Solvent (Milli-Q water) blanks were run between samples, and the autosampler injection needle was rinsed with Milli-Q water after each sample injection, to avoid cross-contamination between samples. Mass spectra were recorded in the positive ion mode over the range m/z=450-2000. Raw mass spectra were processed using Xcalibur software (version 2.0.7 SP1, Thermo) and protein charge state distributions were deconvoluted using ProMass software (version 2.5 SR-1, Novatia, Monmouth Junction, N.J.).

High Performance Liquid Chromatography (HPLC).

HPLC was performed on an Agilent 1100 Series HPLC System (Agilent Technologies, USA). Sample analysis for all HPLC experiments was achieved with an inline diode array detector (DAD). Anion exchange HPLC of Fc-DNA conjugates was accomplished using Biosep-DEAE-PEI column (Phenomenex).

Gel Analyses.

For protein analysis, sodium dodecyl sulfate-polyacrylamide gel electrophoresis (SDS-PAGE) was carried out on a Mini-Protean apparatus from Bio-Rad (Hercules, Calif.), following the protocol of Laemmli.[1] The reducing protein electrophoresis samples were heated for 10 minutes at 95° C. in the presence of β-mercaptoethanol to ensure reduction of any disulfide bonds. Gels were run for 40 minutes at 200 V to allow good separation of bands. Commercially available markers (Fisher) were applied to at least one lane of each gel for assignment of apparent molecular masses. Visualization of protein bands was accomplished by staining with Coomassie Brilliant Blue R-250 (Bio-Rad). For fluorescent protein conjugates, visualization was accomplished on a Typhoon 9410 (Amersham Biosciences).

Construction of the Plasmids for the Expression of Fc Domains

To express the Fc substrates, the pInFuse-hIgG1-Fc2 (InvivoGen, San Diego, Calif.) plasmid, which contained the human IgG1-Fc gene with its introns and an IL2 signal sequence, was used. A short intron was present between each region: one intron was located between the hinge and the CH2 domain and one intron was located between CH2 and CH3 (FIG. 1B). The Fc protein expressed from this plasmid was comprised of the CH2 and CH3 domains of the IgG1 heavy chain. Intracellular cleavage of this sequence occurs after Ser20 and leads to the secretion of the protein to extracellular medium (FIG. 1B). As in the sequence shown in FIG. 1C, Ile-Ser-Ala remains at the N-terminus of the secreted Fc protein after the IL2 signal sequence is cleaved. The DNA sequence ATATCGGCC encoding Ile-Ser-Ala at the N-terminus was replaced with GCAAAGACC, encoding Ala-Lys-Thr (the optimized sequence for PLP-mediated transamination) using Quikchange site-directed mutagenesis kit (Stratagene, La Jolla, Calif.). Moreover, the ATG following these 9 bases was also changed to ACG to eliminate the potential of having another translation initiation site. This was accomplished via two rounds of Quikchange site-directed mutagenesis: the first round mutated ISA to AKT and the second mutated M to T.

Figure 1B:
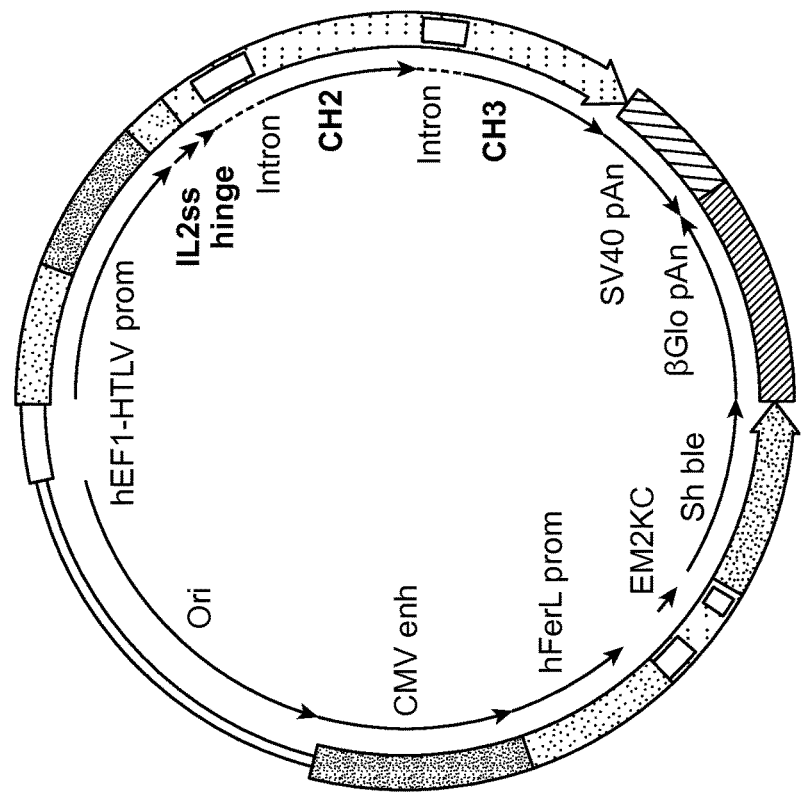

FIGS. 1A-C. Structure and expression vector for Fc of human IgG1. (a) Structure of Fc region of human immunoglobulin G1 (IgG1) is comprised of two monomers, each containing two domains (CH2 and CH3), with glycosylation at Asn297. The hinge region, which contains two disulfide bonds, serves as a flexible spacer between Fc and Fab. (b) A plasmid expressing human IgG1 Fc protein with introns and IL2 signal sequence (IL2ss) was constructed and used for these experiments. The introns helped to increase the expression level of the IgG1 Fc, and IL2ss signaled the secretion of the Fc protein to the extracellular medium. (c) The sequence of the IL2ss (grey) and human IgG1 Fc (upper case letters) is shown with introns (lower case letters) inserted between hinge and CH2 and between CH2 and CH3 (red). The mutated region is in bold.

The sequences of mutagenic and sequencing primers used in this study are listed in Table 1.

TABLE 1

Primer sequences used for construction of plasmid expressing AKT-Fc and sequencing primers.

| Purpose | Primers* |
|---|---|
| Mutating ISA to AKT | 5'-GCACTAAGTCTTGCACTTGTCACGAATTCGGCAAAGACCATGGTTAGATCTGACAAAACT-3' (SEQ ID NO: 21)<br>5'-ATGTGTGAGTTTTGTCAGATCTAACCATGGTCTTTGCCGAATTCGTGACAAGTGCAAGAC-3' (SEQ ID NO: 22) |
| Mutating M to T | 5'-TGTCACGAATTCGGCAAAGACCACGGTTAGATCTGA-3' (SEQ ID NO: 23)<br>5'-AGTTTTGTCAGATCTAACCGTGGTCTTTGCCGAATTC-3' (SEQ ID NO: 24) |
| Sequencing | 5'-TGCTTGCTCAACTCTACGTC-3' (SEQ ID NO: 25)<br>5'-TTGCAGCTTATAATGGTTACAAA-3' (SEQ ID NO: 26) |

*The mutated sites are in bold.

The polymerase chain reaction (PCR) mixture was composed of 1 μL of 50 ng/μL plasmid template, 5 μL of each primer (25 ng/μL), 1 μL of dNTP mixture, 5 μL of 10× buffer, 1 μL of PfuTurbo DNA polymerase (2.5 units/μL) and 33 of μL of dH$_2$O. The reaction was started with 2 min at 95° C. to predenature the template, followed by 18 cycles of 30 sec at 95° C., 1 min at 55° C. and 6 min at 70° C. The PCR ended with final polymerization at 70° C. for 10 min and the reaction mixture was left at 10° C. until the next step. After the PCR reaction, 1 μL of DpnI (10 units/μL) was added and the mixture was incubated at 37° C. for 2 h to degrade the original unmodified plasmid templates. After DpnI digestion, 2 μL of the mixture was used to transform E. coli XL1-Blue competent cells by heat-shock following the manufacturer's protocol. The transformed E. coli XL1-Blue was spread on Luria Broth (LB) plates containing Zeocin (Fast-Media Zeo Agar, InvivoGen) and incubated at 37° C. overnight (~16 h). Colonies were selected and grown in 5 mL terrific broth (TB) media containing Zeocin (Fast-Media Zeo TB, InvivoGen) at 37° C. overnight (12-16 h). Plasmid DNA was isolated using a QIAprep Spin Miniprep Kit (Qiagen). The DNA sequences were confirmed by gene sequencing. The sequences of the primers used for sequencing are listed in Table 1.

TABLE 2

Sequence of DNA oligonucleotides used in the protein modification.

| DNA oligo-nucleotides | Sequence |
| --- | --- |
| Sgc8c (41-mer) | 5'-ATCTAACTGCTGCGCCGCCGGGAAAATACTGTACG GTTAGA-3' (SEQ ID NO: 27) |
| TD05.1 (37-mer) | 5'-AGGAGGATAGTTCGGTGGCTGTTCAGGGTCTCCTC CT-3' (SEQ ID NO: 28) |
| M2M2 (41-mer) | 5'-CCCTAGAGTGAGTCGTATGACCCTAGAGTGAGTCG TATGAA-3' (SEQ ID NO: 29) |

General Procedure for Expression of AKT-Fc

The plasmids expressing AKT-Fc constructed above were transiently transfected into human embryonic kidney (HEK) 293T cells using Lipofectamine 2000 (Invitrogen) in Opti-MEM medium following the protocol from Invitrogen. The cells were incubated at 37° C. in 5% $CO_2$. After 2 days, media were collected and secreted antibodies were purified using protein G affinity chromatography, according to the procedure from the manufacturer (Pierce). Fresh media were added and cultures were grown for additional 3 days, after which additional antibodies were harvested and purified as above. Purified protein was buffer exchanged into phosphate buffered saline (PBS) using Amicon Ultra 4 mL 10,000 MWCO (Millipore) centrifugal ultrafiltration membranes. Purity was evaluated by SDS-PAGE with Coomassie staining.

General Procedure for PLP Transamination

The 2× protein stock solutions were prepared at 10-40 μM using 25 mM phosphate buffer at pH 6.5. The 2× (200 mM) PLP stock solutions were prepared in 25 mM phosphate buffer and the pH of the solution was adjusted to 6.5 using NaOH solution. Protein and PLP stock solutions were mixed in equal volumes. The reaction mixture was briefly agitated to ensure mixing and then incubated without further agitation at 37° C. for 1 h. After incubation, the PLP was removed using NAP Sephadex size exclusion columns (GE Healthcare). The resulting keto-Fc solution was then concentrated and the buffer was exchanged with 25 mM phosphate buffer (pH 6.5), using Millipore 0.5 or 4 mL spin concentrators (MWCO 10 kDa), following the protocol from the manufacturer.

General Procedure for Hydrazone and Oxime Formation

The reaction was performed with 10-40 μM keto-Fc and $RONH_2$ or $R(CO)NHNH_2$ at varied concentrations. For the analysis of PLP transamination efficiency, $BnONH_2$ and Alexfluor 488-$ONH_2$ were added to keto-Fc to a final concentration of 100 mM and 80 μM, respectively. For the attachment of an oxidative coupling partner, aniline-$ONH_2$ was added to a final concentration of 25 mM. To make Fc-aptamer constructs, keto-Fc was mixed with the hydrazide-aptamer at a final concentration of 100 μM in the presence of 100 mM aniline, which is known to enhance the rate of hydrazone formation. Dirksen, A.; Hackeng, T. M.; Dawson, P. E. Angew. Chem. Int. Ed. 2006, 45, 7581-7584. The reaction mixture was incubated at RT for 18-50 h. All the reactions were carried out in 25 mM phosphate buffer (pH 6.5), except for oxime formation with aniline-$ONH_2$, which was done in 25 mM phosphate buffer (pH 5). Following the reaction, the small molecules were removed using NAP Sephadex size exclusion columns (GE Healthcare) and the resulting product mixtures were concentrated using Millipore 0.5 or 4 mL spin concentrators (Molecular weight cutoff (MWCO)=10 kDa), following the protocol from the manufacturer. The percent reaction conversion for the Fc samples with small molecules was analyzed using liquid chromatography-mass spectroscopy (LCMS) and the modification with large molecules was analyzed using sodium dodecyl sulfate-polyacrylamide gel electrophoresis (SDS-PAGE) with Coomassie staining.

The General Procedure for Oxidative Coupling

To a solution of 10-40 μM Fc-aniline (9) in 25 mM phosphate buffer (pH 6.5) was added a solution of aminophenol-aptamer (10b) or aminophenol-2k PEG (10a) to a final concentration of 100 μM. Sodium periodate (Sigma-Aldrich) was dissolved to a concentration of 10 mM in 25 mM phosphate buffer (pH 6.5). The sodium periodate was then added to the reaction mixture to reach a final concentration of 1 mM, and the reaction was allowed to proceed for 2 min at RT. In some cases, a solution of mannose was also added to a final concentration of 10 mM or 100 mM before addition of the periodate solution. The resulting protein samples were purified on NAP Sephadex size exclusion columns (GE Healthcare) and concentrated using Millipore 0.5 or 4 mL spin concentrators (MWCO 10 kDa), following the protocol from the manufacturer.

Purification of Fc-Aptamer Constructs

The resulting Fc-DNA conjugates from both hydrazone formation and oxidative coupling were purified from unreacted Fc and DNA using anion exchange high performance liquid chromatography (HPLC) with a 20-min gradient of 100% buffer A to 5% buffer A 95% buffer B, where buffer A is 25 mM sodium phosphate buffer pH 6.5 and buffer B is 25 mM sodium phosphate buffer pH 6.5 with 1 M NaCl. The fractions collected were analyzed using SDS-PAGE and those containing Fc-DNA constructs were combined and concentrated using Millipore 0.5 mL spin concentrators (MWCO 10 kDa).

Flow Cytometry Experiments

Flow cytometry was used to determine binding ability of all the Fc-aptamer constructs. All experiments were carried out in triplicate. For all samples, 100 μL of $3 \times 10^6$ cells/mL of Jurkat, Ramos, and U266 was used, suspended in binding buffer (4.5 g/L glucose, 5 mM $MgCl_2$, 0.1 mg/mL yeast tRNA (Sigma) and 1 mg/mL bovine serum albumin (BSA) (Fisher) in Dulbecco's PBS with calcium chloride and magnesium chloride (Invitrogen)). To these cells were added 10 μL of a series of 400 nM Fc-aptamer construct solutions. The samples were then incubated on ice for 1 h. The resulting cells were washed with 500 μL of binding buffer and resuspended in an additional 100 μL of binding buffer. Anti-human IgG1 antibody (specific for the Fc domain) with fluorescein isothiocyanate (FITC)-conjugated (Sigma) was then added to a final concentration of ~0.30 µM. Cells were incubated for 1 h on ice in the dark, then washed with 500 µL of binding buffer, and resuspended in 200 µL binding buffer. The cells were analyzed by flow cytometry to determine the amount of FITC fluorescence. For each sample, 10,000 cells were counted.

ELISA for C1q Binding

The binding of human C1q to AKT-Fc, chemically-modified Fc, and Fc-DNA conjugates were assessed by an enzyme-linked immunosorbent assay (ELISA) binding assay, adjusted from a published procedure (Idusogie, E. E.; Presta, L. G.; Totpal, K.; Wong, P. Y.; Meng, Y. G.; Mulkerrin, M. G.; Alerts, E. *J. Immunol* 2000, 164, 4178-4184). High binding Costar 96-well plates (Corning, N.Y.) were coated with varying concentrations of Fc samples in coating buffer (0.05 M sodium carbonate buffer, pH 9) overnight at 4° C. All samples were run in duplicate. The plates were washed three times after each incubation step with 300 µL of PBS+0.05% Tween 20, pH 7.4. After coating, the plates were blocked with 200 µL of ELISA diluent (0.1 M $NaPO_4$/0.1 M NaCl/0.1% gelatin/0.05% Tween 20/0.05% ProClin300) for 1 h at RT, followed by incubation with 100 µL of 2 µg/mL human C1q (Quidel, San Diego, Calif.) in ELISA diluent for 2 h. Then, 100 µL of a 1:400 dilution of sheep anti-human C1q peroxidase-conjugated antibody (Abcam) in ELISA diluent was added and incubated at RT for 1 h. The plates were developed with 100 µL of 3,3',5,5'-tetramethylbenzidine (TMB) substrate buffer (Sigma) at RT for 15 min. The reaction was stopped upon the addition of 100 µL of stop reagent for TMB substrate (Sigma), and the OD was measured at 450 nm using a Spectramax M3 microplate reader (Molecular Devices, Sunnyvale, Calif.). The obtained Hill plots displayed different amplitudes for the binding curves, which were taken to arise from different amounts of Fc samples binding to the wells. The plots were therefore normalized based on their maximum overall absorbance.

Synthesis of Hydrazide-DNA (6)

The 5' thiol DNA oligonucleotide supplied by IDT was reduced in 40 mM TCEP in PBS, pH 7.4 for 2 h at RT. The TCEP was removed using NAP Sephadex size exclusion columns (GE Healthcare). Ten equivalents of 3,3'-N-[ε-maleimidocaproic acid]hydrazide, trifluoroacetic acid salt (EMCH, Pierce), were added to a sample of reduced 5' thiol oligonucleotide in PBS, pH 7.4. The reaction mixture was incubated for 2.5 h at RT. The resulting hydrazide-DNA (6) was purified using NAP Sephadex size exclusion columns (GE Healthcare), followed by spin concentration with Millipore 0.5 mL spin concentrators (MWCO 10 kDa).

Figure 8:
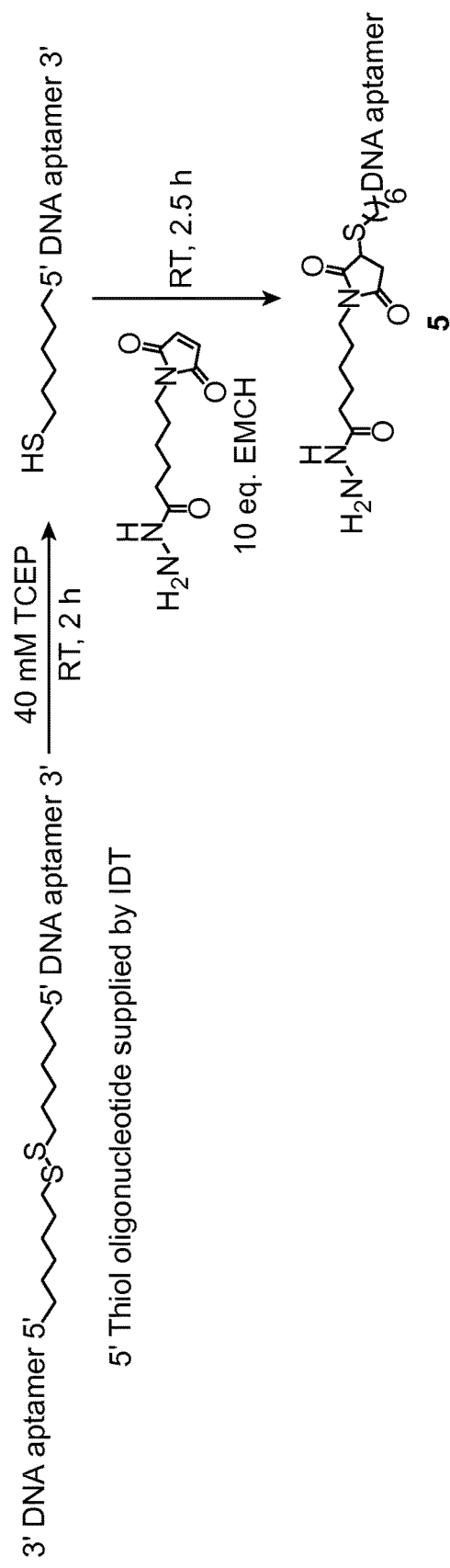
FIG. 8 provides a scheme for the synthesis of hydrazide-DNA oligonucleotide 5.

The scheme for the synthesis of hydrazide-DNA oligonucleotide 5 is depicted in FIG. 8.

Synthesis of Aminophenol-DNA (11b)

The 5' thiol DNA oligonucleotide supplied by IDT was reduced in 40 mM TCEP in PBS, pH 7.4 for 2 h at RT. The TCEP was removed using NAP Sephadex size exclusion columns (GE Healthcare). The resulting product was buffered exchanged into 25 mM phosphate buffer at pH 8 by spin concentration with Millipore 0.5 mL spin concentrators (MWCO 10 kDa). Approximately one equivalent of a nitrophenol-maleimide linker was added to the reduced 5' thiol DNA oligonucleotide and the reaction was carried out in 25 mM phosphate buffer pH 8 at room temperature (RT) for 1 h. The resulting nitrophenol-DNA was then purified using NAP Sephadex size exclusion columns (GE Healthcare), followed by spin concentration with Millipore 0.5 mL spin concentrators (molecular weight cut-off (MWCO) 10 kDa) into PBS. The nitro group was reduced to amine in the presence of 10 mM sodium dithionite at RT for 10 min. The final product aminophenol-DNA was purified using NAP Sephadex size exclusion columns (GE Healthcare), followed by spin concentration with Millipore 0.5 mL spin concentrators (MWCO 10 kDa) into 25 mM phosphate buffer pH 6.5 for subsequent conjugation with Fc proteins.

Figure 9:
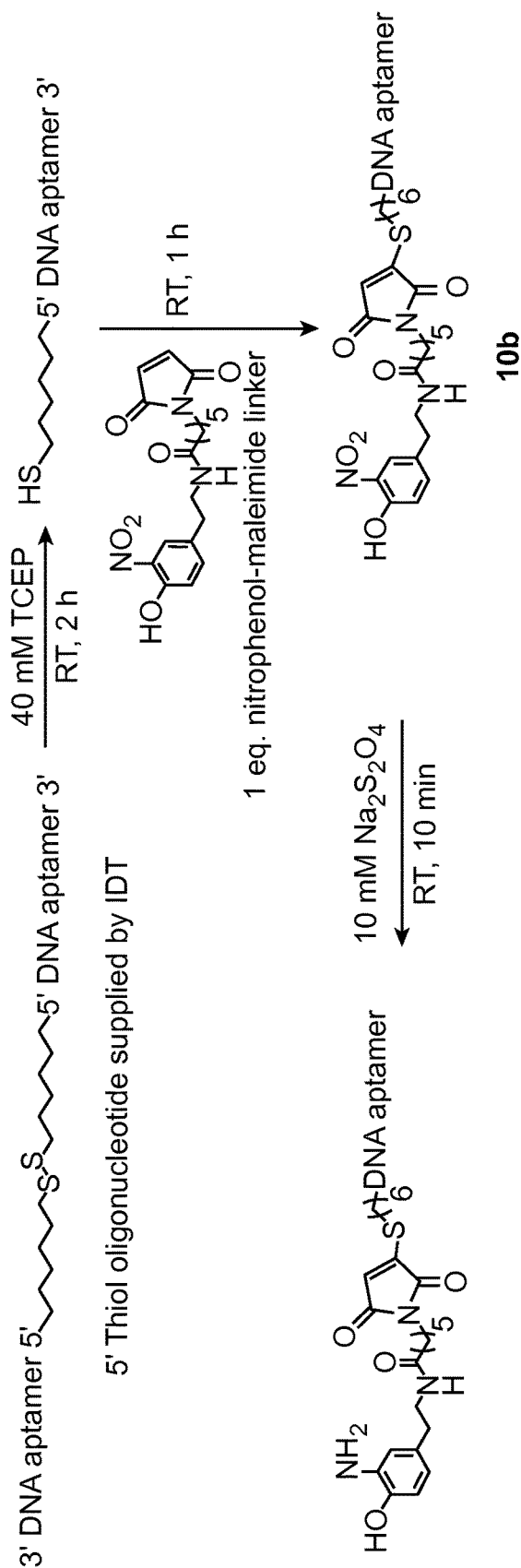
FIG. 9 provides a scheme for synthesis of aminophenol-DNA oligonucleotide 10b.

The scheme for synthesis of aminophenol-DNA oligonucleotide 10b is depicted in FIG. 9.

Synthesis of Aniline-$ONH_2$ (8)

To (boc-aminooxy)acetic acid (280 mg, 1.5 mmol) dissolved in methylene chloride was added dicyclohexylcarbodiimide (362 mg, 1.7 mmol) and N-hydroxysuccinimide (168 mg, 1.5 mmol). After 15 min with stirring, the precipitate was filtered through Celite, followed by a 0.22 µm PVDF syringe filter. To the remaining solution was added 2-(4-aminophenyl)ethylamine (200 mg, 1.5 mmol) and triethylamine (400 mg, 4 mmol). After 1 h of stirring the solution was concentrated under reduced pressure and applied to a silica gel column. Purification using ethyl acetate as the mobile phase afforded approximately 200 mg of the product (45% yield). $^1$H NMR (400 MHz, $CDCl_3$) δ 1.4 (s, 9H), 2.7 (t, 2H), 3.4 (q, 2H), 3.5 (br s, 2H), 4.2 (s, 2H), 6.6 (d, 2H), 7.0 (d, 2H), 8.1 (br s, 1H), 8.5 (s, 1H). The Boc group was removed via exposure to 1:1 trifluoroacetic acid:methylene chloride for 10 min, after which the solvent was removed under a stream of nitrogen. The resulting oil was placed under vacuum overnight. It was then dissolved to 100 mM in water and stored frozen until used. To avoid precipitation, it was necessary to neutralize the residual trifluoroacetic acid by adding phosphate buffer before addition to protein-containing solutions.

Synthesis of 2k PEG-Aminophenol (10a)

2k poly(ethylene glycol) (PEG)-aminophenol (10a) was synthesized according to published protocol (Behrens, C. R.; Hooker, J. M.; Obermeyer, A. C.; Romanini, D. W.; Katz, E. M.; Francis, M. B. *J. Am. Chem. Soc.* 2011, 133, 16398-16401).

Synthesis of Nitrophenol-Maleimide Linker

To tyramine was added dropwise one equivalent of fuming nitric acid at 4° C. using trifluoroacetic acid as the solvent and this resulted in quantitative conversion to o-nitrotyramine. O-nitrotyramine (50 mg, 0.27 mmol) was dissolved in 10 mL DMF and treated with one equivalent of succinimidyl-6-N-maleimidohexanoate (as described in Nielsen, O.; Buchardt, O. *Synthesis* 1991, 10, 819-821) along with sufficient triethylamine to reach pH 8. Multiple equivalents of triethylamine were required due to residual trifluoroacetic acid from the nitration step. After 45 min, 20 mL of 0.1 M $NaHSO_4$ was added to the reaction. The product was extracted with methylene chloride, dried over $Na_2SO_4$, and purified on a silica column using ethyl acetate as the mobile phase. Isolated yield was 33%. $^1$H NMR (300 MHz, $CDCl_3$) δ 1.2 (m, 2H), 1.6 (m, 4H), 2.1 (t, 2H), 2.8 (t, 2H), 3.5 (t, 4H), 5.6 (br s, 1H), 6.6 (s, 2H), 7.0 (d, 1H), 7.5 (d, 1H), 8.0 (s, 1H), 10.5 (br s, 1H).

Results

Recently, the potential of using pyridoxal 5'-phosphate (PLP)-mediated transamination has been demonstrated as a convenient way to install one new functional group in a single location without modifying native free cysteine or lysine residues.[15] Taking advantage of this selectivity, the synthesis of Fc-synthetic molecule hybrids was designed around using PLP-mediated N-terminal transamination to provide a unique ketone group at the N-terminus of the Fc-domain for further functionalization (FIG. 2). The synthetic moiety can then be conjugated to the N-terminus using traditional oxime or hydrazone formation.[16] The use of an oxidative coupling reaction was explored as a new approach to ligate synthetic groups to the protein with significantly enhanced efficiency[17]—a useful feature for the installation of high-value cargo, such as complex drug molecules or the nucleic acid aptamers described herein.

FIG. 2. Modification scheme for Fc proteins. First, ketone functional groups are installed at the N-termini through PLP-mediated transamination. These groups can then be functionalized using two different approaches. The first involves the direct attachment of molecules of interest via oxime formation (with 4) or hydrazone formation (with 5). The second strategy uses a highly efficient oxidative coupling reaction. This approach involves the chemoselective coupling of aniline groups on the Fc proteins (9) with aminophenol-containing reagents (10).

Since the efficiency of PLP-mediated transamination depends on the sequence of the N-terminus,[15c] the Fc protein was first mutated to contain a highly reactive alanine-lysine-threonine (AKT) sequence[15d] immediately following the IL2 signaling peptide (see sequence in FIG. 1C). This leader peptide was cleaved during the secretion of the AKT-Fc proteins from the host cells. The protein was expressed in glycosylated form in transfected HEK 293T cells (see mass spectrometry characterization in FIG. 3A-C) and purified using a protein G column.

Figure 3A:
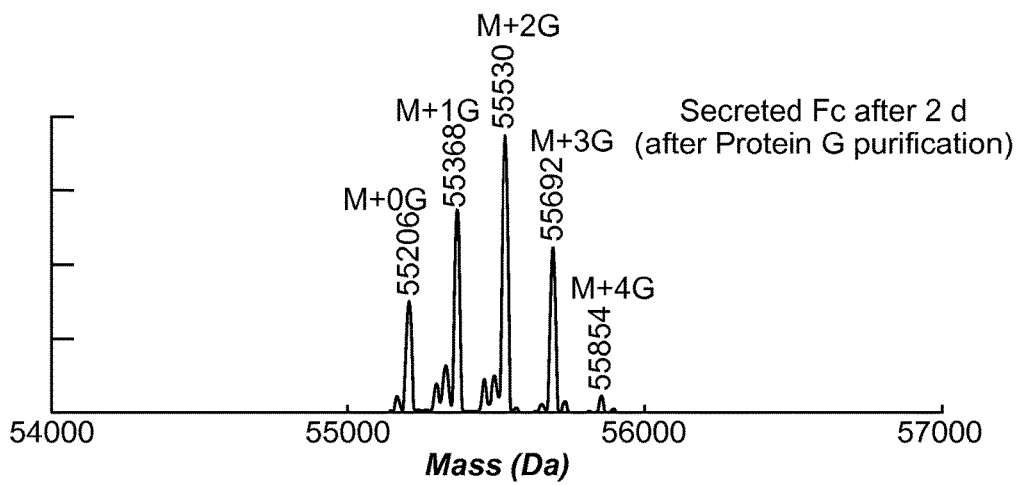
FIGS. 3A-C depict LCMS analysis of (a) the Fc protein collected 2 days after transfection; (b) the Fc protein collected 5 d after transfection (fresh Opti-MEM media was replaced after 2 d); and (c) the Fc protein after treatment with PNGase F.
Figure 3B:
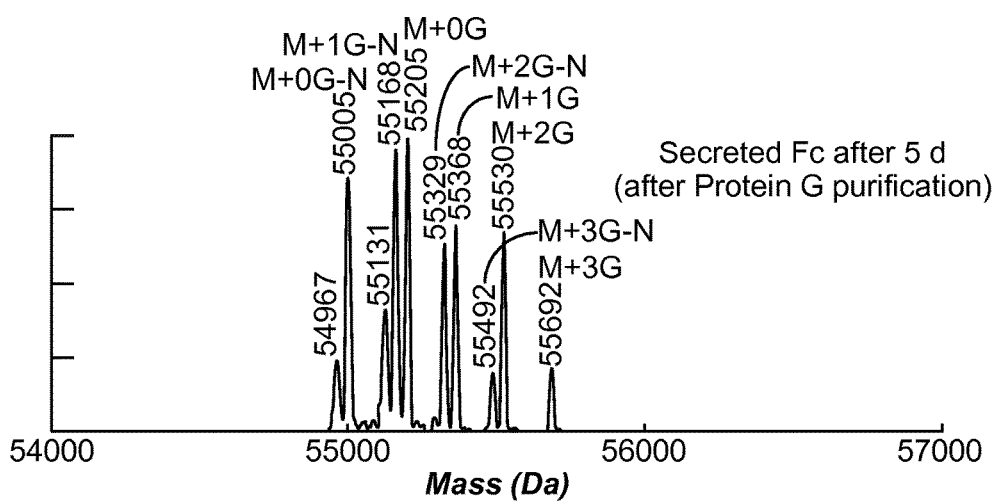
Figure 3C:
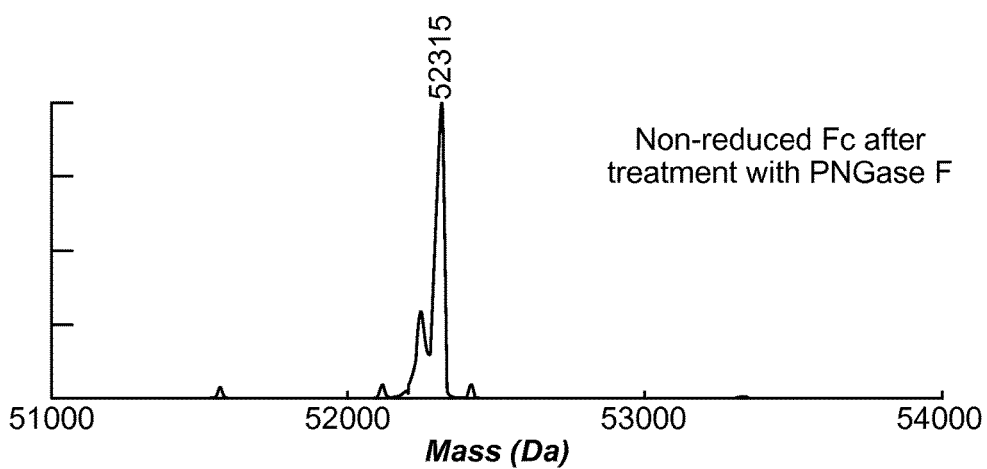

FIGS. 3A-C. LCMS analysis of (a) the Fc protein collected 2 d after transfection; (b) the Fc protein collected 5 d after transfection (fresh Opti-MEM media was replaced after 2 d); and (c) the Fc protein after treatment with PNGase F (both 2 d and 5 d samples were identical). The heterogeneity was a result of differences in the number of galactose (G, 162 Da) and N-acetylglucosamine (N, 203 Da) residues that were incorporated. Because each monomer of the Fc protein could contain up to two galactose residues, there are five possibilities of glycosylation patterns for the Fc dimer, corresponding to a normal distribution of M+0G (55206 Da), M+1G (55368 Da), M+2G (55530 Da), M+3G (55692 Da), and M+4G (55854 Da). Additionally, peaks at 55005, 55166, 55329, and 55492 Da appear to match M+0G-N, M+1G-N, M+2G-N, and M+3G-N, and M+3G-N, respectively.

The AKT-Fc proteins were then exposed to a freshly prepared 100 mM solution of PLP in pH 6.5 phosphate buffer at 37° C. for 1 h. Due to the small mass difference (1 Da) corresponding to the transamination of each terminus, the resulting protein was exposed to benzyl hydroxylamine (BnONH$_2$, 4a) for 2 d at RT before characterization using mass spectrometry. To simplify the analysis, the carbohydrate domain was removed from the samples using PNGase F. As shown for the non-reduced Fc products in FIGS. 4A and 4B, very high conversion was observed. Two major products were obtained (6a and 6a+PLP), both resulting from the desired oxime formation reaction at the two Fc termini. The higher mass product resulted from an aldol reaction between the aldehyde of PLP and the transaminated terminus during the first reaction step (shown as 3+PLP in FIG. 2). The only other product that was evident was a small amount of Fc with a single oxime modification (species 12). In samples lacking PLP treatment, exposure to BnONH$_2$ led to no observable modification. Oxime formation using AlexaFluor 488 alkoxyamine was also used to detect reaction progress via SDS-PAGE (FIG. 4C). Fluorescence was detected in the +PLP lanes using both reducing and non-reducing gel loading buffers, suggesting that AKT-Fc underwent transamination by PLP and that the Fc remained in dimeric state under the reaction conditions. In addition to the expected products, a small amount of residual Fc dimer (~4-7% by densitometry) was observed in the reduced lane. It was presumed that this resulted from an aldol reaction between the two terminal ketones, which are directly adjacent to one another in the dimeric Fc structure. Such a species would still possess a single remaining ketone group, thus allowing its labeling with the dye molecule. The presence of this minor species could also explain species 12 in FIG. 4B, but the identities of these two byproducts have not been confirmed further due to their very low abundance.

Figure 4A:
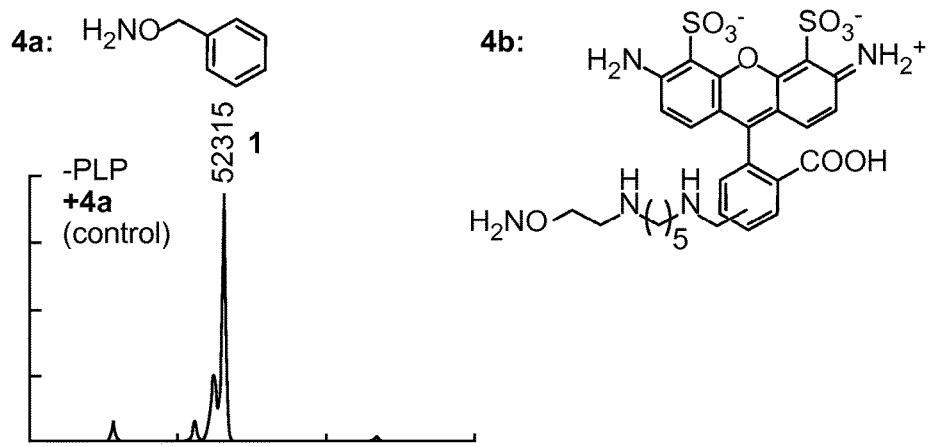
FIGS. 4A-C depict analysis of transamination efficiency for AKT-Fc domains.
Figure 4B:
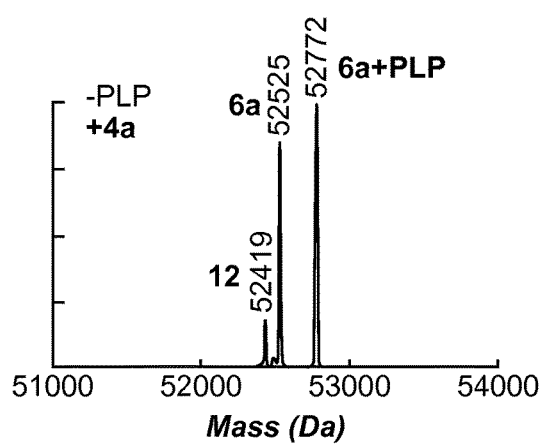
Figure 4C:
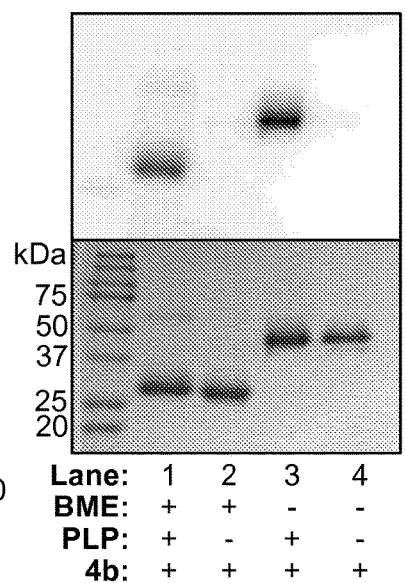

FIGS. 4A-C. Analysis of transamination efficiency for AKT-Fc domains. AKT-Fc (1) was exposed to 50 mM 4a for 40 h at pH6.5, followed by treatment with PNGaseF (a) without prior transamination with PLP (as a negative control), or (b) following transamination with 100 mM PLP at 37° C. for 1 h. The peak at 52315 Da corresponded to unmodified AKT-Fc (expected: 52315 Da). The double-oxime product (6a) appeared at 52525 Da (expected: 52523 Da), and the peak at 52772 Da corresponded to product 6a plus a single PLP addition (expected: 52770 Da). The peak at 52419 Da corresponded to the addition of one molecule of 4a to the AKT-Fc fragment (12, expected: 52419 Da). (c) Samples of AKT-Fc with and without transamination using PLP (100 mM PLP at 37° C. for 1 h) were exposed to 80 μM Alexa-Fluor 488 alkoxyamine (4b) for 43 h in the presence of 100 m Maniline as a catalyst. They were then analyzed by SDS-PAGE under reducing (Lanes 1 and 2) or nonreducing (Lanes 3 and 4) conditions. The fluorescent images of the Fc-AlexaFluor488 oxime products (top) were taken using a Typhoon imaging system. The bottom gel was stained using Coomassie blue.

Figures 5A, 5B:
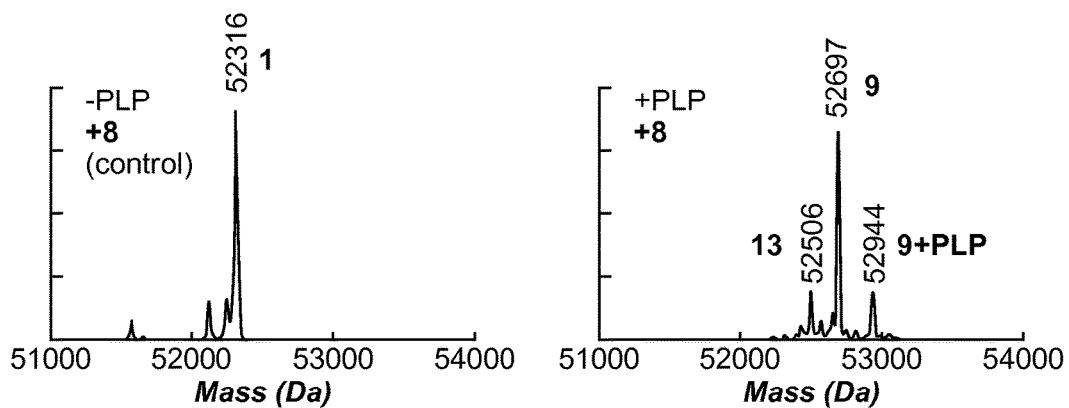
FIGS. 5A-D depict modification of Fc domains via oxidative coupling.

Due to slow kinetics of oxime and hydrazone formation, long reaction times and large excesses of reagent are typically used to reach full conversion. While this is fine for inexpensive small molecules, it poses a problem when the group to be attached is a large or expensive reagent (such as a drug). With these cases in mind, oxime formation was used to attach an aniline-containing small molecule to allow further ligation using oxidative coupling reactions. As reported recently, the periodate-mediated oxidative coupling[18] between anilines and aminophenols can achieve chemoselective protein modification with very high levels of product conversion in less than 2 min. Using the transamination/oxime formation procedure described above with compound 8 produced Fc proteins bearing an aniline group at each of the two termini (species 9 and 9+PLP in FIG. 5B).

Figure 5C:
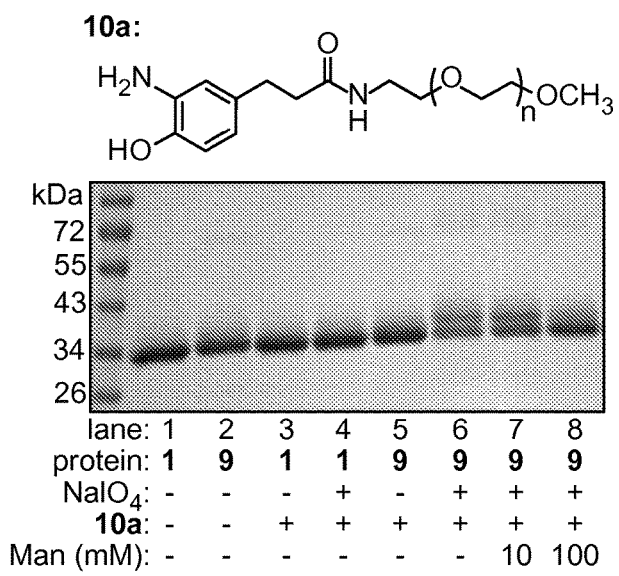

Following successful installation of aniline groups on the Fc proteins, the oxidative coupling reaction was then investigated using aminophenol containing polyethyleneglycol 10a (MW ~2000 Da).[12a] Aniline Fc 9 (10-40 μM) was combined with 100 μM 10a in pH 6.5 phosphate buffer. A stock solution of sodium periodate was added to a final concentration of 1 mM, and the reaction was incubated for 2 min. The resulting solution was then passed through a NAPS gel filtration column to quench and remove the periodate. SDS-PAGE analysis under reducing conditions (and without the use of PNGase F) indicated that 50% of the individual Fc chains were converted to the singly PEGylated product (FIG. 5C, lane 6), as indicated by optical densitometry. This yield likely results from the close proximity of the two N-termini in the intact Fc domains, resulting in the attachment of only one PEG chain to each protein dimer. Nonetheless, a high degree of modification was observed using very short coupling times.

Figure 5D:
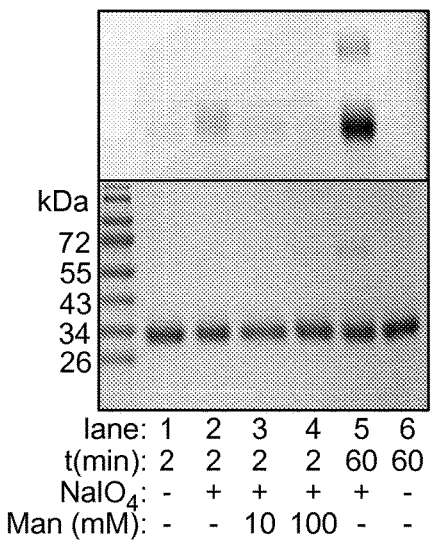

As one potential concern with this strategy, immunoglobulin proteins contain oligosaccharides, which could be cleaved to form aldehydes in the presence of sodium periodate. To determine to what degree this occurs, unmodified Fc domains were exposed to $NaIO_4$ under the oxidative coupling conditions for 2 min and 1 h. The resulting aldehyde groups were then visualized by subsequent reaction with AlexaFluor 488 alkoxyamine (4b). As seen in FIG. 5D, the oligosaccharides on the Fc protein were only minimally oxidized by $NaIO_4$ at the 2 min time point (compare lanes 2 and 5 to the background labeling for unmodified Fc in lane 1). Furthermore, it was found that the addition of 10 mM to 100 mM mannose could suppress this oxidation of the carbohydrate groups completely. Interestingly, the oxidative coupling reaction still proceeded with similar conversion in the presence of 10 mM mannose (FIG. 5C, lane 7), and with somewhat reduced conversion in the presence of 100 mM mannose (lane 8). Thus, this strategy provides a method to protect glycoproteins from undesired oxidation with this procedure. Even though it should be noted that the Fc protein examined here does not contain sialic acids, which are the most susceptible to oxidation, it is anticipated that oxidative coupling will still occur in a much shorter timescale in comparison to oxidation of oligosaccharides.

FIGS. 5A-D. Modification of Fc domains via oxidative coupling (O.C.). AKT-Fc (1) was exposed to 25 mM 8 for 40 h at pH 4.5, followed by PNGaseF treatment (a) without prior transamination with PLP (as a negative control), or (b) following transamination with 100 mM PLP at 37° C. for 1 h. The peak at 52315 Da corresponded to unmodified AKT-Fc (expected: 52315 Da). The double-oxime product (9) appeared at 52697 Da (expected: 52695 Da), and the peak at 52944 Da corresponded to product 9 plus a single PLP addition (expected: 52942 Da). The peak at 52506 Da corresponded to the addition of one molecule of 8 to the AKT-Fc fragment (13, expected: 52506 Da). (c) Samples of unmodified Fc (1) and Fc-aniline (9) were exposed to 100 µM 2k PEG-aminophenol (10a) and 1 mM $NaIO_4$ for 2 min at RT. Lanes 1-5 display negative controls. Only in the presence of both aniline on the Fc and $NaIO_4$ did the attachment of 2 k PEG-aminophenol occur (lane 6). In the presence of 10 mM mannose (lane 7), the O.C. still proceeded; however, the yield suffered when the mannose concentration was increased to 100 mM (lane 8). (d) The extent of oxidation of the oligosaccharides on the Fc protein within the reaction time of the O.C. was analyzed. The Fc proteins were exposed to 1 mM $NaIO_4$ for 2 and 60 min. The reaction was stopped upon addition of TCEP and any aldehydes formed from the oxidation were then detected by Alexafluor 488-$ONH_2$. The fluorescent images of Fc-AlexaFluor488 oxime products (top) were taken using a Typhoon imaging system. The oligosaccharides on the Fc were minimally oxidized under the O.C. reaction time of 2 min (lane 2) and this oxidation was lowered to background level upon addition of 10 mM mannose or higher concentration (lanes 3 and 4). The oxidation of oligosaccharides on Fc with $NaIO_4$ for 1 h was shown as a positive control (lane 5). Lane 1 and 6 display the background level of oxidized sugar in the absence of $NaIO_4$.

Since the 1990s, small RNA and DNA aptamers have emerged as a new class of molecules for therapeutic and diagnostic purposes, owing to the successful development of the systematic evolution of ligands by an exponential enrichment process, known as SELEX.[7,19] Using SELEX, new aptamers can be evolved to bind to cells with high specificity and affinity, often without prior knowledge of the specific molecular targets. These readily evolved binding groups could endow Fc domains with specific cell binding abilities, and, conversely, the Fc domains could improve the in vivo circulation times of the oligonucleotides, as shown by Barbas et al.[6a] Two aptamers were selected for attachment to the Fc proteins as a proof of principle for the production of Fc-synthetic molecule hybrids: (1) sgc8c, which targets protein tyrosine kinase 7 (PTK7)[20] and (2) TD05.1, which targets membrane-bound IgM (mIgM, also known as the B-cell receptor).[21] The sgc8c aptamer has been used in many applications[22,17c] and shown high specificity to its target. The use of TD05.1 could be advantageous because there is currently no antibody that is specific to binding mIgM without also binding to circulating IgM in the blood.[21] For use as a negative control in cell binding experiments, a scrambled 41-nucleotide DNA sequence (M2M2) was also attached to Fc.

Figure 6A:
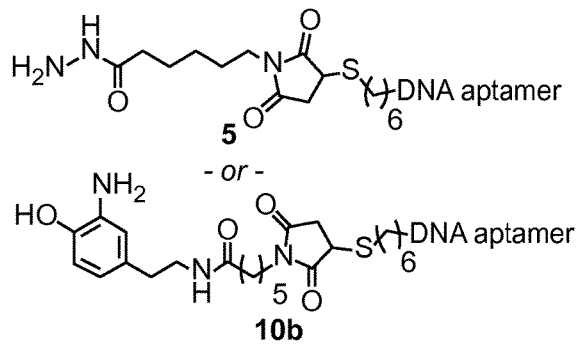
FIGS. 6A-D depict construction of Fc-aptamer conjugates.
Figure 6C:
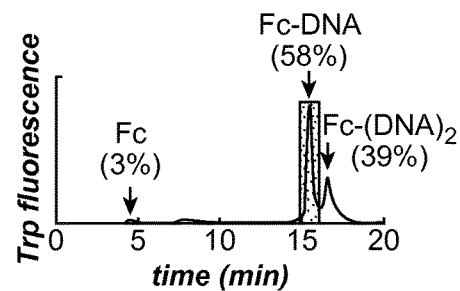
Figure 6B:
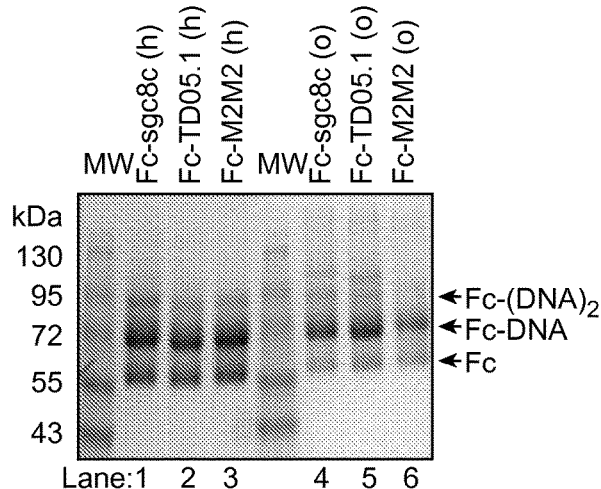
Figure 6D:
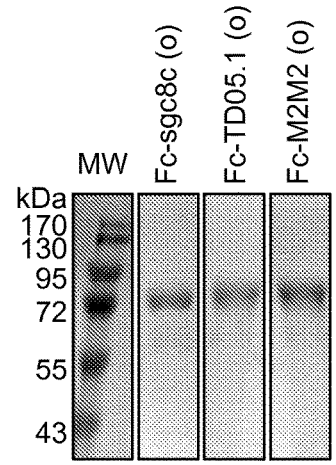

Using the hydrazone formation strategy with 100 µM hydrazide-oligonucleotides (5) and 100 mM aniline as a coupling catalyst[23] over a 48 h period, the Fc-aptamer conjugates could be obtained as identified by SDS-PAGE analysis (FIG. 6B). Due to the high negative charge of the DNA portion, the Fc conjugates could also be separated using anion exchange chromatography (FIG. 6C), allowing more accurate determination of the product ratios. The major product (64%) possessed a single attachment of the oligonucleotide to one of the Fc N-termini, likely due to steric hindrance and electronic repulsion between two DNA molecules. The doubly modified product corresponded to 20% yield, with only 16% of unconjugated Fc protein remaining. The alternative method, the attachment of aminophenol-DNA oligonucleotides (10b, 100 µM) to Fc-aniline (9) via oxidative coupling reaction, was achieved at RT in 2 min. In this case, 58% of the protein product corresponded to the single aptamer conjugate and 39% corresponded to the double aptamer conjugate, representing a total of >95% of the protein species. The overall yields were therefore slightly higher than those achieved by direct hydrazone formation (FIG. 6A, lanes 4-6), but they were obtained with drastically reduced coupling times. Anion exchange chromatography was again used to obtain pure conjugates for use in subsequent binding studies, FIG. 6D.

FIGS. 6A-D. Construction of Fc-aptamer conjugates. Two different aptamers, sgc8c targeting PTK7 and TD05.1 targeting membrane-bound IgM, were attached to keto-Fc using the two approaches shown in FIG. 1. (a) Structure of hydrazide- and aminophenol-DNA oligonucleotides used for hydrazone formation and the oxidative coupling reaction, respectively. (b) SDS-PAGE analysis under non-reducing conditions showed the formation of Fc hybrids using either hydrazone formation (labeled as 'h', lanes 1-3) or oxidative coupling ('o', lanes 4-6). Single aptamer conjugates were the major products, along with lesser amounts of doubly-labeled conjugated species. (c) Anion exchange-HPLC analysis of the crude Fc-TD05.1 adduct following the oxidative coupling reaction, indicating the relative quantities of Fc, Fc-DNA, and Fc-(DNA). The shaded fraction was 2 collected for further use. (d) SDS-PAGE analysis (non-reducing) of the purified Fc-aptamer conjugates used for cell binding analysis.

The specificities of Fc-sgc8c, Fc-TD05.1, and Fc-M2M2 hybrid constructs generated from both the hydrazone and the oxidative coupling strategies were next evaluated for selective cell binding using flow cytometry. Jurkat cells, a T-cell leukemia cell line overexpressing PTK7, were used as the targeted cells for the Fc-sgc8c constructs. Ramos cells, a Burkitt's lymphoma cell line overexpressing mIgM, were used as target cells for Fc-TD05.1. U266 cells, a B-cell line overexpressing neither membrane protein, were chosen as a negative control sample. The binding assay was conducted as outlined in FIG. 7A, with detection of the cell-bound Fc conjugates using fluorescently labeled anti-human IgG1.

Figure 7A:
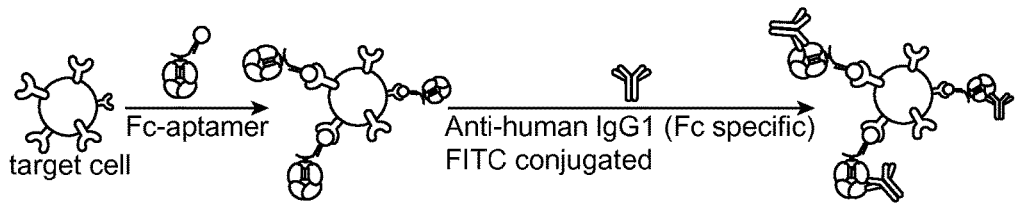
FIGS. 7A-D depict cell binding specificity and C1q binding ability of Fc-aptamer conjugates.
Figure 7B:
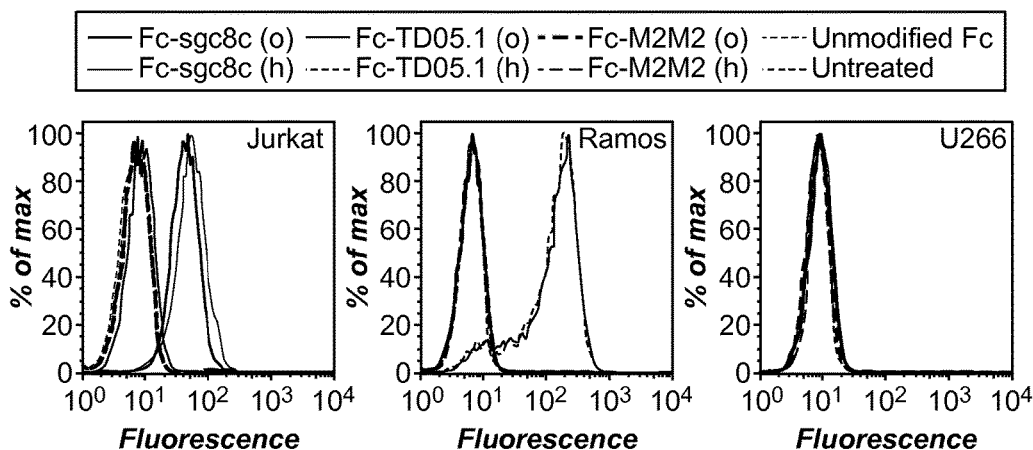
Figure 7C:
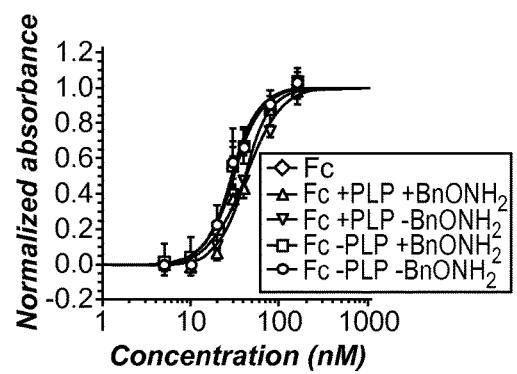

Only Jurkat cells were bound by Fc-sgc8c, and only Ramos cells were recognized by Fc-TD05.1 (FIG. 7B). Neither cell line was recognized by Fc-M2M2. Moreover, the U266 negative control cell line did not bind to any of the Fc-aptamer constructs. In addition to confirming that the aptamers retained their specificity after attachment to the Fc domains, these results also indicated that the Fc region retained its proper folding and thus could still be recognized by the fluorescent secondary antibodies.

FIGS. 7A-D. Cell binding specificity and C1q binding ability of Fc-aptamer conjugates. (a) The general cell binding analysis scheme is shown. The cells were incubated with Fc-aptamer samples, which were subsequently detected using FITC-labeled secondary antibodies specific for Fc of human IgG1. (b) Flow cytometry data are shown for the binding of Fc-aptamer conjugates to Jurkat cells (overexpressing PTK7, the target of the sgc8c aptamer, ref 20), Ramos cells (overexpressing membrane-bound IgM, the target for the TD05.1 aptamer, ref 21), and U266 cells as a negative control. All Fc-sgc8c and Fc-TD05.1 conjugates retained their targeting specificity, whether they were generated using hydrazone formation (labeled 'h') or oxidative coupling (labeled 'o'). Unmodified Fc proteins and an Fc-M2M2 conjugate (bearing a scrambled 41-base oligonucleotide) did not bind to any cell lines. (c) ELISA data are shown for C1q binding to unmodified Fc, PLP-treated Fc, and Fc after oxime formation with BnONH. (d) ELISA data are shown for C1q binding to the 2 Fc-aptamer conjugates used in (b).

Figure 7D:
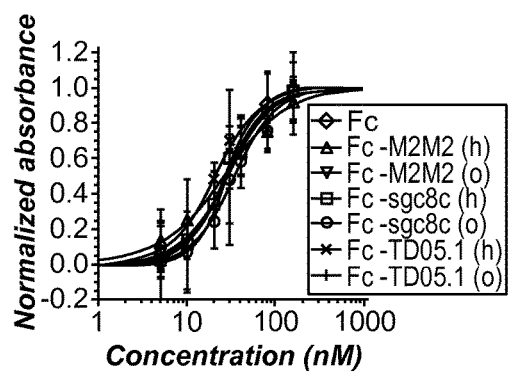

A key feature associated with the toxicity of many antibodies is the recruitment of complement proteins found in blood serum. The ability of the modified Fc proteins to bind to the C1q complement protein was evaluated using ELISA.[24] Briefly, varying concentrations of the Fc conjugates were bound to a polystyrene 96-well plate, after which a 2 µg/mL solution of human C1q was added. Binding ability was confirmed using an anti-C1q antibody conjugated to horseradish peroxidase (HRP). These results showed that the PLP-treated Fc and Fc-aptamer constructs still retained their ability to bind to C1q with similar affinities. This suggests that the bulk of the immunological activating properties of the Fc domains remained intact following the modification process (FIGS. 7A and 7D).

REFERENCES 1. (a) Walsh, G. Nat. Biotechnol. 2010, 28, 917-924. (b) Carter, P. J. Exp. Cell Research 2011, 317, 1261-9. (c) Huang, C. Curr. Opin. Biotechnol. 2009, 20, 692-699.
2. (a) Roopenian, D. C.; Akilesh, S. Nat. Rev. Immunol. 2007, 7, 715-725. (b) Ghetie, V.; Ward, E. S. Ann. Rev. Immunol. 2000, 18, 739-766.
3. (a) Iannello, A.; Ahmad, A. Cancer Metastasis Rev. 2005, 24, 487-499. (b) Gelderman, K. A.; Tomlinson, S.; Ross, G. D.; Gorter, A. Trends in Immunology 2004, 25, 158-164. (c) Shields, R. L.; Namenuk, A. K.; Hong, K.; Meng, Y. G.; Rae, J.; Briggs, J.; Xie, D.; Lai, J.; Stadlen, A.; Li, B.; Fox, J. A.; Presta, L. G. J. Biol. Chem. 2001, 276, 6591-6604. (d) Clynes, R. A.; Towers, T. L.; Presta, L. G.; Ravetch, J. V. Nat. Med. 2000, 6, 443-446.
4. (a) Yokota, T.; Milenic, D. E.; Whitlow, M.; Schlom, J. Cancer Res. 1992, 52, 3402-3408. (b) Hicke, B. J.; Stephens, A. W.; Gould, T.; Chang, Y.-F.; Lynott, C. K.; Heil, J.; Borkowski, S.; Hilger, C.-S.; Cook, G.; Warren, S.; Schmidt, P. G. J. Nucl. Med. 2006, 47, 668-678.
5. (a) Low, S. C.; Nunes, S. L.; Bitonti, A. J.; Dumont, J. A. Hum. Reprod. 2005, 20, 1805-1813. (b) Bitonti, A. J.; Dumont, J. A.; Low, S. C.; Peters, R. T.; Kropp, K. E.; Palombella, V. J.; Stattel, J. M.; Lu, Y.; Tan, C. A.; Song, J. J.; Garcia, A. M.; Simister, N. E.; Spiekermann, G. M.; Lencer, W. I.; Blumberg, R. S. Proc. Natl. Acad. Sci. U.S.A. 2004, 101, 9763-9768.
6. (a) Wuellner, U.; Gavrilyuk, J. I.; Barbas III, C. F. Angew. Chem. Int. Ed. Engl. 2010, 49, 5934-5937. (b) Rader, C.; Sinha, S. C.; Popkov, M.; Lerner, R. A.; Barbas III, C. F. Proc. Natl. Acad. Sci. 2003, 100, 5396-5400.
7. (a) Ellington, A. D.; Szostak, J. W. Nature 1990, 346, 818-822. (b) Tuerk, C.; Gold, L. Science 1990, 249, 505-510.
8. Zuckermann, R. N.; Kodadek, T. Curr. Opin. Mol. Ther. 2009, 11, 299-307.
9. Shaunak, S.; Godwin, A.; Choi, J.; Balan, S.; Pedone, E.; Vijayarangam, D., Heidelberger, S.; Teo, I.; Zloh, M.; Brocchini, S. Nat. Chem. Biol. 2006, 2, 312-313.
10. Junutula J. R., Raab, H.; Clark, S.; Bhakta, S.; Leipold, D. D.; Weir, S.; Chen, Y.; Simpson, M.; Tsai, S. P.; Dennis, M. S.; Lu, Y.; Meng, Y. G.; Ng, C.; Yang, J.; Lee, C. C.; Duenas, E.; Gorrell, J.; Katta, V.; Kim, A.; McDorman, K.; Flagella, K.; Venook, R.; Ross, S.; Spencer, S. D.; Wong, W. L.; Lowman, H. B.; Vandlen, R.; Sliwkowski, M. X.; Scheller, R. H.; Polakis, P.; and Mallet, W. Nat. Biotech. 2008, 26, 925-932.
11. Xiao, J.; Chen, R.; Pawlicki, M. A.; Tolbert, T. J. J. Am. Chem. Soc. 2009, 131, 13616-13618.
12. Wu, P., Shui, W.; Carlson, B. L.; Hu, N.; Rabuka, D.; Lee, J.; Bertozzi, C. R. Proc. Nat. Acad. Sci. USA. 2009, 106, 3000-3005.
13. Hofer, T; Thomas, J. D.; Burke, T. R.; Rader, C. Hofer, T.; Thomas, J. D.; Burke, T. R.; Rader, C. Proc. Nat. Acad. Sci. USA. 2008, 105, 12451-12456.
14. (a) Hutchins, B. M.; Kazane, S. A.; Staflin, K.; Forsyth, J. S.; Felding-Habermann, B.; Schultz, P. G.; Smider, V. V. J. Mol. Biol. 2011, 406, 595-603. (b) Hutchins, B. M.; Kazane, S. A.; Staflin, K.; Forsyth, J. S.; Felding-Habermann, B.; Smider, V. V.; Schultz, P. G. Chem. Biol. 2011, 18, 299-303.
15. (a) Gilmore, J. M.; Scheck, R. A.; Esser-Kahn, A. P.; Joshi, N. S.; Francis, M. B. Angew. Chem. Int. Ed. 2006, 45, 5307-5311. (b) Scheck, R. A.; Francis, M. B. ACS Chem. Biol. 2007, 2, 247-251. (c) Scheck, R. A.; Dedeo, M. T.; Iavarone, A. T.; Francis, M. B. J. Am. Chem. Soc. 2008, 130, 11762-11770. (d) Witus, L. S.; Moore, T.; Thuronyi, B. W.; Esser-Kahn, A. P.; Scheck, R. A.; Iavarone, A. T.; Francis, M. B. J. Am. Chem. Soc. 2010, 132, 16812-16817. For previous studies of transamination with PLP, see (e) Snell, E. E. J. Am. Chem. Soc. 1945, 67, 194-197. (f) Dixon, H. B. F. J. Protein Chem. 1984, 3, 99-108. (g) Dixon, H. B. F.; Fields, R. Methods Enzymol. 1972, 25, 409-419.
16. (a) Jencks, W. P. J. Am. Chem. Soc. 1959, 81, 475-481. (b) Cornish, V. W.; Hahn, K. M.; Schultz, P. G. J. Am. Chem. Soc. 1996, 118, 8150-8151. (c) Mahal, L. K.; Yarema, K. J.; Bertozzi, C. R. Science 1997, 276, 1125-1128. (d) Kalia, J.; Raines, R. Angew. Chem. Int. Ed. 2008, 47, 7523-7526.
17. (a) Hooker, J. M.; Esser-Kahn, A. P.; Francis, M. B. J. Am. Chem. Soc. 2006, 128, 15558-15559. (b) Behrens, C. R.; Hooker, J. M.; Obermeyer, A. C.; Romanini, D. W.; Katz, E. M.; Francis, M. B. J. Am. Chem. Soc. 2011, 133, 16398-16401. (c) Tong, G. J.; Hsiao, S. C.; Carrico, Z. M.; Francis, M. B. J. Am. Chem. Soc. 2009, 131, 11174-11178.
18. For examples of other bioconjugation reactions involving sodium periodate, see: (a) Geoghegan, K. F.; Stroh, J. G. Bioconj. Chem. 1992, 3, 138-146. (b) Liu, B.; Burdine, L.; Kodadek, T. J. Am. Chem. Soc. 2006, 128, 15228-15235.

19. (a) Fang, X.; Tan, W. *Acc. Chem. Res.* 2010, 43, 48-57. (b) Keefe, A. D.; Pai, S.; Ellington, A. *Nat. Rev. Drug Discov.* 2010, 9, 537-550. (c) Jayasena, S. D. *Clin. Chem.* 1999, 45, 1628-1650. (d) Nimjee, S. M.; Rusconi, C. P.; Sullenger, B. A. *Ann. Rev. Med.* 2005, 56, 555-583. (e) Bouchard, P. R.; Hutabarat, R. M.; Thompson, K. M. *Ann. Rev. Pharm. Tox.* 2010, 50, 237-257.

20. (a) Shangguan, D.; Li, Y.; Tang, Z.; Cao, Z. C.; Chen, H. W.; Mallikaratchy, P.; Sefah, K.; Yang, C. J.; Tan, W. *Proc. Natl. Acad. Sci.* 2006, 103, 11838-11843. (b) Shangguan, D.; Tang, Z.; Mallikaratchy, P.; Xiao, Z.; Tan, W. *Chembiochem* 2007, 8, 603-606. (c) Shangguan, D.; Cao, Z.; Meng, L.; Mallikaratchy, P.; Sefah, K.; Wang, H.; Li, Y.; Tan, W. *J. Proteome Res.* 2008, 7, 2133-2139.

21. (a) Mallikaratchy, P.; Tang, Z.; Kwame, S.; Meng, L.; Shangguan, D.; Tan, W. *Mol. Cell. Proteomics* 2007, 6, 2230-2238. (b) Mallikaratchy, P. R.; Ruggiero, A.; Gardner, J. R.; Kuryavyi, V.; Maguire, W. F.; Heaney, M. L.; McDevitt, M. R.; Patel, D. J.; Scheinberg, D. A. *Nucl. Acids Res.* 2011, 39, 2458-2469.

22. (a) Shi, H.; He, X.; Wang, K.; Wu, X.; Ye, X.; Guo, Q.; Tan, W.; Qing, Z.; Yang, X.; Zhou, B. *Proc. Natl. Acad. Sci. U.S.A.* 2011, 108, 3900-3905. (b) Douglas, S. M.; Bachelet, I.; Church, G. M. *Science* 2012, 335, 831-834. (c) Luo, Y.-L.; Shiao, Y.-S.; Huang, Y.-F. *ACS Nano* 2011, 5, 7796-7804. (d) Stephanopoulos, N.; Tong, G. J.; Hsiao, S. C.; Francis, M. B. *ACS Nano* 2010, 4, 6014-6020.

23. (a) Dirksen, A.; Hackeng, T. M.; Dawson, P. E. *Angew. Chem. Int. Ed.* 2006, 45, 7581-7584. (b) Dirksen, A.; Dirksen, S.; Hackeng, T. M.; Dawson, P. E. *J. Am. Chem. Soc.* 2006, 128, 15602-15603.

24. Idusogie, E. E.; Presta, L. G.; Totpal, K.; Wong, P. Y.; Meng, Y. G.; Mulkerrin, M. G.; Alerts, E. *J. Immunol.* 2000, 164, 4178-4184.

Example 2: Preparation and Characterization of Antibody Conjugates

Anti-HER2 human IgG1 antibodies were functionalized with DNA aptamers both through N-terminal modification and through lysine modification. The binding specificity of antibody-DNA aptamer conjugates was determined by flow cytometry.

Construction of Light Chain Anti-HER2 Human IgG1 Expression Plasmids.

To clone a plasmid for the expression of the anti-HER2 human IgG1 light chain, the sequence for the variable domain of the light chain ($V_L$) was obtained from the literature, assembled into a gene, then cloned into a plasmid containing the light chain constant region. Gene2Oligo was used to generate the following set of oligonucleotides for gene assembly from the $V_L$ sequence. An IL2 signaling sequence was also included in the N-terminal region. The bases in lower case were added by the Gene2Oligo program and did not belong to the input sequence:

R0:
(SEQ ID NO: 30)
ACCTTTTTTTacattgaagtgcag;

F0:
(SEQ ID NO: 31)
ctgcacttcaatgtAAAAAAAGGTCACCATGTACAGGATGCA;

R24:
(SEQ ID NO: 32)
GCAATGCAAGACAGGAGTTGCATCCTGTACATGGTG;

F42:
(SEQ ID NO: 33)
ACTCCTGTCTTGCATTGCACTAAGTCTTGCACTTGTCA;

R60:
(SEQ ID NO: 34)
TCAGTCTTAGCCGAATTCGTGACAAGTGCAAGACTTAGT;

F80:
(SEQ ID NO: 35)
CGAATTCGGCTAAGACTGACATCCAAATGACTCAGAGCC;

R99:
(SEQ ID NO: 36)
GCGCTCAGGGAACTGGGGCTCTGAGTCATTTGGATG;

F119:
(SEQ ID NO: 37)
CCAGTTCCCTGAGCGCTTCCGTAGGGGACAGG;

R135:
(SEQ ID NO: 38)
GCCCGACATGTTATTGTCACCCTGTCCCCTACGGAA;

F151:
(SEQ ID NO: 39)
GTGACAATAACATGTCGGGCTAGCCAGGATGTCAATACAG;

R171:
(SEQ ID NO: 40)
CTGGTACCAAGCGACAGCTGTATTGACATCCTGGCTA;

F191:
(SEQ ID NO: 41)
CTGTCGCTTGGTACCAGCAAAAGCCCGGAAAGGC;

R208:
(SEQ ID NO: 42)
GCTGTATATAAGAAGCTTTGGCGCCTTTCCGGGCTTTTG;

F225:
(SEQ ID NO: 43)
GCCAAAGCTTCTTATATACAGCGCCAGTTTCCTCTATTCTGG;

R247:
(SEQ ID NO: 44)
GAACCTGCTCGGCACGCCAGAATAGAGGAAACTGGC;

F267:
(SEQ ID NO: 45)
CGTGCCGAGCAGGTTCTCTGGATCTCGGTCCG;

R283:
(SEQ ID NO: 46)
TCAGTGTGAAATCGGTCCCGGACCGAGATCCAGA;

F299:
(SEQ ID NO: 47)
GGACCGATTTCACACTGACCATTAGTTCTCTGCAGCC;

R317:
(SEQ ID NO: 48)
TAGTATGTTGCAAAGTCCTCTGGCTGCAGAGAACTAATGG;

F336:
(SEQ ID NO: 49)
AGAGGACTTTGCAACATACTACTGCCAGCAGCACTAT;

R357:
(SEQ ID NO: 50)
AGGTTGGGGGTGTGGTATAGTGCTGCTGGCAG;

F373:
(SEQ ID NO: 51)
ACCACACCCCCAACCTTTGGTCAGGGCACGAA;

R389:
(SEQ ID NO: 52)
CGTACGCTTGATTTCCACCTTCGTGCCCTGACCAA;

F405:
(SEQ ID NO: 53)
GGTGGAAATCAAGCGTACGAAAAAAAccccaactttgt;

F424:
(SEQ ID NO: 54)
acaaagttgggggTTTTTTT.

An additional GCTAAAACT was added to the 5' end in order to create a three residue N-terminal extension (AKT). The resulting $V_L$ gene was inserted into a vector at BsiWI and BstEII restriction sites using standard cloning techniques. The vector used, pFUSE2-CLIg-hk from Invivogen (San Diego, Calif.), already contained the constant region of the kappa light chain.

Construction of Heavy Chain Anti-HER2 Human IgG1 Expression Plasmids.

A plasmid for the expression of the anti-HER2 heavy chain was cloned in a similar fashion to that of light chain. In brief, the variable and constant region 1 of heavy chain ($V_H$ and $C_H 1$) was constructed from the following set of oligonucleotides with additional bases (CTCCAAACA) at the 5' end (corresponding to three N-terminal residues, LQT, for use in other work and later mutated to AKT for this work).

R0:
(SEQ ID NO: 55)
TTTTTTTcttagctgctttga;

F0:
(SEQ ID NO: 56)
tcaaagcagctaagAAAAAAAGAATTCGCTCCAAACAG;

R21:
(SEQ ID NO: 57)
CGACGAGTTGGACTTCTGTTTGGAGCGAATTC;

F38:
(SEQ ID NO: 58)
AAGTCCAACTCGTCGAAAGCGGAGGTGGC;

R53:
(SEQ ID NO: 59)
CCAGGCTGAACCAGGCCACCTCCGCTTT;

F67:
(SEQ ID NO: 60)
CTGGTTCAGCCTGGCGGAAGCCTGCGC;

R81:
(SEQ ID NO: 61)
GCAGCACAGCTCAAGCGCAGGCTTCCG;

F94:
(SEQ ID NO: 62)
TTGAGCTGTGCTGCCTCCGGATTTAATATCAAAGA;

R108:
(SEQ ID NO: 63)
CGAACCCAGTGTATATAAGTATCTTTGATATTAAATCCGGAG;

F129:
(SEQ ID NO: 64)
TACTTATATACACTGGGTTCGCCAGGCTCCTGGA;

R150:
(SEQ ID NO: 65)
CCACTCCAGACCCTTTCCAGGAGCCTGG;

F163:
(SEQ ID NO: 66)
AAGGGTCTGGAGTGGGTGGCGAGAATCTACC;

R178:
(SEQ ID NO: 67)
GGGTATAACCATTGGTTGGGTAGATTCTCGCCAC;

F194:
(SEQ ID NO: 68)
CAACCAATGGTTATACCCGCTATGCAGACAGCG;

R212:
(SEQ ID NO: 69)
GTAAACCGCCCTTTCACGCTGTCTGCATAGC;

F227:
(SEQ ID NO: 70)
TGAAAGGGCGGTTTACAATTAGTGCCGACACA;

R243:
(SEQ ID NO: 71)
GGTAAGCGGTATTTTTAGATGTGTCGGCACTAATT;

F259:
(SEQ ID NO: 72)
TCTAAAAATACCGCTTACCTCCAGATGAACTCTCTG;

R278:
(SEQ ID NO: 73)
TGTCCTCGGCCCTCAGAGAGTTCATCTGGA;

F295:
(SEQ ID NO: 74)
AGGGCCGAGGACACGGCTGTGTATTATTGC;

R308:
(SEQ ID NO: 75)
CACCCCACCGGCTGCAATAATACACAGCCG;

F325:
(SEQ ID NO: 76)
AGCCGGTGGGGTGGAGACGGATTCTATGCT;

R338:
(SEQ ID NO: 77)
TGACCCCAATAGTCCATAGCATAGAATCCGTCTC;

F355:
(SEQ ID NO: 78)
ATGGACTATTGGGGTCAGGGCACTCTCGTCA;

R372:
(SEQ ID NO: 79)
TGGCACTGCTTACAGTGACGAGAGTGCCC;

F386:
(SEQ ID NO: 80)
CTGTAAGCAGTGCCAGCACAAAGGGGCC;

R401:
(SEQ ID NO: 81)
CAAGGGGAAAGACACTAGGCCCCTTTGTGC;

F414:
(SEQ ID NO: 82)
TAGTGTCTTTCCCCTTGCTCCATCTAGCAAATCTAC;

R431:
(SEQ ID NO: 83)
GGTGCCCCCGCTGGTAGATTTGCTAGATGGAG;

F450:
(SEQ ID NO: 84)
CAGCGGGGCACCGCCGCCCTGGGAT;

R463:
(SEQ ID NO: 85)
GTCCTTGACCAGGCATCCCAGGGCGGC;

F476:
GCCTGGTCAAGGACTATTTTCCTGAGCCAGT; (SEQ ID NO: 86)

R490:
TCCAGGACACGGTGACTGGCTCAGGAAAATA; (SEQ ID NO: 87)

F507:
CACCGTGTCCTGGAATAGTGGCGCCTTGA; (SEQ ID NO: 88)

R521:
TGTGTGAACACCAGAAGTCAAGGCGCCACTAT; (SEQ ID NO: 89)

F536:
CTTCTGGTGTTCACACATTTCCCGCCGTCC; (SEQ ID NO: 90)

R553:
CAGCCCACTAGATTGAAGGACGGCGGGAAA; (SEQ ID NO: 91)

F566:
TTCAATCTAGTGGGCTGTACTCTCTCTCCAGTGT; (SEQ ID NO: 92)

R583:
TGGGTACCGTCACCACACTGGAGAGAGAGTA; (SEQ ID NO: 93)

F600:
GGTGACGGTACCCAGTTCAAGCTTGGGCA; (SEQ ID NO: 94)

R614:
TGCAGATATAGGTCTGTGTGCCCAAGCTTGAAC; (SEQ ID NO: 95)

F629:
CACAGACCTATATCTGCAATGTGAACCACAAGCC; (SEQ ID NO: 96)

R647:
CCACCTTTGTATTGCTGGGCTTGTGGTTCACAT; (SEQ ID NO: 97)

F663:
CAGCAATACAAAGGTGGACAAAAAAGTCGAGCCT; (SEQ ID NO: 98)

R680:
TGTCACAGCTCTTTGGAGGCTCGACTTTTTTGT; (SEQ ID NO: 99)

F697:
CCAAAGAGCTGTGACAAAACTCACACATGCCC; (SEQ ID NO: 100)

R713:
TACCTGGGCACGGTGGGCATGTGTGAGTTT; (SEQ ID NO: 101)

F729:
ACCGTGCCCAGGTAAGCCAGCCCAGGC; (SEQ ID NO: 102)

R743:
ccccattgactTTTTTTTAGGCCTGGGCTGGCT; (SEQ ID NO: 103)

R756:
CTAAAAAAAgtcaatgggg. (SEQ ID NO: 104)

The BglII site was introduced using PCR with forward primer F0 and a reverse primer containing a BglII restriction site (sequences shown below). Forward: tcaaagca-gctaagAAAAAAAGAATTCGCTCCAAACAG (SEQ ID NO:56); Reverse: tttttttAGATCTCTTTGGAGGCTC-GACTTTTTTGT (SEQ ID NO:105).

The gene encoding $V_H$ and $C_H1$ was inserted into a vector comprising the crystallizable fragment (Fc) domain (i.e. $C_H2$ and $C_H3$ domains) of human IgG1 heavy chain (pin-fuse-higG1-fc2 from Invivogen) at the EcoRI and BglII restriction sites. A Quikchange site-directed mutagenesis kit was used to generate the desired AKT N-terminal mutant. Incorporation of these mutations was verified by sequencing.

Procedure for Expression and Purification of Mutant Antibodies

The plasmids for the light and heavy chains of the anti-HER2 antibody were transiently co-transfected into human embryonic kidney 293T cells in a 3:2 ratio using lipofectamine 2000 (Invitrogen, Grand Island, N.Y.) in Opti-MEM medium following the protocol from Invitrogen. The cells were incubated at 37° C. in 5% $CO_2$. After two days, the media was collected and the secreted antibodies were purified using protein G affinity chromatography, according to the procedure from the manufacturer (Pierce, Rockford, Ill.). The media was replaced and cultures were grown for an additional 3 days, after which the additional antibodies were harvested and purified as above. Purified protein was buffer exchanged into PBS using Amicon Ultra 4 mL 10,000 MWCO (Millipore) centrifugal ultrafiltration membranes. Purity was evaluated by SDS-PAGE with Coomassie staining.

Procedure for PLP N-Terminal Transamination

The 2× protein stock solutions were prepared at 1-40 µM using 25 mM phosphate buffer at pH 6.5. The 2× (200 mM) PLP stock solutions were prepared in 25 mM phosphate buffer and the pH of the solution was adjusted to 6.5 using NaOH solution. Protein and PLP stock solutions were mixed in equal volumes. The reaction mixture was briefly agitated to ensure mixing and then incubated without further agitation at 37° C. for 1 h. After incubation, the PLP was removed using NAP Sephadex size exclusion columns (GE Healthcare). The resulting keto-antibody solution was then concentrated and the buffer was exchanged with 25 mM phosphate buffer (pH 6.5), using Millipore 0.5 or 4 mL spin concentrators (MWCO 10 kDa), following the protocol from the manufacturer.

Procedure for Hydrazone and Oxime Formation

The reaction was performed with 1-40 µM keto-antibody and $RONH_2$ or $R(CO)NHNH_2$ at varied concentrations. For the analysis of PLP transamination efficiency, $BnONH_2$ were added to keto-antibody to a final concentration of 100 mM. For the attachment of an oxidative coupling partner, aniline-$ONH_2$ was added to a final concentration of 25 mM. The reaction mixture was incubated at RT for 18-50 h. All the reactions were carried out in 25 mM phosphate buffer (pH 6.5), except for oxime formation with aniline-$ONH_2$, which was done in 25 mM phosphate buffer (pH 5). Following the reaction, the small molecules were removed using NAP Sephadex size exclusion columns (GE Healthcare) and the resulting product mixtures were concentrated using Millipore 0.5 or 4 mL spin concentrators (MWCO 10 kDa), following the protocol from the manufacturer. The percent reaction conversion for the antibody samples with small molecules was analyzed using LCMS.

Procedure for Lysine Modification

The reaction was performed with 1-40 µM antibody in phosphate buffer pH 8 and R—NHS ester at varied concentrations. To make antibody-aniline conjugates, a mixture of 3-(4-aminophenyl) propionic acid, N-hydroxysuccinimide, and 1-ethyl-3-(3-dimethylaminopropyl)carbodiimide was added to the wild-type antibody to a final concentration of 2.5 mM, and the solution was incubated at RT for 1 h. The reaction was quenched upon adding excess hydroxylamine and the small molecules were removed using NAP Sephadex size exclusion columns (GE Healthcare). The resulting antibody-aniline conjugates were concentrated using Millipore 0.5 or 4 mL spin concentrators (MWCO 10 kDa).

Procedure for Oxidative Coupling

To a solution of 1-40 µM antibody-aniline in 25 mM phosphate buffer (pH 6.5) was added a solution of 5-100 equivalents of aminophenol-aptamer or aminophenol-2k PEG. Sodium periodate (Sigma-Aldrich) was dissolved to a concentration of 10 mM in 25 mM phosphate buffer (pH 6.5). The sodium periodate was then added to the reaction mixture to reach a final concentration of 1 mM, and the reaction was allowed to proceed for 2-5 min at RT. In some cases, a solution of mannose was also added to a final concentration of 10 mM or 100 mM before addition of the periodate solution. The resulting protein samples were purified on NAP Sephadex size exclusion columns (GE Healthcare) and concentrated using Millipore 0.5 or 4 mL spin concentrators (MWCO 10 kDa), following the protocol from the manufacturer.

Purification of Antibody-Aptamer Constructs

The resulting antibody-DNA conjugates from both N-terminal and lysine modification were purified from unreacted DNA using sized exclusion FPLC and the fractions containing antibody-DNA constructs were combined and concentrated using Millipore 0.5 or 4 mL spin concentrators (MWCO 10 kDa).

Flow Cytometry Experiments

Flow cytometry was used to determine binding ability of all the antibody-aptamer constructs. For all samples, 100 µL of 1-3×10$^6$ cells/mL of Jurkat, Ramos, and MCF7 clone 18 were used, suspended in binding buffer (4.5 g/L glucose, 5 mM MgCl$_2$, 0.1 mg/mL yeast tRNA (Sigma) and 1 mg/mL BSA (Fisher) in Dulbecco's PBS with calcium chloride and magnesium chloride (Invitrogen)). To these cells were added 10 µL of a series of 2-200 nM antibody-aptamer construct solutions. The samples were then incubated on ice for 45 min. The resulting cells were washed with 500 µL of binding buffer and resuspended in an additional 100 µL of binding buffer. Anti-human IgG1 antibody (specific for the Fc domain) with FITC conjugated (Sigma) was then added to a final concentration of ~0.30 µM. Cells were incubated for 30 min on ice in the dark, then washed with 500 µL of binding buffer, and resuspended in 200 µL binding buffer. The cells were analyzed by flow cytometry to determine the amount of FITC fluorescence. For each sample, 10,000 cells were counted.

Results

The results are depicted in FIGS. 11A and 11B, and in FIGS. 12A and 12B.

Anti-HER2 human IgG1 antibodies were functionalized with DNA aptamers both through N-terminal modification and through lysine modification (FIG. 11A-B). The production of constructs was confirmed by SDS-PAGE analysis (FIG. 12A). The binding specificity of antibody-DNA aptamer conjugates was determined by flow cytometry. Both the antibody and the DNA aptamer components of the conjugates retained their binding specificities to the target cells (FIG. 12B). Jurkat (a target cell line of sgc8c aptamer) and Ramos (a target cell line of TD05.1 aptamer) cells were used to confirm the binding specificities of the aptamer moieties of the antibody-aptamer conjugates. Various anti-HER2 antibody-aptamer conjugates were also shown to bind to the MCF7 clone 18 cell line that overexpresses HER2 receptors.

Examples of amino acid sequences of anti-HER2 heavy and light chains, and nucleotide sequence encoding same, are presented in FIGS. 13A-C.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A modified Fc polypeptide, wherein the modified Fc polypeptide is described by the following structure:

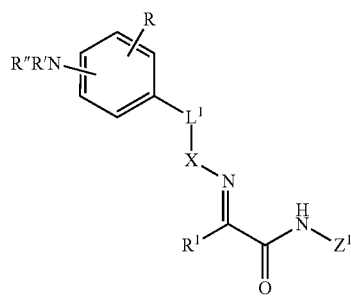

wherein:
- $L^1$ is a linker;
- X is O or NH;
- R' and R" are each independently H, an alkyl or an aryl;
- R is one or more groups, independently selected from hydrogen, an alkyl, an aryl, a hydroxy, an alkoxy, an aryloxy, a heterocycle, a cyano, a halogen, an amino, an acyl, an acyloxy, an amido and nitro;
- $R^1$ is the sidechain of an amino acid, H, an alkyl or an aryl; and
- $Z^1$ is an Fc polypeptide.

2. The modified Fc polypeptide of claim 1, wherein:
 i) $Z^1$ includes an N-terminal sequence $Xaa^2$-$Xaa^3$, wherein $Xaa^2$ and $Xaa^3$ are independently amino acid residues and at least one of $Xaa^2$ and $Xaa^3$ is a basic amino acid residue; and
 and $R^1$ is the amino acid sidechain of alanine; or
 ii) $Z^1$ includes an N-terminal sequence $Xaa^2$-$Xaa^3$, wherein $Xaa^2$ and $Xaa^3$ are independently amino acid residues, and at least one of $Xaa^2$ and $Xaa^3$ is an acidic amino acid residue; or
 iii) $Z^1$ includes an N-terminal sequence $Xaa^2$-$Xaa^3$, wherein $Xaa^2$ and $Xaa^3$ are independently amino acid residues; and
 $R^1$ is the amino acid sidechain of glutamic acid or aspartic acid.

3. The modified Fc polypeptide of claim 1, wherein:
 a) $L^1$ is —$(CH_2)_m$—NHCO—$CH_2$— or —$(CH_2)_m$—CONH—$CH_2$—, and X is O or NH, wherein m is 1 to 6; or
 b) $L^1$ is —$(CH_2)_m$—NHCO— or —$(CH_2)_m$—CONH—, and X is NH, wherein m is 1 to 6.

4. The modified Fc polypeptide of claim 1, wherein the modified Fc polypeptide comprises an antigen-binding domain.

5. A method of conjugating a heterologous functional moiety to the modified Fc polypeptide of claim 1, the method comprising:
 contacting the modified Fc polypeptide of claim 1 with a heterologous functional moiety comprising an aminophenol, a 2-methoxyphenol, an aniline, an azidophenol, or a phenylene diamine group under conditions sufficient to produce a Fc conjugate via oxidative coupling.

6. The method of claim 5, wherein the Fc conjugate is described by one of the following structures:

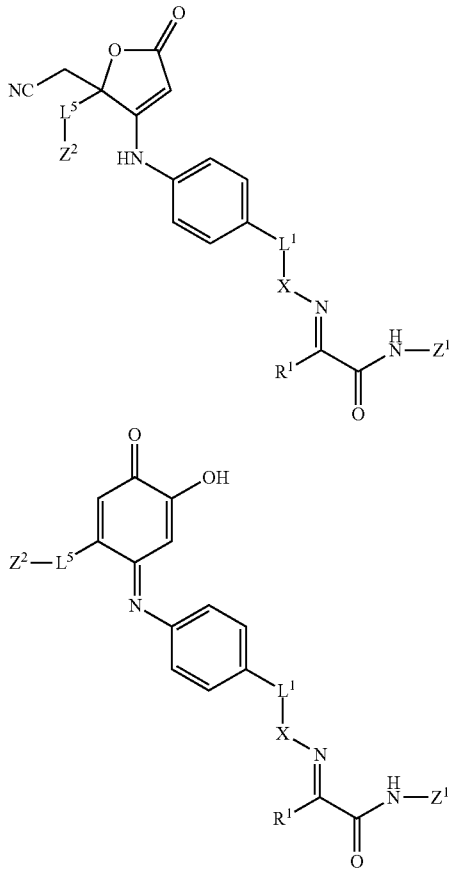

wherein:
L¹ and L⁵ are optional linkers;
Z² is a heterologous functional moiety;
X is O or NH;
R¹ is the sidechain of an amino acid, H, an alkyl or an aryl; and
Z¹ is an Fc polypeptide.

7. The method of claim 6, wherein:
   a) Z¹ includes N-terminal lysine-threonine residues, and R¹ is the amino acid sidechain of alanine; or
   b) R¹ is the amino acid sidechain of glutamic acid or aspartic acid.

8. An Fc conjugate comprising:
   a) a modified Fc polypeptide of claim 1; and
   b) a covalently linked heterologous functional moiety.

9. The Fc conjugate of claim 8, wherein the heterologous functional moiety is a polypeptide, a nucleic acid, a peptoid, an aptamer, an oligosaccharide, a nanoparticle, a small molecule drug, a ligand, a polymer, a liposome, or a drug delivery vehicle.

10. The Fc conjugate of claim 8, wherein the Fc conjugate is described by one of the following structures:

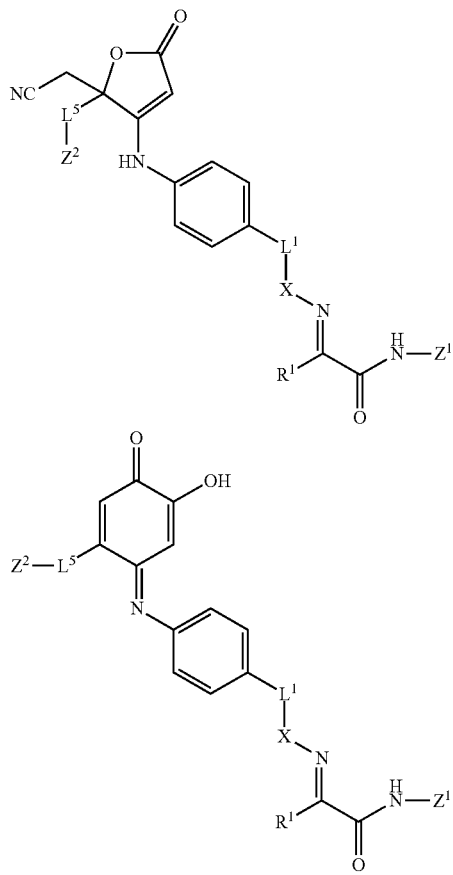

wherein:
L¹ and L⁵ are optional linkers;
Z² is a heterologous functional moiety;
X is O or NH;
R¹ is the sidechain of an amino acid, H, an alkyl or an aryl; and
Z¹ is an Fc polypeptide.

11. The Fc conjugate of claim 8, wherein the modified Fc polypeptide comprises an antigen-binding domain.

12. An antibody comprising:
   a) the Fc conjugate of claim 8; and
   b) an antigen-binding region.

13. The modified Fc polypeptide of claim 1, wherein R is H or hydroxyl and R' and R" are each H.

14. A method of preparing a modified Fc polypeptide, the method comprising:
   contacting a parent Fc polypeptide with a transamination reagent to convert the terminal amino group of the parent Fc polypeptide to a ketone or aldehyde group and produce a modified Fc polypeptide; and
   contacting the modified Fc polypeptide with a bifunctional moiety described by the formula:

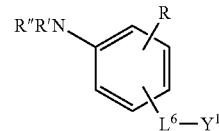

wherein
R is one or more optional aryl substituents;
R' and R" are each independently H, an alkyl or an aryl;
L⁶ is an optional linker; and
Y¹ is —CONHNH₂, —O—NH₂, or —NHNH₂, under conditions sufficient to crosslink the a ketone or aldehyde group to the bifunctional moiety.

15. The method of claim 14, wherein the parent Fc polypeptide is mutated to change the N-terminal amino acid of the parent Fc polypeptide to produce a mutated parent Fc polypeptide, and wherein the mutated parent Fc polypeptide is contacted with the transamination reagent to produce the modified Fc polypeptide.

16. The method of claim 15, wherein:
   a) the mutated Fc polypeptide comprises an N-terminal alanine or an N-terminal glutamic acid; or
   b) the mutated Fc polypeptide comprises N-terminal alanine-lysine-threonine residues.

17. The method of claim 14, wherein the transamination reagent is pyridoxal 5'-phosphate or N-methylpyridinium-4-carboxaldehyde.

\* \* \* \* \*